US009446118B2

(12) United States Patent
Bublot et al.

(10) Patent No.: US 9,446,118 B2
(45) **Date of Patent: *Sep. 20, 2016**

(54) NEWCASTLE DISEASE VIRUS VECTORED HERPESVIRUS VACCINES

(71) Applicant: MERIAL LIMITED, Duluth, GA (US)

(72) Inventors: Michel Bublot, Chaponost (FR); Frederic Reynard, Saint-Bonnet-de-Mure (FR); Herve Poulet, Sante Foy-les-Lyon (FR); Frederic Raymond David, Athens, GA (US)

(73) Assignee: Merial, Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,011

(22) Filed: Feb. 6, 2015

(65) Prior Publication Data

US 2015/0157704 A1 Jun. 11, 2015

Related U.S. Application Data

(63) Continuation of application No. 13/220,196, filed on Aug. 29, 2011, now Pat. No. 8,986,706.

(60) Provisional application No. 61/378,575, filed on Aug. 31, 2010.

(51) Int. Cl.

| | |
|---|---|
| ***A61K 39/17*** | (2006.01) |
| ***A61K 39/12*** | (2006.01) |
| ***A61K 39/245*** | (2006.01) |
| ***C07K 14/005*** | (2006.01) |
| ***C12N 7/00*** | (2006.01) |
| ***C12N 15/86*** | (2006.01) |
| ***A61K 39/00*** | (2006.01) |

(52) U.S. Cl.

CPC ............... *A61K 39/17* (2013.01); *A61K 39/12* (2013.01); *A61K 39/245* (2013.01); *C07K 14/005* (2013.01); *C12N 7/00* (2013.01); *C12N 15/86* (2013.01); *A61K 2039/5256* (2013.01); *A61K 2039/552* (2013.01); *C12N 2710/16722* (2013.01); *C12N 2710/16734* (2013.01); *C12N 2760/18134* (2013.01); *C12N 2760/18143* (2013.01); *C12N 2760/18152* (2013.01)

(58) Field of Classification Search

CPC .. A61K 45/06; A61K 2039/53; A61K 38/00; A61K 39/245; A61K 39/25; A61K 39/12; A61K 39/145; A61K 2039/51; A61K 39/155; A61K 39/17; A61K 39/255; A61K 39/295; A61K 2039/5256; A61K 39/00; A61K 2039/5254; A61K 2039/5258; C12N 2710/16334; C12N 2720/10034; C12N 2760/16134; C12N 2760/18134; C12N 2770/20034; C12N 15/86; C12N 2710/16034; C12N 2750/10034; C12N 2760/18334; C12N 2770/22034; C12N 2770/32434

See application file for complete search history.

(56) References Cited

U.S. PATENT DOCUMENTS

| | | | | |
|---|---|---|---|---|
| 6,010,703 A * | 1/2000 | Maes | C07K 14/005 | 424/199.1 |
| 8,871,220 B2 * | 10/2014 | Bublot | A61K 39/145 | 424/199.1 |
| 2003/0078410 A1 * | 4/2003 | Garcia-Sastre | C07K 14/005 | 536/23.72 |
| 2008/0299149 A1 * | 12/2008 | Wu | C12N 7/00 | 424/199.1 |
| 2010/0255029 A1 * | 10/2010 | Bublot | A61K 39/145 | 424/199.1 |

FOREIGN PATENT DOCUMENTS

| | | | |
|---|---|---|---|
| WO | WO96/13575 | 5/1996 | |
| WO | WO/01/66568 | 9/2001 | |
| WO | WO 2007/104782 | 9/2007 | A16K 39/145 |

OTHER PUBLICATIONS

Gaskell R, et. al. Vet Res. Mar.-Apr. 2007;38(2):337-54. Epub Feb. 13, 2007.*

Alexander DJ, et. al. Avian Pathol. 2012;41(4):329-35.*

Small JC, et. al. Curr Opin Virol. Oct. 2011;1(4):241-5.*

Tai SH, Niikura M, Cheng HH, Kruger JM, Wise AG, Maes RK. Envelope glycoprotein B [Felid herpesvirus 1]. NCBI Reference Sequence: YP_003331552.2. Dec. 17, 2009.*

Maeda K, Horimoto T, Norimine J, Kawaguchi Y, Tomonaga K, Niikura M, Kai C, Takahashi E, Mikami T. Glycoprotein B homolog [feline herpesvirus type 1 FHV-1, Genomic, 3240 nt]. GenBank: S49775. Aug. 5, 1999.*

Tai SH, Niikura M, Cheng HH, Kruger JM, Wise AG, Maes RK. Envelope glycoprotein B [Felid herpesvirus 1]. NCBI Reference Sequence: YP_003331589.. Dec. 17, 2009.*

Tai SH, Niikura M, Cheng HH, Kruger JM, Wise AG, Maes RK. Felid herpesvirus 1 strain C-27, complete genome. GenBank: FJ478159. Dec. 1, 2009.*

Spatz SJ, Petherbridge L, Zhao Y, Nair V. Comparative full-length sequence analysis of oncogenic and vaccine (Rispens) strains of Marek's disease virus. J Gen Virol. Apr. 2007;88(Pt 4):1080-96.*

Khattar SK, et. al. Vaccine. Apr. 19, 2010;28(18):3159-70.*

(Continued)

*Primary Examiner* — Rachel B Gill

(74) *Attorney, Agent, or Firm* — Judy Jarecki-Black; Ruoying Chen; Merial Inc.

(57) ABSTRACT

The present invention encompasses recombinant Newcastle Disease Virus-Herpesvirus vaccines or compositions. The invention encompasses recombinant NDV vectors encoding and expressing herpesvirus pathogen, antigens, proteins, epitopes or immunogens. Such vaccines or compositions can be used to protect animals against disease.

16 Claims, 18 Drawing Sheets

(56) References Cited

OTHER PUBLICATIONS

Afonso,C.L., Perozo,F. and Villegas,P. Newcastle disease virus strain VG/GA, complete genome. GenBank Accession No. EU289028. Dep. Dec. 1, 2008.*

Bwala DG, Abolnik C, van Wyk A, Cornelius E, Bisschop SP. Efficacy of a genotype 2 Newcastle disease vaccine (Avinew) against challenge with highly virulent genotypes 5d and 3d. J S Afr Vet Assoc. Sep. 2009;80(3):174-8.*

Krishnamurthy et al., Virology 278, 168-182,2000, "Reccvery of a Virulent Strain of Newcastle Disease Virus from Cloned cDNA: Expression of a Foreign Gene Results in Growth Retardation and Attenuation".

Huang et al., J. Gen. Virol. 82, 1729-1736, 2001, "High-level expression of a foreign gene from the most 3'-proximal locus of a recombinant Newcastle disease virus".

Nakaya et al., J. Virol. 75, 11868-11873, 2001, "Recombinant Newcastle Disease Virus as a Vaccine Vector".

Park et al. PNAS 103, 8203-8208, 2006, "Engineered viral vaccine constructs with dual specificity: avian influenza and newcastle disease".

Veits et al PNAS 103, 8197-8202, 2006, "Newcastle disease virus expressing H5 hemagglutinin gene protects chickens against Newcastle disease and avian influenza".

Ge et al. J. Virol. 81, 150-158, 2007, "Newcastle disease virus-based live attenuated vaccine completely protects chickens and mice from lethal challenge of homologous and heterologous H5N1 avian influenza viruses".

Romer-Oberdörfer et al. Vaccine 26, 2307-2313, 2008, "Level of protection of chickens against highly pathogeonic H5 avian influenza virus with Newcastle disease virus based live attenuated vector vaccine depends on homology of H5 sequence between vaccine and challenge virus".

Alexander, D. J., Diseases of Poultry, Iowa State Uni. Press, Ames IA, 541-569, 1997, "Newcastle disease and other avian paramyxoviridae infections".

Steward et al., 1993, Journal of General Virology 74:2539-2547, "RNA editing in Newcastle disease virus".

Conzelmann, K.K., Ann. Rev. Genet. 32, 123-162, 1998, "Nonsegmented negative-strand RNA viruses: Genetics and manimupation of Viral Genomics".

Roberts and Rose, Virology 247, 1-6, 1998, "Recovery of negative-strand RNA viruses from plasmid DNAs: a positive approach revitalizes a negative field".

Palese et al., PNAS 93, 11354-11358, 1996, "Negative-strand RNA viruses: Genetic engineering and appliations".

Nagai, Y., Rev. Med. Virol. 9, 83-99, 1999, "Paramyxovirus replication and pathogenesis. Reverse Genetics transforms understanding".

Bukreyev et al., J. Virol. 70, 6634-6641, 1996, "Recovery of infectious respiratory syncytial virus expressing an additional, foreign gene".

Mebatsion et al., PNAS 93, 7310-7314,1996, "Highly stable expression of a foreign gene from rabies virus vectors".

Schnell et al., PNAS 93, 11359-11365,1996, "Foreign glycoproteins expressed from recombinant vesicular stomatitis viruses are incorporated efficiently into virus particles".

Hasan et al., J. Gen. Virol. 78, 2813-2820,1997, "Creation of an infectious recombinant Sendai virus expressing the firefly luciferase gene from the 3' proximal first locus".

He et al., Virology 237, 249-260,1997, "Recovery of infectious SV5 from cloned DNA and expression of a foreign gene".

Sakai et al., FEBS Lett. 45, 221-226,1999, "Accomodaticn of foreign genes into the sendai virus genome: sizes of inserted genes and viral replication".

Maeda et al., Virology 202, 1034-8, 1994, "A gD homologous gene of feline herpesvirus type 1 encodes a hemagglutinin (gp60)".

Maeda et al., Virus Res 39, 55-61, 1995, "Expression and identification of the feline herpesvirus type 1 glycoprotein B (gp143/108)".

Maeda et al., Virus Res. 46, 75-80, 1996, "Expression and properties of feline herpesvirus type 1 gD (hemagglutinin) by a rrecombinant baculovirus".

Spatz and Maes, Virology 197, 125-36, 1993, "Immunological characterization of the feline Herpesvirus-1 glycoprotein B and analysis of its deduced amino acid sequence".

Horimoto et al., Arch Virol 111, 127-32, 1990, "Feline herpesvirus type 1 glycoprotein eliciting virus neutralizing and hemagglutination-inhibiting antibodies".

Tai S H S et al., "Complete genomic sequence and an infectious BAC clone of feline herpesvirus-1 (FHV-1)", Virology, 2010, vol. 4012, p. 215-227.

Sonoda J, et al., J Virol. 2000, 74(7):3217-26.

Spatz et al., J Gen Virol. 1994 75:1235-44, GenBank Acc. No. AAB30980.

Spatz et al., Virology, 1993, 197(1) : 125-36, GenBank Acc. No. AAB28559.

* cited by examiner

Figure 1A

| SEQ ID NO: | Type | Gene |
|---|---|---|
| 1 | protein | FHV gB protein |
| 2 | DNA | Codon-optimized FHV gB DNA |
| 3 | DNA | Wild-type FHV gB DNA (GenBank No. FJ478159 encoding AAB28559.3) |
| 4 | Protein | FHV gD protein (GenBank No. AAB30980.1) |
| 5 | DNA | Codon-optimized FHV gD DNA |
| 6 | DNA | Wild-type FHV gD DNA (GenBank No. FJ478159) |
| 7 | protein | gB protein of GenBank accession No. 1911192A (feline Herpesvirus) (99.2%) |
| 8 | protein | gB protein of GenBank accession No. AAB28559 (feline Herpesvirus) (100%) |
| 9 | protein | gB protein of GenBank accession No. AAB24381 (feline Herpesvirus) (99.6%) |
| 10 | DNA | gB DNA of GenBank accession No. S49775 encoding AAB24381 |
| 11 | protein | gB protein of GenBank accession No. AAK51052 (canine Herpesvirus) (71.7%) |
| 12 | DNA | gB DNA of GenBank accession No. AF361073 encoding AAK51052 |
| 13 | protein | gB protein of GenBank accession No. AAT93732 (canine Herpesvirus) (71.6%) |
| 14 | DNA | gB DNA of GenBank accession No. AY582737 encoding AAT93732 |
| 15 | protein | gB protein of GenBank accession No. CAA92272 (phocid Herpesvirus) (70.2%) |
| 16 | DNA | gB DNA of GenBank accession No. Z68147 encoding CAA92272 |
| 17 | protein | gD protein of GenBank accession No. BAA44951 (feline Herpesvirus) (100%) |
| 18 | DNA | gD DNA of GenBank accession No. D42113 encoding BAA44951 |
| 19 | protein | gD protein of GenBank accession No. AAB67058 (canine Herpesvirus) (39.4%) |
| 20 | DNA | gD DNA of GenBank accession No. CHU84223 encoding AAB67058 |
| 21 | protein | gD protein of GenBank accession No. AAK51062 (canine Herpesvirus) (39.4%) |
| 22 | DNA | gD DNA of GenBank accession No. AF361076 encoding AAK51062 |
| 23 | protein | gD protein of GenBank accession No. CAC51465 (phocid Herpesvirus) (37.9%) |
| 24 | DNA | gD DNA of GenBank accession No. AJ290955 encoding CAC51465 |

| Figure 1B | | |
|---|---|---|
| 25 | oligo | Primer FR09 |
| 26 | oligo | Primer FR10 |
| 27 | DNA | AVINEW NDV genome sequence |

Figure 4
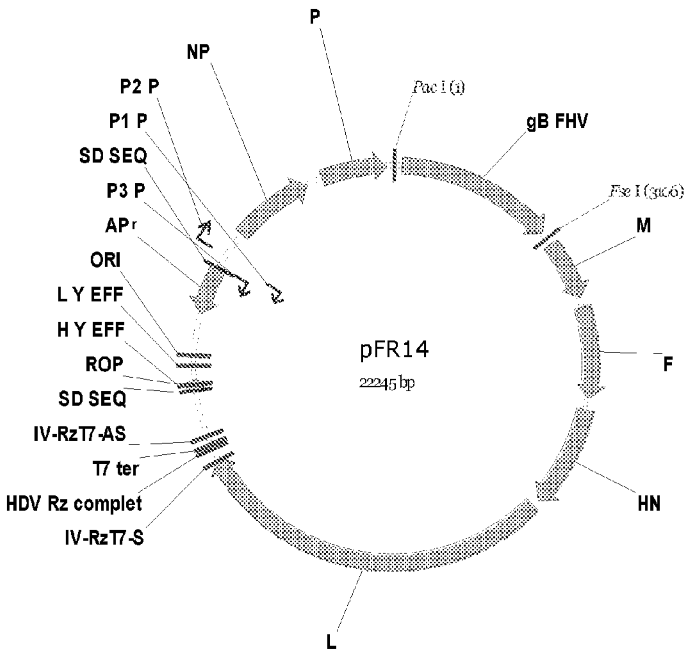
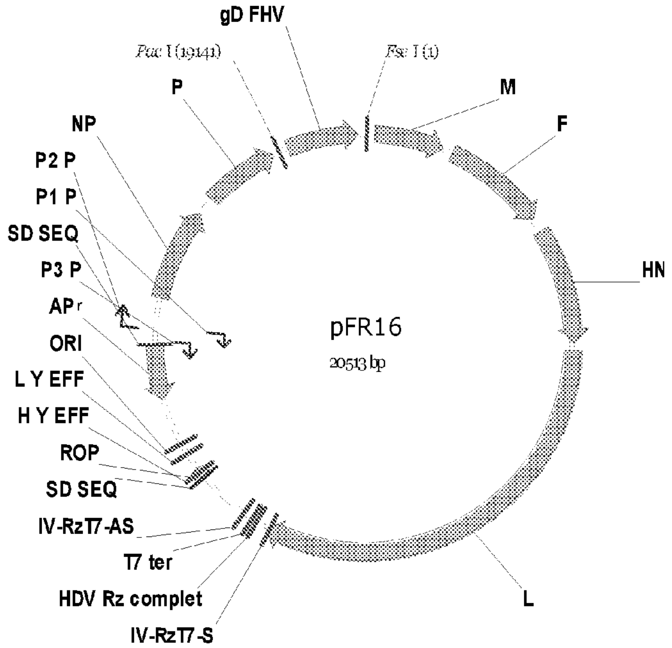

1 – group A; 2- group B; 3 – group C; 4 – group D

Serology: Anti-FHV-1 gB Ab titers determined by ELISA.

Figure 12A gB protein alignment

```
                                1                                                 50
         1911192A (gB)     (1)  MSTRGDLGKRRRGSRWQGHSGYPRQRCFFPSLLGIAATGSRHGNGSSGLT
         AAB24381 (gB)     (1)  MSTRGDLGKRRRGSRWQGHSGYFRQRCFFPSLLGIAATGSRHGNGSSGLT
         AAK51052 (gB)     (1)  ------------------------------------------------MF
         AAT93732 (gB)     (1)  ------------------------------------------------MF
         CAA92272 (gB)     (1)  ------------------------------------------------MY
         AAB28559 (gB)     (1)  MSTRGDLGKRRRGSRWQGHSGYFRQRCFFPSLLGIAATGSRHGNGSSGLT
SEQ 1 (gB protein)        (1)  MSTRGDLGKRRRGSRWQGHSGYFRQRCFFPSLLGIAATGSRHGNGSSGLT

                                51                                               100
         1911192A (gB)    (51)  RLARYVSFIWIVLFLVGPRPVEGQSGSTSEQPRRTVATPEVGGTPPKPTT
         AAB24381 (gB)    (51)  RLARYVSFIWIVLFLVGPRPVEGQSGSTSEQPRRTVATPEVGGTPPKPTT
         AAK51052 (gB)     (3)  SLYLYIFFIIYTLIICDPTTPESTINPLN-----------HHNLS----T
         AAT93732 (gB)     (3)  SLYLYIFFIIYTLIICDPTTPESTINPLN-----------HHNLS----T
         CAA92272 (gB)     (3)  LITLVFFINILVIQCVPTTQPTESTPPITPSP-------PPKNSS----S
         AAB28559 (gB)    (51)  RLARYVSFIWIVLFLVGPRPVEGQSGSTSEQPRRTVATPEVGGTPPKPTT
SEQ 1 (gB protein)       (51)  RLARYVSFIWIVLFLVGPRPVEGQSGSTSEQPRRTVATPEVGGTPPKPTT

                                101                                              150
         1911192A (gB)   (101)  DPTDMSDMREALRASQIEANGPSTFYMCPPPSGSTVVRLEPPRACPDYKL
         AAB24381 (gB)   (101)  DPTDMSDMREALRASQIEANGPSTFYMCPPPSGSTVVRLEPPRACPDYKL
         AAK51052 (gB)    (38)  PKPTSDDIREILRESQIESDDTSTFYMCPPPSGSTLVRLEPPRACPNYKL
         AAT93732 (gB)    (38)  PKPTSDDIREILRESQIESDDTSTFYMCPPPSGSTLVRLEPPRACPNYKL
         CAA92272 (gB)    (42)  NTELNDDMREILGESQIESDDTATFFMCPPPSGSTLVRLEPPRACPNYKL
         AAB28559 (gB)   (101)  DPTDMSDMREALRASQIEANGPSTFYMCPPPSGSTVVRLEPPRACPDYKL
SEQ 1 (gB protein)      (101)  DPTDMSDMREALRASQIEANGPSTFYMCPPPSGSTVVRLEPPRACPDYKL

                                151                                              200
         1911192A (gB)   (151)  GKNFTEGIAVIFKENIAPYKFKANIYYKNIIMTTVWSGSSYAVTTNRYTD
         AAB24381 (gB)   (151)  GKNFTEGIAVIFKENIAPYKFKANIYYKNIIMTTVWSGSSYAVTTNRYTD
         AAK51052 (gB)    (88)  GKNFTEGIAVIFKENISPYKFKANIYYKNIIITTVWSGSTYAVITNRYTD
         AAT93732 (gB)    (88)  GKNFTEGIAVIFKGNISPYKFKANIYYKNIIITTVWSGSTYAVITNKYTD
         CAA92272 (gB)    (92)  GKNFTEGIAVIFKENISPYKFKANIYYKNIIITTVWSGSSYAVVTNMHTD
         AAB28559 (gB)   (151)  GKNFTEGIAVIFKENIAPYKFKANIYYKNIIMTTVWSGSSYAVTTNRYTD
SEQ 1 (gB protein)      (151)  GKNFTEGIAVIFKENIAPYKFKANIYYKNIIMTTVWSGSSYAVTTNRYTD

                                201                                              250
         1911192A (gB)   (201)  RVPVKVQEITDLIDRRGMCLSKADYVRNNYQFTAFDRDEDPRELPLKPSK
         AAB24381 (gB)   (201)  RVPVKVQEITDLIDRRGMCLSKADYVRNNYQFTAFDRDEDPRELPLKPSK
         AAK51052 (gB)   (138)  RVPIGVPEITELIDRRGMCLSKADYIRNNYEFTAFDKDEDPREVHLKPSK
         AAT93732 (gB)   (138)  RVPIGVPEITELIDRRGMCLSKADYIRNNYEFTAFDKDEDPREVHLKPSK
         CAA92272 (gB)   (142)  RVPIEVQEITELIDRRGMCLSKADYIRNNYEFTAFDKDEDPREMHLKPSK
         AAB28559 (gB)   (201)  RVPVKVQEITDLIDRRGMCLSKADYVRNNYQFTAFDRDEDPRELPLKPSK
SEQ 1 (gB protein)      (201)  RVPVKVQEITDLIDRRGMCLSKADYVRNNYQFTAFDRDEDPRELPLKPSK

                                251                                              300
         1911192A (gB)   (251)  FNTPQSRGWHTTNETYTKIGAAGFHHSGTSVNCIVEEVDARSVYPYDSFA
         AAB24381 (gB)   (251)  FNTPESRGWHTTNETYTKIGAAGFHHSGTSVNCIVEEVDARSVYPYDSFA
         AAK51052 (gB)   (188)  FNTPGSRGWHTVNDTYTKIGGSGFYHSGTSVNCIVEEVDARSVYPYDSFA
         AAT93732 (gB)   (188)  FNTPGSRGWHTVNDTYTKIGGSGFYHSGTSVNCIVEEVDARSVYPYDSFA
         CAA92272 (gB)   (192)  FNTPGSRGWHTTNDTYTKIGSPGFYRTGTSVNCIVEEVDARSVYPYDSFG
         AAB28559 (gB)   (251)  FNTPESRGWHTTNETYTKIGAAGFHHSGTSVNCIVEEVDARSVYPYDSFA
SEQ 1 (gB protein)      (251)  FNTPESRGWHTTNETYTKIGAAGFHHSGTSVNCIVEEVDARSVYPYDSFA

                                301                                              350
         1911192A (gB)   (301)  ISTGDVIHMSPFFGLRDGAHVEHTSYSSDRFQQIEGYYPIDLDTRLQLGA
         AAB24381 (gB)   (301)  ISTGDVIHMSPFFGLRDGAHVEHTSYSSDRFQQIEGYYPIDLDTRLQLGA
         AAK51052 (gB)   (238)  ISTGDIIHMSPFFGLRDGAHTEYISYSTDRFQQIEGYYPIDLDTRLQLGA
         AAT93732 (gB)   (238)  ISTGDIIHMSPFFGLRDGAHTEYISYSTDRFQQIEGYYPIDLDTRLQLGA
         CAA92272 (gB)   (242)  ISTGDIIHMSPFFGLRDGAHTEHTSYSNDRFQQIEGYYPIDLDTRLQVSG
         AAB28559 (gB)   (301)  ISTGDVIHMSPFFGLRDGAHVEHTSYSSDRFQQIEGYYPIDLDTRLQLGA
SEQ 1 (gB protein)      (301)  ISTGDVIHMSPFFGLRDGAHVEHTSYSSDRFQQIEGYYPIDLDTRLQLGA
```

Figure 12B

| | | 351 … 400 |
|---|---|---|
| 1911192A (gB) | (351) | PVSRNFLETPHVTVAWNWTPKCGRVCTLAKWREIDEMLRDEYQGSYRFTV |
| AAB24381 (gB) | (351) | PVSRNFLETPHVTVAWNWTPKCGRVCTLAKWREIDEMLRDEYQGSYRFTV |
| AAK51052 (gB) | (288) | PVSRNFLTTQHVTVAWNWVPKIREVCTLAKWREIDEIIRDEYKGSYRFTA |
| AAT93732 (gB) | (288) | PVSRNFLTTQHVTVAWNWVPKIREVCTLAKWREIDEIIRDEYKGSYRFTA |
| CAA92272 (gB) | (292) | PVSRNFLTTQHVTVAWNWVPKIREVCTLAKWREIDEIIRDEYKGSYRFTA |
| AAB28559 (gB) | (351) | PVSRNFLETPHVTVAWNWTPKSGRVCTLAKWREIDEMLRDEYQGSYRFTA |
| SEQ 1 (gB protein) | (351) | PVSRNFLETPHVTVAWNWTPKSGRVCTLAKWREIDEMLRDEYQGSYRFTA |

| | | 401 … 450 |
|---|---|---|
| 1911192A (gB) | (401) | KTISATFISNTSQFEINRIRLGDCATKEAAEAIDRIYKSKYSKTHIQTGT |
| AAB24381 (gB) | (401) | KTISATFISNTSQFEINRIRLGDCATKEAAEAIDRIYKSKYSKTHIQTGT |
| AAK51052 (gB) | (338) | KSISATFISDTTQFDIDRVKLSDCAKREAIEAIDKIYKKKYNKTHIQTGE |
| AAT93732 (gB) | (338) | KSISATFISDTTQFDIDRVKLSDCAKREAIEAIDKIYKKKYNKTHIQTGE |
| CAA92272 (gB) | (342) | KSISATFISDATQFDINRVKLSDCAKREATEAIDKIYNNKYNKTHIQTGE |
| AAB28559 (gB) | (401) | KTISATFISNTSQFEINRIRLGDCATKEAAEAIDRIYKSKYSKTHIQTGT |
| SEQ 1 (gB protein) | (401) | KTISATFISNTSQFEINRIRLGDCATKEAAEAIDRIYKSKYSKTHIQTGT |

| | | 451 … 500 |
|---|---|---|
| 1911192A (gB) | (451) | LETYLARGGFLIAFRPMISNELAKLYINELARSNRTVDLSALLNPSGETV |
| AAB24381 (gB) | (451) | LETYLARGGFLIAFRPMISNELAKLYINELARSNRTVDLSALLNPSGETV |
| AAK51052 (gB) | (388) | LETYLARGGFIIAFRPMISNELAKLYINELVRSNRTVDLKSLLNPSVRGG |
| AAT93732 (gB) | (388) | LETYLARGGFIIAFRPMISNELAKLYINELVRSNRTVDLKSLLNPSVRGG |
| CAA92272 (gB) | (392) | LETYLARGGFIIAFRPMISNELAKLYINELARSERIVDLNALLNPSHSVG |
| AAB28559 (gB) | (451) | LETYLARGGFLIAFRPMISNELAKLYINELARSNRTVDLSALLNPSGETV |
| SEQ 1 (gB protein) | (451) | LETYLARGGFLIAFRPMISNELAKLYINELARSNRTVDLSALLNPSGETV |

| | | 501 … 550 |
|---|---|---|
| 1911192A (gB) | (501) | QRTRGSVPSNQHHRSRRSTIEGGIETVNNASLLKTTSSVEFAMIQFAYDY |
| AAB24381 (gB) | (501) | QRTRRSVPSNQHHRSRRSTIEGGIETVNNASLLKTTSSVEFAMLQFAYDY |
| AAK51052 (gB) | (438) | ARKRRSVEENKR--SKR-NIEGGIENVNNSTIIKTTSSVHFAMLQFAYDH |
| AAT93732 (gB) | (438) | ARKRRSVESNKR--SKR-NIEGGIENVNNSTIIKTTSSVHFAMLQFAYDH |
| CAA92272 (gB) | (442) | GRKKRSIETSTLGRSKR-DVDGGVQNVNNATLIKTTSSIHFAMLQFAYDH |
| AAB28559 (gB) | (501) | QRTRRSVPSNQHHRSRRSTIEGGIETVNNASLLKTTSSVEFAMLQFAYDY |
| SEQ 1 (gB protein) | (501) | QRTRRSVPSNQHHRSRRSTIEGGIETVNNASLLKTTSSVEFAMLQFAYDY |

| | | 551 … 600 |
|---|---|---|
| 1911192A (gB) | (551) | IQAHVNEMLSRIATAWCTLQNREHVLWTETLKLNPGGVVSMALERRVSAR |
| AAB24381 (gB) | (551) | IQAHVNEMLSRIATAWCTLQNREHVLWTETLKLNPGGVVSMALERRVSAR |
| AAK51052 (gB) | (485) | IQSHVNEMLSRIATAWCNLQNKERTLWNEVMKLNPTSVASVAMDQRVSAR |
| AAT93732 (gB) | (485) | IQSHVNEMLSRIATAWCNLQNKERTLWNEVMKLNPTSVASVAMDQRVSAR |
| CAA92272 (gB) | (491) | IQSHVNEMLSRIATAWCNLQNKERTLWNEVMKLNPTSITSTIMDQKVSAR |
| AAB28559 (gB) | (551) | IQAHVNEMLSRIATAWCTLQNREHVLWTETLKLNPGGVVSMALERRVSAR |
| SEQ 1 (gB protein) | (551) | IQAHVNEMLSRIATAWCTLQNREHVLWTETLKLNPGGVVSMALERRVSAR |

| | | 601 … 650 |
|---|---|---|
| 1911192A (gB) | (601) | LLGDAVAVTQCVNISSGHVYIQNSMRVTGSSTTCYSRPLVSFRALN-DSE |
| AAB24381 (gB) | (601) | LLGDAVAVTQCVNISSGHVYIQNSMRVTGSSTTCYSRPLVSFRALN-DSE |
| AAK51052 (gB) | (535) | MLGDVLAVTQCVNISGSSVFIQNSMRVLGSTTTCYSRPLISFKALENSTN |
| AAT93732 (gB) | (535) | MLGDVLAVTQCVNISGSSVFIQNSMRVLGSTTTCYSRPLISFKALENSTN |
| CAA92272 (gB) | (541) | LLGDVIAVTQCVNISGSNVFIQNSMRVTGSTTTCYSRPLISFKALENSTD |
| AAB28559 (gB) | (601) | LLGDAVAVTQCVNISSGHVYIQNSMRVTGSSTTCYSRPLVSFRALN-DSE |
| SEQ 1 (gB protein) | (601) | LLGDAVAVTQCVNISSGHVYIQNSMRVTGSSTTCYSRPLVSFRALN-DSE |

| | | 651 … 700 |
|---|---|---|
| 1911192A (gB) | (650) | YIEGQLGENNDLLVERKLIEPCTVNNKRYFKFGADYVYFEDYAYVRKVPL |
| AAB24381 (gB) | (650) | YIEGQLGENNDLLVERKLIEPCTVNHKRYFKFGADYVYFEDYAYVRKVPL |
| AAK51052 (gB) | (585) | YIEGQLGENNELLVERKLIEPCTANHKRYFKFGVDYVYFENYAYVRKVPL |
| AAT93732 (gB) | (585) | YIEGQLGENNELLVERKLIEPCTANHKRYFKFGVDYVYFENYAYVRKVPL |
| CAA92272 (gB) | (591) | YIEGQLGENNELLVDRKLIEPCTANHKRYFKFGVDYVYFENYVYIRKVPL |
| AAB28559 (gB) | (650) | YIEGQLGENNELLVERKLIEPCTVNHKRYFKFGADYVYFEDYAYVRKVPL |
| SEQ 1 (gB protein) | (650) | YIEGQLGENNELLVERKLIEPCTVNNKRYFKFGADYVYFEDYAYVRKVPL |

Figure 12C

```
                                701                                               750
         1911192A (gB)   (700)  SEIELISAYVDLNLTLLEDREFLPLEVYTRAELEDTGLLDYSEIQRRNQL
         AAB24381 (gB)   (700)  SEIELISAYVDLNLTLLEDREFLPLEVYTRAELEDTGLLDYSEIQRRNQL
         AAK51052 (gB)   (635)  NEIEMISAYVDLNITLLEDREFLPLEVYTRAELEDTGLLDYSEIQRRNQL
         AAT93732 (gB)   (635)  NEIEMISAYVDLNITLLEDREFLPLEVYTRAELEDTGLLDYSEIQRRNQL
         CAA92272 (gB)   (641)  NEIEMISTYVDLNITLLEDREFLPLEVYTRAELEDTGLLDYSEIQRRNQL
         AAB28559 (gB)   (700)  SEIELISAYVDLNLTLLEDREFLPLEVYTRAELEDTGLLDYSEIQRRNQL
SEQ 1 (gB protein)       (700)  SEIELISAYVDLNLTLLEDREFLPLEVYTRAELEDTGLLDYSEIQRRNQL

                                751                                               800
         1911192A (gB)   (750)  HALKFYDIDSIVKVDNNLVIMRGMANFFQGLGDVGAGFGKVVLGAASAVI
         AAB24381 (gB)   (750)  HALKFYDIDSIVKVDNNLVIMRGMANFFQGLGDVGAGFGKVVLGAASAVI
         AAK51052 (gB)   (685)  HALKFYDIDSVVKVDNNVVIMRGIANFFQGLGDVGAGFGKVVLGAANAVI
         AAT93732 (gB)   (685)  HALKFYDIDSVVKVDNNVVIMRGIANFFQGLGDVGAGFGKVVLGAANAVI
         CAA92272 (gB)   (691)  HALKFYDIDSVVKVDNNLIIMRGMLTFFQGLGDVGAGFGKVVLGAANAVI
         AAB28559 (gB)   (750)  HALKFYDIDSIVKVDNNLVIMRGMANFFQGLGDVGAGFGKVVLGAASAVI
SEQ 1 (gB protein)       (750)  HALKFYDIDSIVKVDNNLVIMRGMANFFQGLGDVGAGFGKVVLGAASAVI

                                801                                               850
         1911192A (gB)   (800)  STVSGVSSFLNNPFGALAVGLLILAGIVAAFLAYRYISRLRANPMKALYP
         AAB24381 (gB)   (800)  STVSGVSSFLNNPFGALAVGLLILAGIVAAFLAYRYISRLRANPMKALYP
         AAK51052 (gB)   (735)  ATVSGVSSFLNNPFGALAVGLLILAGLFAAFLAYRYVSKLKSNPMKALYP
         AAT93732 (gB)   (735)  ATVSGVSSFLNNPFGALAVGLLILAGLFAAFLAYRYVSKLKSNPMKALYP
         CAA92272 (gB)   (741)  STVSGISSFLNNPFGALAVGLLILAGLFAAFLAYRYVSKLKSNPMKALYP
         AAB28559 (gB)   (800)  STVSGVSSFLNNPFGALAVGLLILAGIVAAFLAYRYISRLRANPMKALYP
SEQ 1 (gB protein)       (800)  STVSGVSSFLNNPFGALAVGLLILAGIVAAFLAYRYISRLRANPMKALYP

                                851                                               900
         1911192A (gB)   (850)  VTTKNLKQTAKSPASTAGGDSDPGVDDFDEEKLMQAREMIKYMSLVSAME
         AAB24381 (gB)   (850)  VTTKNLKQTAKSPASTAGGDSDPGVDDFDEEKLMQAREMIKYMSLVSAME
         AAK51052 (gB)   (785)  VTTKNLKESVKNGNSGNNSDGEENDDNIDEEKLQQAKEMIKYMSLVSAME
         AAT93732 (gB)   (785)  VTTKNLKESVKNGNSGNNSDGEENDDNIDEEKLQQAKEMIKYMSLVSAME
         CAA92272 (gB)   (791)  VTTKNLKESSKE----KIGDGDEDGDEFDEDNLSQAKEMIKYMTLISAME
         AAB28559 (gB)   (850)  VTTKNLKQTAKSPASTAGGDSDPGVDDFDEEKLMQAREMIKYMSLVSAME
SEQ 1 (gB protein)       (850)  VTTKNLKQTAKSPASTAGGDSDPGVDDFDEEKLMQAREMIKYMSLVSAME

                                901                                               950
         1911192A (gB)   (900)  QQEHKAMKKNKGPAILTSHLTNMALRRRGPKYQRLNNLDSGDDTETNLV-
         AAB24381 (gB)   (900)  QQEHKAMKKNKGPAILTSHLTNMALRRRGPKYQRLNNLDSGDDTETNLV-
         AAK51052 (gB)   (835)  QQEHKAIKKNSGPALLASHITNLSLKRRGPKYKRLKNVNENESKV-----
         AAT93732 (gB)   (835)  QQEHKAIKKNSGPALLASHITNLSLKRRGPKYKRLKNVNENESKV-----
         CAA92272 (gB)   (837)  KQEHKAMKKNSGPAILANRVANLALKRRGPKYKRLKNMDDENDEV-----
         AAB28559 (gB)   (900)  QQEHKAMKKNKGPAILTSHLTNMALRRRGPKYQRLNNLDSGDDTETNLV-
SEQ 1 (gB protein)       (900)  QQEHKAMKKNKGPAILTSHLTNMALRRRGPKYQRLNNLDSGDDTETNLV-
```

| | SEQ ID NO:1 (gB protein) (sequence identity percentage) |
|---|---|
| 1911192A(gB)SEQ ID NO:7 | 99.2% |
| AAB24381(gB)SEQ ID NO:9 | 99.6% |
| AAK51052(gB)SEQ ID NO:11 | 71.7% |
| AAT93732(gB)SEQ ID NO:13 | 71.6% |
| CAA92272(gB)SEQ ID NO:15 | 70.2% |
| AAB28559(gB)SEQ ID NO:8 | 100% |

Figure 13A gD protein alignment

```
                                1                                                50
         AAB67058 (gD)    (1)   ------------------MIKLLFILFYFN--PITGYKWVDPPRRYNYTV
         AAK51062 (gD)    (1)   ------------------MIKLLFILFYFN--PITGYKWVDPPRRYNYTV
         CAC51465 (gD)    (1)   ------------------MIGLIIFIFFYNGNIAIAYNWIVQPLRYNYTV
         BAA44951 (gD)    (1)   MMTRLHFWWCGIFAVLKYLVCTSSLTTTPKTTTVYVKGFNIPPLRYNYTQ
  SEQ 4 (gD protein)    (1)   MMTRLHFWWCGIFAVLKYLVCTSSLTTTPKTTTVYVKGFNIPPLRYNYTQ

                                51                                              100
         AAB67058 (gD)   (31)   LRMIPDIPNPMDPSKNAEVRYVTSTDPCDMVALISNPNIESTIKTIQFVQ
         AAK51062 (gD)   (31)   LRMIPDIPNPMDPSKNAEVRYVTSTDPCDMVALISNPNIESTIKTIQFVQ
         CAC51465 (gD)   (33)   LDLRPNIPNPMDSSKNAEVRYVTSTDPCGMVALISEPNIESTIKTIQFVN
         BAA44951 (gD)   (51)   ARIVPKIPQAMDPKITAEVRYVTSMDSCGMVALISEPDIDATIRTIQLSQ
  SEQ 4 (gD protein)   (51)   ARIVPKIPQAMDPKITAEVRYVTSMDSCGMVALISEPDIDATIRTIQLSQ

                                101                                             150
         AAB67058 (gD)   (81)   KKKFYNASLSWFKVGDDCTYPIYLIQYFDCDPQREFGICLKRSPDFWKPS
         AAK51062 (gD)   (81)   KKKFYNASLSWFKVGDDCTYPIYLIQYFDCDPQREFGICLKRSPDFWKPS
         CAC51465 (gD)   (83)   KKKYYNASLSWFKVGDDCTYPIYLIKYFNCDPQKEFGICLKRTPDYWKPS
         BAA44951 (gD)  (101)   KK-TYNATISWFKVTQGCEYPMFLMDMRLCDPKREFGICALRSPSYWLEP
  SEQ 4 (gD protein)  (101)   KK-TYNATISWFKVTQGCEYPMFLMDMRLCDPKREFGICALRSPSYWLEP

                                151                                             200
         AAB67058 (gD)  (131)   LVGYTFLTDDELGLVLAAPAPFNQGQYRRVIQIENEVFYTDFMVQLPRET
         AAK51062 (gD)  (131)   LVGYTFLTDDELGLVLAAPAPFNQGQYRRVIQIENEVFYTDFMVQLPRET
         CAC51465 (gD)  (133)   LIGYSFLTDNELGLVFAAPAPFNQGQYRRVIIIEKSVFYTDFMVKLPKET
         BAA44951 (gD)  (150)   LTKYMFLTDDELGLIMMAPAQFNQGQYRRVITIDGSMFYTDFMVQLSPTP
  SEQ 4 (gD protein)  (150)   LTKYMFLTDDELGLIMMAPAQFNQGQYRRVITIDGSMFYTDFMVQLSPTP

                                201                                             250
         AAB67058 (gD)  (181)   CYPSKEDKFRPTPMEWCKESRSVSASKVDDELFYLNRAGPQTLLKYYVIK
         AAK51062 (gD)  (181)   CYPSKEDKFRPTPMEWCKESRSVSASKVDDELFYLNRAGPQTLLKYYVIK
         CAC51465 (gD)  (183)   CPPPMKDRVSRDLPKWCKRAKEPGPLGTDEESFYLNRAVPQPRLKYYVIR
         BAA44951 (gD)  (200)   CWPAKPDRYSEILHEWCRNVKTIGLDGARDYHYYWVPYNPQP-HNKAVLL
  SEQ 4 (gD protein)  (200)   CWPAKPDRYSEILHEWCRNVKTIGLDGARDYHYYWVPYNPQP-HNKAVLL

                                251                                             300
         AAB67058 (gD)  (231)   DFYPLNGPEPPIKPKEALRYDIPYKVNDKFDDELPSRPHISNTINKTIKE
         AAK51062 (gD)  (231)   DFYRLNGREPPIKPKEALRYDIPYKVNDKFDDELPSRPHISNTINKTIKE
         CAC51465 (gD)  (233)   EFYRMNGRDPPVKPKEALRYDKPYRFPKKTEESQP-KPTEIKSKVSSEEE
         BAA44951 (gD)  (249)   YWYRTHGREPPVRPQEAIRYDRPAIPSGSEDSKRS----HDSRGESSGPN
  SEQ 4 (gD protein)  (249)   YWYRTHGREPPVRPQEAIRYDRPAIPSGSEDSKRS----HDSRGESSGPN

                                301                                             350
         AAB67058 (gD)  (281)   IVNLEDYFKNTRVIDTT------TPTPINNTPKNITVGIVIIILIILFII
         AAK51062 (gD)  (281)   IVNLEDYFKNTRVIDTT------TPTPINNTPKNITVGIVIIILIILFII
         CAC51465 (gD)  (282)   SKKLEEYLKISDVNLIDGN--IETQLPINNSKTNITIAVVTIIIIIILSI
         BAA44951 (gD)  (295)   WIDIRNYTPKNNVPIIISDDDVPTAPPKGMNNQSVVIPAIVLSCLIIALI
  SEQ 4 (gD protein)  (295)   WIDIRNYTPKNNVPIIISDDDVPTAPPKGMNNQSVVIPAIVLSCLIIALI
```

Figure 13B

```
                                351                           381
     AAB67058 (gD)   (325) GFFVYKRQKI----YNNYKKLTTNV------
     AAK51062 (gD)   (325) GFFVYKRQKI----YNNYKKLTTNV------
     CAC51465 (gD)   (330) TGFFIYRRRK----YNNYKRLPVNI------
     BAA44951 (gD)   (345) LGVIYYILRVKRSRSTAYQQLPIIHTTHHP-
SEQ 4 (gD protein)   (345) LGVIYYILRVKRSRSTAYQQLPIIHTTHHP-
```

| | SEQ ID NO:4 (gD protein)(sequence identity percentage) |
|---|---|
| AAB67058(gD)SEQ ID NO:19 | 39.4% |
| AAK51062(gD)SEQ ID NO:21 | 39.4% |
| CAC51465(gD)SEQ ID NO:23 | 37.9% |
| BAA44951(gD)SEQ ID NO:17 | 100% |

SEQUENCE LISTING

<160> NUMBER OF SEQ ID NOS: 27

<210> SEQ ID NO 1
<211> LENGTH: 948
<212> TYPE: PRT
<213> ORGANISM: artificial sequence
<220> FEATURE:
<223> OTHER INFORMATION: Feline HV gB protein

<400> SEQUENCE: 1

Met Ser Thr Arg Gly Asp Leu Gly Lys Arg Arg Arg Gly Ser Arg Trp
1 5 10 15

Gln Gly His Ser Gly Tyr Phe Arg Gln Arg Cys Phe Phe Pro Ser Leu
20 25 30

Leu Gly Ile Ala Ala Thr Gly Ser Arg His Gly Asn Gly Ser Ser Gly
35 40 45

Leu Thr Arg Leu Ala Arg Tyr Val Ser Phe Ile Trp Ile Val Leu Phe
50 55 60

Leu Val Gly Pro Arg Pro Val Glu Gly Gln Ser Gly Ser Thr Ser Glu
65 70 75 80

Gln Pro Arg Arg Thr Val Ala Thr Pro Glu Val Gly Gly Thr Pro Pro
85 90 95

Lys Pro Thr Thr Asp Pro Thr Asp Met Ser Asp Met Arg Glu Ala Leu
100 105 110

Arg Ala Ser Gln Ile Glu Ala Asn Gly Pro Ser Thr Phe Tyr Met Cys
115 120 125

Pro Pro Pro Ser Gly Ser Thr Val Val Arg Leu Glu Pro Pro Arg Ala
130 135 140

Cys Pro Asp Tyr Lys Leu Gly Lys Asn Phe Thr Glu Gly Ile Ala Val
145 150 155 160

Ile Phe Lys Glu Asn Ile Ala Pro Tyr Lys Phe Lys Ala Asn Ile Tyr
165 170 175

Tyr Lys Asn Ile Ile Met Thr Thr Val Trp Ser Gly Ser Ser Tyr Ala
180 185 190

Val Thr Thr Asn Arg Tyr Thr Asp Arg Val Pro Val Lys Val Gln Glu
195 200 205

Ile Thr Asp Leu Ile Asp Arg Arg Gly Met Cys Leu Ser Lys Ala Asp
210 215 220

Tyr Val Arg Asn Asn Tyr Gln Phe Thr Ala Phe Asp Arg Asp Glu Asp
225 230 235 240

Pro Arg Glu Leu Pro Leu Lys Pro Ser Lys Phe Asn Thr Pro Glu Ser
245 250 255

Arg Gly Trp His Thr Thr Asn Glu Thr Tyr Thr Lys Ile Gly Ala Ala
260 265 270

Gly Phe His His Ser Gly Thr Ser Val Asn Cys Ile Val Glu Glu Val
275 280 285

Asp Ala Arg Ser Val Tyr Pro Tyr Asp Ser Phe Ala Ile Ser Thr Gly
290 295 300

Asp Val Ile His Met Ser Pro Phe Phe Gly Leu Arg Asp Gly Ala His
305 310 315 320

Val Glu His Thr Ser Tyr Ser Ser Asp Arg Phe Gln Gln Ile Glu Gly
325 330 335

Tyr Tyr Pro Ile Asp Leu Asp Thr Arg Leu Gln Leu Gly Ala Pro Val

-continued

```
            340                 345                 350

Ser Arg Asn Phe Leu Glu Thr Pro His Val Thr Val Ala Trp Asn Trp
        355                 360                 365

Thr Pro Lys Ser Gly Arg Val Cys Thr Leu Ala Lys Trp Arg Glu Ile
    370                 375                 380

Asp Glu Met Leu Arg Asp Glu Tyr Gln Gly Ser Tyr Arg Phe Thr Ala
385                 390                 395                 400

Lys Thr Ile Ser Ala Thr Phe Ile Ser Asn Thr Ser Gln Phe Glu Ile
                405                 410                 415

Asn Arg Ile Arg Leu Gly Asp Cys Ala Thr Lys Glu Ala Ala Glu Ala
            420                 425                 430

Ile Asp Arg Ile Tyr Lys Ser Lys Tyr Ser Lys Thr His Ile Gln Thr
        435                 440                 445

Gly Thr Leu Glu Thr Tyr Leu Ala Arg Gly Gly Phe Leu Ile Ala Phe
    450                 455                 460

Arg Pro Met Ile Ser Asn Glu Leu Ala Lys Leu Tyr Ile Asn Glu Leu
465                 470                 475                 480

Ala Arg Ser Asn Arg Thr Val Asp Leu Ser Ala Leu Leu Asn Pro Ser
                485                 490                 495

Gly Glu Thr Val Gln Arg Thr Arg Arg Ser Val Pro Ser Asn Gln His
            500                 505                 510

His Arg Ser Arg Arg Ser Thr Ile Glu Gly Gly Ile Glu Thr Val Asn
        515                 520                 525

Asn Ala Ser Leu Leu Lys Thr Thr Ser Ser Val Glu Phe Ala Met Leu
    530                 535                 540

Gln Phe Ala Tyr Asp Tyr Ile Gln Ala His Val Asn Glu Met Leu Ser
545                 550                 555                 560

Arg Ile Ala Thr Ala Trp Cys Thr Leu Gln Asn Arg Glu His Val Leu
                565                 570                 575

Trp Thr Glu Thr Leu Lys Leu Asn Pro Gly Gly Val Val Ser Met Ala
            580                 585                 590

Leu Glu Arg Arg Val Ser Ala Arg Leu Leu Gly Asp Ala Val Ala Val
        595                 600                 605

Thr Gln Cys Val Asn Ile Ser Ser Gly His Val Tyr Ile Gln Asn Ser
    610                 615                 620

Met Arg Val Thr Gly Ser Ser Thr Thr Cys Tyr Ser Arg Pro Leu Val
625                 630                 635                 640

Ser Phe Arg Ala Leu Asn Asp Ser Glu Tyr Ile Glu Gly Gln Leu Gly
                645                 650                 655

Glu Asn Asn Glu Leu Leu Val Glu Arg Lys Leu Ile Glu Pro Cys Thr
            660                 665                 670

Val Asn Asn Lys Arg Tyr Phe Lys Phe Gly Ala Asp Tyr Val Tyr Phe
        675                 680                 685

Glu Asp Tyr Ala Tyr Val Arg Lys Val Pro Leu Ser Glu Ile Glu Leu
    690                 695                 700

Ile Ser Ala Tyr Val Asp Leu Asn Leu Thr Leu Leu Glu Asp Arg Glu
705                 710                 715                 720

Phe Leu Pro Leu Glu Val Tyr Thr Arg Ala Glu Leu Glu Asp Thr Gly
                725                 730                 735

Leu Leu Asp Tyr Ser Glu Ile Gln Arg Arg Asn Gln Leu His Ala Leu
            740                 745                 750

Lys Phe Tyr Asp Ile Asp Ser Ile Val Arg Val Asp Asn Asn Leu Val
        755                 760                 765
```

```
Ile Met Arg Gly Met Ala Asn Phe Phe Gln Gly Leu Gly Asp Val Gly
    770                 775                 780

Ala Gly Phe Gly Lys Val Val Leu Gly Ala Ala Ser Ala Val Ile Ser
785                 790                 795                 800

Thr Val Ser Gly Val Ser Ser Phe Leu Asn Asn Pro Phe Gly Ala Leu
                805                 810                 815

Ala Val Gly Leu Leu Ile Leu Ala Gly Ile Val Ala Ala Phe Leu Ala
            820                 825                 830

Tyr Arg Tyr Ile Ser Arg Leu Arg Ala Asn Pro Met Lys Ala Leu Tyr
        835                 840                 845

Pro Val Thr Thr Arg Asn Leu Lys Gln Thr Ala Lys Ser Pro Ala Ser
    850                 855                 860

Thr Ala Gly Gly Asp Ser Asp Pro Gly Val Asp Asp Phe Asp Glu Glu
865                 870                 875                 880

Lys Leu Met Gln Ala Arg Glu Met Ile Lys Tyr Met Ser Leu Val Ser
                885                 890                 895

Ala Met Glu Gln Gln Glu His Lys Ala Met Lys Lys Asn Lys Gly Pro
            900                 905                 910

Ala Ile Leu Thr Ser His Leu Thr Asn Met Ala Leu Arg Arg Arg Gly
        915                 920                 925

Pro Lys Tyr Gln Arg Leu Asn Asn Leu Asp Ser Gly Asp Asp Thr Glu
    930                 935                 940

Thr Asn Leu Val
945


<210> SEQ ID NO 2
<211> LENGTH: 2850
<212> TYPE: DNA
<213> ORGANISM: artificial sequence
<220> FEATURE:
<223> OTHER INFORMATION: codon-optimized FHV gB DNA

<400> SEQUENCE: 2

atgagcacaa gaggcgacct gggcaagaga aggcggggca gcagatggca gggccatagc     60

ggctacttca gacagagatg cttcttccca agcctgctgg gaatcgccgc caccggcagc    120

agacacggca atggcagcag cggcctgacc agactggcca gatacgtgtc cttcatctgg    180

atcgtgctgt tcctcgtggg ccctagacct gtggagggcc agagcggcag caccagcgag    240

cagcctagaa gaaccgtggc cacccctgaa gtgggcggca caccccccaa gcctaccacc    300

gaccccaccg acatgtccga catgagagag gccctgagag ccagccagat cgaggccaac    360

ggccccagca ccttctacat gtgcccccct cctagcggct ccaccgtcgt gagactggaa    420

ccccccagag cctgccccga ttacaagctg ggcaagaact tcaccgaggg cattgccgtg    480

atcttcaaag agaatatcgc cccctacaag ttcaaggcca acatctacta caagaacatc    540

atcatgacca ccgtgtggag cggcagctcc tacgccgtga ccaccaacag atacaccgac    600

agagtgcccg tgaaggtgca ggaaatcacc gacctgatcg acagacgggg catgtgcctg    660

agcaaggccg actacgtgcg gaacaactac cagttcaccg ccttcgaccg ggacgaggac    720

cctagagagc tgcccctgaa gcccagcaag ttcaacaccc ccgagagcag aggctggcac    780

accaccaacg agacatacac caagatcggc gctgccggct ttcaccacag cggcaccagc    840

gtgaactgca tcgtggagga agtggacgcc agaagcgtgt acccctacga cagcttcgcc    900

atcagcaccg gcgacgtgat ccacatgagc ccatttttcg gcctgagaga tggcgcccac    960
```

gtggagcaca ccagctacag cagcgacaga tttcagcaga tcgagggcta ctaccccatc 1020
gacctggaca ccagactgca gctgggagcc cccgtgtcca gaaacttcct ggaaaccccc 1080
cacgtgaccg tggcctggaa ctggaccccc aagagcggca gagtgtgcac cctggccaag 1140
tggcgggaga tcgacgagat gctgcgggac gagtaccagg gcagctacag attcaccgcc 1200
aagaccatca gcgccacctt catcagcaac accagccagt tcgagatcaa cagaatcaga 1260
ctgggcgact gcgccacaaa agaggccgcc gaggccatcg acagaatcta caagagcaag 1320
tacagcaaga cccacatcca gaccggcacc ctggaaacct atctggccag aggcggcttc 1380
ctgatcgcct tcagacccat gatcagcaac gagctggcca agctgtacat caatgagctg 1440
gccagatcca acagaaccgt ggacctgagc gccctgctga accctagcgg cgagacagtg 1500
cagagaacca ggcggagcgt gcccagcaac cagcaccaca gaagcagaag aagcaccatc 1560
gagggcggca tcgagacagt gaacaacgcc tccctgctga aaaccacctc cagcgtggag 1620
ttcgccatgc tgcagttcgc ctacgactac atccaggccc acgtgaatga gatgctgtcc 1680
agaatcgcca ccgcctggtg caccctgcag aaccgggagc acgtgctgtg gaccgagaca 1740
ctgaagctga acccaggcgg cgtggtgtcc atggccctgg aaagaagagt gtccgccaga 1800
ctgctgggag atgccgtggc cgtgacccag tgcgtgaaca tctccagcgg ccacgtgtac 1860
atccagaaca gcatgagagt gaccggcagc tccaccacct gctactccag acccctggtg 1920
tccttcagag ccctgaacga cagcgagtac atcgagggcc agctgggcga gaacaacgag 1980
ctgctggtcg agagaaagct gatcgagccc tgcaccgtga acaacaagag atacttcaag 2040
ttcggcgccg attacgtgta cttcgaggac tacgcctacg tgcgcaaggt gcccctgagc 2100
gagatcgagc tgatcagcgc ctacgtggat ctgaacctga ccctgctgga agatagagag 2160
ttcctgcccc tggaagtgta caccagagcc gaactggaag ataccggcct gctggactac 2220
agcgagatcc agagaagaaa ccagctgcac gccctgaagt tctacgacat cgacagcatc 2280
gtgcgggtgg acaacaacct ggtcatcatg agaggcatgg ccaacttttt ccagggcctg 2340
ggcgacgtgg gagccggctt tggcaaagtg gtgctgggag ccgccagcgc cgtgatcagc 2400
accgtgtccg gcgtgagcag cttcctgaac aaccccttcg gagccctggc cgtgggcctg 2460
ctgatcctgg ccggcatcgt ggccgccttt ctggcctaca gatacatcag cagactgaga 2520
gccaacccca tgaaggccct gtaccctgtg accaccagaa acctgaagca gaccgccaag 2580
agccctgcct ctaccgctgg cggcgatagc gaccccggcg tggacgactt cgacgaggaa 2640
aagctgatgc aggccagaga aatgatcaag tacatgagcc tggtgtccgc catggaacag 2700
caggaacaca aggccatgaa gaagaacaag ggccctgcca tcctgaccag ccacctgacc 2760
aacatggccc tgcggagaag aggccccaag taccagagac tgaacaacct ggacagcggc 2820
gacgacaccg agacaaacct ggtgtaatga 2850

<210> SEQ ID NO 3
<211> LENGTH: 2847
<212> TYPE: DNA
<213> ORGANISM: artificial sequence
<220> FEATURE:
<223> OTHER INFORMATION: wild-type FHV gB DNA FJ478159 encoding AAB28559

<400> SEQUENCE: 3
atgtccactc gtggcgatct tgggaagcgg cgacgaggga gtcgttggca gggacacagt 60
ggctattttc gacagagatg ttttttccct tctctactcg gtattgcagc gactggctcc 120
agacatggta acggatcgtc gggattaacc agactagcta gatatgtttc atttatctgg 180

-continued

```
atcgtactat tcttagtcgg tccccgtcca gtagagggtc aatctggaag cacatcggaa    240
caaccccggc ggactgtagc taccccctgag gtagggggta caccaccaaa accaactaca    300
gatcccaccg atatgtcgga tatgagggaa gctctccgtg cgtcccaaat agaggctaac    360
ggaccatcga ctttttatat gtgtccacca ccttcaggat ctactgtcgt gcgtttagag    420
ccaccacggg cctgtccaga ttataaacta gggaaaaatt ttaccgaggg tatagctgta    480
atatttaaag aaaatatagc gccatataaa ttcaaggcaa atatatacta taaaaacatt    540
attatgacaa cggtatggtc tgggagttcc tatgccgtta caaccaaccg atatacagac    600
agggttcccg tgaaagttca agagattaca gatctcatag atagacgggg tatgtgcctc    660
tcgaaagctg attacgttcg taacaattat caatttacgg cctttgatcg agacgaggat    720
cccagagaac tgcctctgaa accctccaag ttcaacactc cagagtcccg tggatggcac    780
accaccaatg aaacatacac aaagatcggt gctgctggat ttcaccactc tgggacctct    840
gtaaattgca tcgtagagga agtggatgca agatctgtat atccatatga ctcatttgct    900
atctccactg gtgacgtgat tcacatgtct ccattctttg ggctgaggga tggagcccat    960
gtagaacata ctagttattc ttcagacaga tttcaacaaa tcgagggata ctatccaata   1020
gacttggata cgcgattaca actgggggca ccagtttctc gcaatttttt ggaaactccg   1080
catgtgacag tggcctggaa ctggacccca aagtgtggtc gggtatgtac cttagccaaa   1140
tggagggaaa tagatgaaat gctacgcgat gaatatcagg gctcctatag atttacagtc   1200
aagaccatat ccgctacttt catctccaat acttcacaat ttgaaatcaa tcgtatccgt   1260
ttgggggact gtgccaccaa ggaggcagcc gaagccatag accggattta taagagtaaa   1320
tatagtaaaa ctcatattca gactggaacc ctggagacct acctagcccg tggcggattt   1380
ctaatagctt tccgtcccat gatcagcaac gaactagcaa agttatatat caatgaatta   1440
gcacgttcca atcgcacggt agatctcagt gcactcctca atccatctgg ggaaacagta   1500
caacgaacta gaagatcggt cccatctaat caacatcata ggtcgcggcg cagcacaata   1560
gagggggggta tagaaaccgt gaacaatgca tcactcctca agaccacctc atctgtggaa   1620
ttcgcaatgc tacaatttgc ctatgactac atacaagccc atgtaaatga aatgttgagt   1680
cggatagcca ctgcctggtg tacacttcag aaccgcgaac atgtgctgtg gacagagacc   1740
ctaaaactca atcccggtgg ggtggtctcg atggccctag aacgtcgtgt atccgcgcgc   1800
ctacttggag atgccgtcgc cgtaacacaa tgtgttaaca tttctagcgg acatgtctat   1860
atccaaaatt ctatgcgggt gacgggttca tcaacgacat gttacagccg ccctcttgtt   1920
tccttccgtg ccctcaatga ctccgaatac atagaaggac aactagggga aaacaatgac   1980
cttctcgtgg aacgaaaact aattgagcct tgcactgtca ataataagcg gtattttaag   2040
tttggggcag attatgtata ttttgaggat tatgcgtatg tccgtaaagt cccgctatcg   2100
gagatagaac tgataagtgc gtatgtggat ttaaatctta ctctcctaga ggatcgtgaa   2160
tttctcccac tcgaagttta tacacgagct gagctggaag ataccggcct tttggactac   2220
agcgagattc aacggcgcaa ccaactccac gccttaaaat tttatgatat agacagcata   2280
gtcagagtgg ataataatct tgtcatcatg cgtggtatgg caaatttttt tcagggactc   2340
ggggatgtgg gggctggttt cggcaaggtg gtcttagggg ctgcgagtgc ggtaatctca   2400
acagtatcag gcgtatcatc atttctaaac aacccatttg gagcattggc cgtgggactg   2460
ttaatattag ctggcatcgt cgcagcattc ctggcatatc gctatatatc tagattacgt   2520
```

gcaaatccaa tgaaagcctt atatcctgtg acgactagga atttgaaaca gacggctaag 2580
agccccgcct caacggctgg tggggatagc gacccgggag tcgatgactt cgatgaggaa 2640
aagctaatgc aggcaaggga gatgataaaa tatatgtccc tcgtatcggc tatggagcaa 2700
caagaacata aggcgatgaa aaagaataag ggcccagcga tcctaacgag tcatctcact 2760
aacatggccc tccgtcgccg tggacctaaa taccaacgcc tcaataatct tgatagcggt 2820
gatgatactg aaacaaatct tgtctaa 2847

<210> SEQ ID NO 4
<211> LENGTH: 374
<212> TYPE: PRT
<213> ORGANISM: artificial sequence
<220> FEATURE:
<223> OTHER INFORMATION: Feline HV gD protein

<400> SEQUENCE: 4

Met Met Thr Arg Leu His Phe Trp Trp Cys Gly Ile Phe Ala Val Leu
1 5 10 15

Lys Tyr Leu Val Cys Thr Ser Ser Leu Thr Thr Thr Pro Lys Thr Thr
20 25 30

Thr Val Tyr Val Lys Gly Phe Asn Ile Pro Pro Leu Arg Tyr Asn Tyr
35 40 45

Thr Gln Ala Arg Ile Val Pro Lys Ile Pro Gln Ala Met Asp Pro Lys
50 55 60

Ile Thr Ala Glu Val Arg Tyr Val Thr Ser Met Asp Ser Cys Gly Met
65 70 75 80

Val Ala Leu Ile Ser Glu Pro Asp Ile Asp Ala Thr Ile Arg Thr Ile
85 90 95

Gln Leu Ser Gln Lys Lys Thr Tyr Asn Ala Thr Ile Ser Trp Phe Lys
100 105 110

Val Thr Gln Gly Cys Glu Tyr Pro Met Phe Leu Met Asp Met Arg Leu
115 120 125

Cys Asp Pro Lys Arg Glu Phe Gly Ile Cys Ala Leu Arg Ser Pro Ser
130 135 140

Tyr Trp Leu Glu Pro Leu Thr Lys Tyr Met Phe Leu Thr Asp Asp Glu
145 150 155 160

Leu Gly Leu Ile Met Met Ala Pro Ala Gln Phe Asn Gln Gly Gln Tyr
165 170 175

Arg Arg Val Ile Thr Ile Asp Gly Ser Met Phe Tyr Thr Asp Phe Met
180 185 190

Val Gln Leu Ser Pro Thr Pro Cys Trp Phe Ala Lys Pro Asp Arg Tyr
195 200 205

Glu Glu Ile Leu His Glu Trp Cys Arg Asn Val Lys Thr Ile Gly Leu
210 215 220

Asp Gly Ala Arg Asp Tyr His Tyr Tyr Trp Val Pro Tyr Asn Pro Gln
225 230 235 240

Pro His His Lys Ala Val Leu Leu Tyr Trp Tyr Arg Thr His Gly Arg
245 250 255

Glu Pro Pro Val Arg Phe Gln Glu Ala Ile Arg Tyr Asp Arg Pro Ala
260 265 270

Ile Pro Ser Gly Ser Glu Asp Ser Lys Arg Ser Asn Asp Ser Arg Gly
275 280 285

Glu Ser Ser Gly Pro Asn Trp Ile Asp Ile Glu Asn Tyr Thr Pro Lys
290 295 300

-continued

```
Asn Asn Val Pro Ile Ile Ile Ser Asp Asp Asp Val Pro Thr Ala Pro
305                 310                 315                 320

Pro Lys Gly Met Asn Asn Gln Ser Val Val Ile Pro Ala Ile Val Leu
                325                 330                 335

Ser Cys Leu Ile Ile Ala Leu Ile Leu Gly Val Ile Tyr Tyr Ile Leu
            340                 345                 350

Arg Val Lys Arg Ser Arg Ser Thr Ala Tyr Gln Gln Leu Pro Ile Ile
        355                 360                 365

His Thr Thr His His Pro
    370
```

<210> SEQ ID NO 5
<211> LENGTH: 1128
<212> TYPE: DNA
<213> ORGANISM: artificial sequence
<220> FEATURE:
<223> OTHER INFORMATION: codon-optimized FHV gD DNA

<400> SEQUENCE: 5

```
atgatgacca ggctgcactt ctggtggtgc ggcatcttcg ccgtgctgaa gtacctggtc     60

tgcaccagca gcctgaccac cacccccaag acaaccaccg tgtacgtgaa gggcttcaac    120

atcccccccc tgaggtacaa ctacacccag gccaggatcg tgcccaagat cccccaggcc    180

atggacccta agatcaccgc cgaagtgcgc tacgtgacca gcatggacag ctgcggcatg    240

gtggccctga tcagcgagcc tgacatcgac gccaccatca ggaccatcca gctgtcccag    300

aagaaaacct acaacgccac aatcagctgg ttcaaagtga cccagggctg cgagtacccc    360

atgttcctga tggacatgag gctgtgcgac cccaagagag agttcggcat ctgcgccctg    420

agaagcccca gctactggct ggaacccctg accaagtaca tgtttctgac cgacgacgag    480

ctgggcctga tcatgatggc ccctgcccag ttcaaccagg gccagtacag aagagtgatc    540

accatcgacg gcagcatgtt ctacaccgac ttcatggtgc agctgtcccc cacccccctgt    600

tggttcgcca agcccgacag atacgaggaa atcctgcacg agtggtgtag gaacgtgaaa    660

accatcggcc tggacggcgc cagggactac cactactact gggtgcccta caacccccag    720

cctcaccaca aggccgtgct gctgtactgg tacaggaccc acggcagaga gccccccgtc    780

aggttccagg aagccatcag atacgacagg cccgccatcc ctagcggcag cgaggacagc    840

aagagaagca acgacagcag gggcgagtct agcggcccca actggatcga catcgagaac    900

tacaccccta agaacaacgt gcccatcatc atcagcgacg acgacgtgcc taccgcccct    960

cccaagggca tgaacaacca gagcgtggtc atccccgcca tcgtgctgtc ctgcctgatc   1020

attgccctga tcctgggcgt gatctactac atcctgagag tgaagagaag cagaagcacc   1080

gcctaccagc agctgcctat catccacacc acccaccacc cctaatga                1128
```

<210> SEQ ID NO 6
<211> LENGTH: 1125
<212> TYPE: DNA
<213> ORGANISM: artificial sequence
<220> FEATURE:
<223> OTHER INFORMATION: wild-type FHV gD DNA FJ478159

<400> SEQUENCE: 6

```
atgatgacac gtctacattt ttggtggtgt ggaatctttg cggtcctgaa atatctggta     60

tgtacttcaa gccttacgac cacgccaaaa acaactacgg tttatgtgaa gggatttaat    120

atacctccac tacgctacaa ttatactcaa gccagaatcg tgccaaaaat tccccaggcg    180
```

```
atggatccga agataacagc tgaagtacgt tatgtaacat caatggattc atgtgggatg    240

gtggcattga tatcagagcc ggatatagac gctactattc gaaccataca actatctcaa    300

aaaaaaacat ataacgcgac tataagttgg tttaaggtaa cccagggttg tgaataccct    360

atgtttctta tggatatgag actttgtgat cctaaacggg aatttggaat atgtgcttta    420

cggtcgcctt catattggtt ggaaccttta acaaagtata tgttcctaac agacgatgaa    480

ctgggtttga ttatgatggc ccggcccaa tttaatcaag gacaatatcg aagagttata    540

accatcgatg gttccatgtt ttatacagat tttatggtac aactatctcc aacgccatgt    600

tggttcgcaa aacccgatag atacgaagag attctacatg aatggtgtcg aaatgttaaa    660

actattggcc ttgatggagc tcgtgattac cactattatt gggtacccta taacccacaa    720

cctcaccata aagccgtact cttatattgg tatcggactc atggccgaga acccccagta    780

agattccaag aggccattcg atatgatcgt cccgccatac cgtctgggag tgaggattcg    840

aaacggtcca acgactctag aggagaatcg agtggaccca attggataga cattgaaaat    900

tacactccta aaaataatgt gcctattata atatctgacg atgacgttcc tacagcccct    960

cccaagggca tgaataatca gtcagtagtg atacccgcaa tcgtactaag ttgtcttata   1020

atagcactga ttctaggagt gatatattat attttgaggg taaagaggtc tcgatcaact   1080

gcatatcaac aacttcctat aatacataca actcaccatc cttaa                   1125
```

```
<210> SEQ ID NO 7
<211> LENGTH: 948
<212> TYPE: PRT
<213> ORGANISM: artificial sequence
<220> FEATURE:
<223> OTHER INFORMATION: gB protein (1911192A)

<400> SEQUENCE: 7

Met Ser Thr Arg Gly Asp Leu Gly Lys Arg Arg Arg Gly Ser Arg Trp
1               5                   10                  15

Gln Gly His Ser Gly Tyr Pro Arg Gln Arg Cys Phe Phe Pro Ser Leu
            20                  25                  30

Leu Gly Ile Ala Ala Thr Gly Ser Arg His Gly Asn Gly Ser Ser Gly
        35                  40                  45

Leu Thr Arg Leu Ala Arg Tyr Val Ser Phe Ile Trp Ile Val Leu Phe
    50                  55                  60

Leu Val Gly Pro Arg Pro Val Glu Gly Gln Ser Gly Ser Thr Ser Glu
65                  70                  75                  80

Gln Pro Arg Arg Thr Val Ala Thr Pro Glu Val Gly Gly Thr Pro Pro
                85                  90                  95

Lys Pro Thr Thr Asp Pro Thr Asp Met Ser Asp Met Arg Glu Ala Leu
            100                 105                 110

Arg Ala Ser Gln Ile Glu Ala Asn Gly Pro Ser Thr Phe Tyr Met Cys
        115                 120                 125

Pro Pro Pro Ser Gly Ser Thr Val Val Arg Leu Glu Pro Pro Arg Ala
    130                 135                 140

Cys Pro Asp Tyr Lys Leu Gly Lys Asn Phe Thr Glu Gly Ile Ala Val
145                 150                 155                 160

Ile Phe Lys Glu Asn Ile Ala Pro Tyr Lys Phe Lys Ala Asn Ile Tyr
                165                 170                 175

Tyr Lys Asn Ile Ile Met Thr Thr Val Trp Ser Gly Ser Ser Tyr Ala
            180                 185                 190

Val Thr Thr Asn Arg Tyr Thr Asp Arg Val Pro Val Lys Val Gln Glu
```

-continued

```
        195                 200                 205

Ile Thr Asp Leu Ile Asp Arg Arg Gly Met Cys Leu Ser Lys Ala Asp
    210                 215                 220

Tyr Val Arg Asn Asn Tyr Gln Phe Thr Ala Phe Asp Arg Asp Glu Asp
225                 230                 235                 240

Pro Arg Glu Leu Pro Leu Lys Pro Ser Lys Phe Asn Thr Pro Gln Ser
                245                 250                 255

Arg Gly Trp His Thr Thr Asn Glu Thr Tyr Thr Lys Ile Gly Ala Ala
            260                 265                 270

Gly Phe His His Ser Gly Thr Ser Val Asn Cys Ile Val Glu Glu Val
        275                 280                 285

Asp Ala Arg Ser Val Tyr Pro Tyr Asp Ser Phe Ala Ile Ser Thr Gly
    290                 295                 300

Asp Val Ile His Met Ser Pro Phe Phe Gly Leu Arg Asp Gly Ala His
305                 310                 315                 320

Val Glu His Thr Ser Tyr Ser Ser Asp Arg Phe Gln Gln Ile Glu Gly
                325                 330                 335

Tyr Tyr Pro Ile Asp Leu Asp Thr Arg Leu Gln Leu Gly Ala Pro Val
            340                 345                 350

Ser Arg Asn Phe Leu Glu Thr Pro His Val Thr Val Ala Trp Asn Trp
        355                 360                 365

Thr Pro Lys Cys Gly Arg Val Cys Thr Leu Ala Lys Trp Arg Glu Ile
    370                 375                 380

Asp Glu Met Leu Arg Asp Glu Tyr Gln Gly Ser Tyr Arg Phe Thr Val
385                 390                 395                 400

Lys Thr Ile Ser Ala Thr Phe Ile Ser Asn Thr Ser Gln Phe Glu Ile
                405                 410                 415

Asn Arg Ile Arg Leu Gly Asp Cys Ala Thr Lys Glu Ala Ala Glu Ala
            420                 425                 430

Ile Asp Arg Ile Tyr Lys Ser Lys Tyr Ser Lys Thr His Ile Gln Thr
        435                 440                 445

Gly Thr Leu Glu Thr Tyr Leu Ala Arg Gly Gly Phe Leu Ile Ala Phe
    450                 455                 460

Arg Pro Met Ile Ser Asn Glu Leu Ala Lys Leu Tyr Ile Asn Glu Leu
465                 470                 475                 480

Ala Arg Ser Asn Arg Thr Val Asp Leu Ser Ala Leu Leu Asn Pro Ser
                485                 490                 495

Gly Glu Thr Val Gln Arg Thr Arg Gly Ser Val Pro Ser Asn Gln His
            500                 505                 510

His Arg Ser Arg Arg Ser Thr Ile Glu Gly Gly Ile Glu Thr Val Asn
        515                 520                 525

Asn Ala Ser Leu Leu Lys Thr Thr Ser Ser Val Glu Phe Ala Met Ile
    530                 535                 540

Gln Phe Ala Tyr Asp Tyr Ile Gln Ala His Val Asn Glu Met Leu Ser
545                 550                 555                 560

Arg Ile Ala Thr Ala Trp Cys Thr Leu Gln Asn Arg Glu His Val Leu
                565                 570                 575

Trp Thr Glu Thr Leu Lys Leu Asn Pro Gly Gly Val Val Ser Met Ala
            580                 585                 590

Leu Glu Arg Arg Val Ser Ala Arg Leu Leu Gly Asp Ala Val Ala Val
        595                 600                 605

Thr Gln Cys Val Asn Ile Ser Ser Gly His Val Tyr Ile Gln Asn Ser
    610                 615                 620
```

Met Arg Val Thr Gly Ser Ser Thr Thr Cys Tyr Ser Arg Pro Leu Val
625 630 635 640

Ser Phe Arg Ala Leu Asn Asp Ser Glu Tyr Ile Glu Gly Gln Leu Gly
645 650 655

Glu Asn Asn Asp Leu Leu Val Glu Arg Lys Leu Ile Glu Pro Cys Thr
660 665 670

Val Asn Asn Lys Arg Tyr Phe Lys Phe Gly Ala Asp Tyr Val Tyr Phe
675 680 685

Glu Asp Tyr Ala Tyr Val Arg Lys Val Pro Leu Ser Glu Ile Glu Leu
690 695 700

Ile Ser Ala Tyr Val Asp Leu Asn Leu Thr Leu Leu Glu Asp Arg Glu
705 710 715 720

Phe Leu Pro Leu Glu Val Tyr Thr Arg Ala Glu Leu Glu Asp Thr Gly
725 730 735

Leu Leu Asp Tyr Ser Glu Ile Gln Arg Arg Asn Gln Leu His Ala Leu
740 745 750

Lys Phe Tyr Asp Ile Asp Ser Ile Val Arg Val Asp Asn Asn Leu Val
755 760 765

Ile Met Arg Gly Met Ala Asn Phe Phe Gln Gly Leu Gly Asp Val Gly
770 775 780

Ala Gly Phe Gly Lys Val Val Leu Gly Ala Ala Ser Ala Val Ile Ser
785 790 795 800

Thr Val Ser Gly Val Ser Ser Phe Leu Asn Asn Pro Phe Gly Ala Leu
805 810 815

Ala Val Gly Leu Leu Ile Leu Ala Gly Ile Val Ala Ala Phe Leu Ala
820 825 830

Tyr Arg Tyr Ile Ser Arg Leu Arg Ala Asn Pro Met Lys Ala Leu Tyr
835 840 845

Pro Val Thr Thr Arg Asn Leu Lys Gln Thr Ala Lys Ser Pro Ala Ser
850 855 860

Thr Ala Gly Gly Asp Ser Asp Pro Gly Val Asp Asp Phe Asp Glu Glu
865 870 875 880

Lys Leu Met Gln Ala Arg Glu Met Ile Lys Tyr Met Ser Leu Val Ser
885 890 895

Ala Met Glu Gln Gln Glu His Lys Ala Met Lys Lys Asn Lys Gly Pro
900 905 910

Ala Ile Leu Thr Ser His Leu Thr Asn Met Ala Leu Arg Arg Arg Gly
915 920 925

Pro Lys Tyr Gln Arg Leu Asn Asn Leu Asp Ser Gly Asp Asp Thr Glu
930 935 940

Thr Asn Leu Val
945

<210> SEQ ID NO 8
<211> LENGTH: 948
<212> TYPE: PRT
<213> ORGANISM: artificial sequence
<220> FEATURE:
<223> OTHER INFORMATION: gB protein (AAB28559)

<400> SEQUENCE: 8

Met Ser Thr Arg Gly Asp Leu Gly Lys Arg Arg Arg Gly Ser Arg Trp
1 5 10 15

Gln Gly His Ser Gly Tyr Phe Arg Gln Arg Cys Phe Phe Pro Ser Leu
20 25 30

-continued

```
Leu Gly Ile Ala Ala Thr Gly Ser Arg His Gly Asn Gly Ser Ser Gly
        35                  40                  45

Leu Thr Arg Leu Ala Arg Tyr Val Ser Phe Ile Trp Ile Val Leu Phe
    50                  55                  60

Leu Val Gly Pro Arg Pro Val Glu Gly Gln Ser Gly Ser Thr Ser Glu
65                  70                  75                  80

Gln Pro Arg Arg Thr Val Ala Thr Pro Glu Val Gly Gly Thr Pro Pro
                85                  90                  95

Lys Pro Thr Thr Asp Pro Thr Asp Met Ser Asp Met Arg Glu Ala Leu
            100                 105                 110

Arg Ala Ser Gln Ile Glu Ala Asn Gly Pro Ser Thr Phe Tyr Met Cys
        115                 120                 125

Pro Pro Pro Ser Gly Ser Thr Val Val Arg Leu Glu Pro Pro Arg Ala
    130                 135                 140

Cys Pro Asp Tyr Lys Leu Gly Lys Asn Phe Thr Glu Gly Ile Ala Val
145                 150                 155                 160

Ile Phe Lys Glu Asn Ile Ala Pro Tyr Lys Phe Lys Ala Asn Ile Tyr
                165                 170                 175

Tyr Lys Asn Ile Ile Met Thr Thr Val Trp Ser Gly Ser Ser Tyr Ala
            180                 185                 190

Val Thr Thr Asn Arg Tyr Thr Asp Arg Val Pro Val Lys Val Gln Glu
        195                 200                 205

Ile Thr Asp Leu Ile Asp Arg Arg Gly Met Cys Leu Ser Lys Ala Asp
    210                 215                 220

Tyr Val Arg Asn Asn Tyr Gln Phe Thr Ala Phe Asp Arg Asp Glu Asp
225                 230                 235                 240

Pro Arg Glu Leu Pro Leu Lys Pro Ser Lys Phe Asn Thr Pro Glu Ser
                245                 250                 255

Arg Gly Trp His Thr Thr Asn Glu Thr Tyr Thr Lys Ile Gly Ala Ala
            260                 265                 270

Gly Phe His His Ser Gly Thr Ser Val Asn Cys Ile Val Glu Glu Val
        275                 280                 285

Asp Ala Arg Ser Val Tyr Pro Tyr Asp Ser Phe Ala Ile Ser Thr Gly
    290                 295                 300

Asp Val Ile His Met Ser Pro Phe Phe Gly Leu Arg Asp Gly Ala His
305                 310                 315                 320

Val Glu His Thr Ser Tyr Ser Ser Asp Arg Phe Gln Gln Ile Glu Gly
                325                 330                 335

Tyr Tyr Pro Ile Asp Leu Asp Thr Arg Leu Gln Leu Gly Ala Pro Val
            340                 345                 350

Ser Arg Asn Phe Leu Glu Thr Pro His Val Thr Val Ala Trp Asn Trp
        355                 360                 365

Thr Pro Lys Ser Gly Arg Val Cys Thr Leu Ala Lys Trp Arg Glu Ile
    370                 375                 380

Asp Glu Met Leu Arg Asp Glu Tyr Gln Gly Ser Tyr Arg Phe Thr Ala
385                 390                 395                 400

Lys Thr Ile Ser Ala Thr Phe Ile Ser Asn Thr Ser Gln Phe Glu Ile
                405                 410                 415

Asn Arg Ile Arg Leu Gly Asp Cys Ala Thr Lys Glu Ala Ala Glu Ala
            420                 425                 430

Ile Asp Arg Ile Tyr Lys Ser Lys Tyr Ser Lys Thr His Ile Gln Thr
        435                 440                 445
```

-continued

```
Gly Thr Leu Glu Thr Tyr Leu Ala Arg Gly Gly Phe Leu Ile Ala Phe
    450                 455                 460

Arg Pro Met Ile Ser Asn Glu Leu Ala Lys Leu Tyr Ile Asn Glu Leu
465                 470                 475                 480

Ala Arg Ser Asn Arg Thr Val Asp Leu Ser Ala Leu Leu Asn Pro Ser
                485                 490                 495

Gly Glu Thr Val Gln Arg Thr Arg Arg Ser Val Pro Ser Asn Gln His
            500                 505                 510

His Arg Ser Arg Arg Ser Thr Ile Glu Gly Gly Ile Glu Thr Val Asn
        515                 520                 525

Asn Ala Ser Leu Leu Lys Thr Thr Ser Ser Val Glu Phe Ala Met Leu
    530                 535                 540

Gln Phe Ala Tyr Asp Tyr Ile Gln Ala His Val Asn Glu Met Leu Ser
545                 550                 555                 560

Arg Ile Ala Thr Ala Trp Cys Thr Leu Gln Asn Arg Glu His Val Leu
                565                 570                 575

Trp Thr Glu Thr Leu Lys Leu Asn Pro Gly Gly Val Val Ser Met Ala
            580                 585                 590

Leu Glu Arg Arg Val Ser Ala Arg Leu Leu Gly Asp Ala Val Ala Val
        595                 600                 605

Thr Gln Cys Val Asn Ile Ser Ser Gly His Val Tyr Ile Gln Asn Ser
    610                 615                 620

Met Arg Val Thr Gly Ser Ser Thr Thr Cys Tyr Ser Arg Pro Leu Val
625                 630                 635                 640

Ser Phe Arg Ala Leu Asn Asp Ser Glu Tyr Ile Glu Gly Gln Leu Gly
                645                 650                 655

Glu Asn Asn Glu Leu Leu Val Glu Arg Lys Leu Ile Glu Pro Cys Thr
            660                 665                 670

Val Asn Asn Lys Arg Tyr Phe Lys Phe Gly Ala Asp Tyr Val Tyr Phe
        675                 680                 685

Glu Asp Tyr Ala Tyr Val Arg Lys Val Pro Leu Ser Glu Ile Glu Leu
    690                 695                 700

Ile Ser Ala Tyr Val Asp Leu Asn Leu Thr Leu Leu Glu Asp Arg Glu
705                 710                 715                 720

Phe Leu Pro Leu Glu Val Tyr Thr Arg Ala Glu Leu Glu Asp Thr Gly
                725                 730                 735

Leu Leu Asp Tyr Ser Glu Ile Gln Arg Arg Asn Gln Leu His Ala Leu
            740                 745                 750

Lys Phe Tyr Asp Ile Asp Ser Ile Val Arg Val Asp Asn Asn Leu Val
        755                 760                 765

Ile Met Arg Gly Met Ala Asn Phe Phe Gln Gly Leu Gly Asp Val Gly
    770                 775                 780

Ala Gly Phe Gly Lys Val Val Leu Gly Ala Ala Ser Ala Val Ile Ser
785                 790                 795                 800

Thr Val Ser Gly Val Ser Ser Phe Leu Asn Asn Pro Phe Gly Ala Leu
                805                 810                 815

Ala Val Gly Leu Leu Ile Leu Ala Gly Ile Val Ala Ala Phe Leu Ala
            820                 825                 830

Tyr Arg Tyr Ile Ser Arg Leu Arg Ala Asn Pro Met Lys Ala Leu Tyr
        835                 840                 845

Pro Val Thr Thr Arg Asn Leu Lys Gln Thr Ala Lys Ser Pro Ala Ser
    850                 855                 860

Thr Ala Gly Gly Asp Ser Asp Pro Gly Val Asp Asp Phe Asp Glu Glu
```

-continued 865 870 875 880

Lys Leu Met Gln Ala Arg Glu Met Ile Lys Tyr Met Ser Leu Val Ser
885 890 895

Ala Met Glu Gln Gln Glu His Lys Ala Met Lys Lys Asn Lys Gly Pro
900 905 910

Ala Ile Leu Thr Ser His Leu Thr Asn Met Ala Leu Arg Arg Arg Gly
915 920 925

Pro Lys Tyr Gln Arg Leu Asn Asn Leu Asp Ser Gly Asp Asp Thr Glu
930 935 940

Thr Asn Leu Val
945

<210> SEQ ID NO 9
<211> LENGTH: 948
<212> TYPE: PRT
<213> ORGANISM: artificial sequence
<220> FEATURE:
<223> OTHER INFORMATION: gB protein (AAB24381)

<400> SEQUENCE: 9

Met Ser Thr Arg Gly Asp Leu Gly Lys Arg Arg Arg Gly Ser Arg Trp
1 5 10 15

Gln Gly His Ser Gly Tyr Phe Arg Gln Arg Cys Phe Phe Pro Ser Leu
20 25 30

Leu Gly Ile Ala Ala Thr Gly Ser Arg His Gly Asn Gly Ser Ser Gly
35 40 45

Leu Thr Arg Leu Ala Arg Tyr Val Ser Phe Ile Trp Ile Val Leu Phe
50 55 60

Leu Val Gly Pro Arg Pro Val Glu Gly Gln Ser Gly Ser Thr Ser Glu
65 70 75 80

Gln Pro Arg Arg Thr Val Ala Thr Pro Glu Val Gly Gly Thr Pro Pro
85 90 95

Lys Pro Thr Thr Asp Pro Thr Asp Met Ser Asp Met Arg Glu Ala Leu
100 105 110

Arg Ala Ser Gln Ile Glu Ala Asn Gly Pro Ser Thr Phe Tyr Met Cys
115 120 125

Pro Pro Pro Ser Gly Ser Thr Val Val Arg Leu Glu Pro Pro Arg Ala
130 135 140

Cys Pro Asp Tyr Lys Leu Gly Lys Asn Phe Thr Glu Gly Ile Ala Val
145 150 155 160

Ile Phe Lys Glu Asn Ile Ala Pro Tyr Lys Phe Lys Ala Asn Ile Tyr
165 170 175

Tyr Lys Asn Ile Ile Met Thr Thr Val Trp Ser Gly Ser Ser Tyr Ala
180 185 190

Val Thr Thr Asn Arg Tyr Thr Asp Arg Val Pro Val Lys Val Gln Glu
195 200 205

Ile Thr Asp Leu Ile Asp Arg Arg Gly Met Cys Leu Ser Lys Ala Asp
210 215 220

Tyr Val Arg Asn Asn Tyr Gln Phe Thr Ala Phe Asp Arg Asp Glu Asp
225 230 235 240

Pro Arg Glu Leu Pro Leu Lys Pro Ser Lys Phe Asn Thr Pro Glu Ser
245 250 255

Arg Gly Trp His Thr Thr Asn Glu Thr Tyr Thr Lys Ile Gly Ala Ala
260 265 270

Gly Phe His His Ser Gly Thr Ser Val Asn Cys Ile Val Glu Glu Val

-continued

```
        275                 280                 285

Asp Ala Arg Ser Val Tyr Pro Tyr Asp Ser Phe Ala Ile Ser Thr Gly
    290                 295                 300

Asp Val Ile His Met Ser Pro Phe Phe Gly Leu Arg Asp Gly Ala His
305                 310                 315                 320

Val Glu His Thr Ser Tyr Ser Ser Asp Arg Phe Gln Gln Ile Glu Gly
                325                 330                 335

Tyr Tyr Pro Ile Asp Leu Asp Thr Arg Leu Gln Leu Gly Ala Pro Val
            340                 345                 350

Ser Arg Asn Phe Leu Glu Thr Pro His Val Thr Val Ala Trp Asn Trp
        355                 360                 365

Thr Pro Lys Cys Gly Arg Val Cys Thr Leu Ala Lys Trp Arg Glu Ile
    370                 375                 380

Asp Glu Met Leu Arg Asp Glu Tyr Gln Gly Ser Tyr Arg Phe Thr Val
385                 390                 395                 400

Lys Thr Ile Ser Ala Thr Phe Ile Ser Asn Thr Ser Gln Phe Glu Ile
                405                 410                 415

Asn Arg Ile Arg Leu Gly Asp Cys Ala Thr Lys Glu Ala Ala Glu Ala
            420                 425                 430

Ile Asp Arg Ile Tyr Lys Ser Lys Tyr Ser Lys Thr His Ile Gln Thr
        435                 440                 445

Gly Thr Leu Glu Thr Tyr Leu Ala Arg Gly Gly Phe Leu Ile Ala Phe
    450                 455                 460

Arg Pro Met Ile Ser Asn Glu Leu Ala Lys Leu Tyr Ile Asn Glu Leu
465                 470                 475                 480

Ala Arg Ser Asn Arg Thr Val Asp Leu Ser Ala Leu Leu Asn Pro Ser
                485                 490                 495

Gly Glu Thr Val Gln Arg Thr Arg Arg Ser Val Pro Ser Asn Gln His
            500                 505                 510

His Arg Ser Arg Arg Ser Thr Ile Glu Gly Gly Ile Glu Thr Val Asn
        515                 520                 525

Asn Ala Ser Leu Leu Lys Thr Thr Ser Ser Val Glu Phe Ala Met Leu
    530                 535                 540

Gln Phe Ala Tyr Asp Tyr Ile Gln Ala His Val Asn Glu Met Leu Ser
545                 550                 555                 560

Arg Ile Ala Thr Ala Trp Cys Thr Leu Gln Asn Arg Glu His Val Leu
                565                 570                 575

Trp Thr Glu Thr Leu Lys Leu Asn Pro Gly Gly Val Val Ser Met Ala
            580                 585                 590

Leu Glu Arg Arg Val Ser Ala Arg Leu Leu Gly Asp Ala Val Ala Val
        595                 600                 605

Thr Gln Cys Val Asn Ile Ser Ser Gly His Val Tyr Ile Gln Asn Ser
    610                 615                 620

Met Arg Val Thr Gly Ser Ser Thr Thr Cys Tyr Ser Arg Pro Leu Val
625                 630                 635                 640

Ser Phe Arg Ala Leu Asn Asp Ser Glu Tyr Ile Glu Gly Gln Leu Gly
                645                 650                 655

Glu Asn Asn Asp Leu Leu Val Glu Arg Lys Leu Ile Glu Pro Cys Thr
            660                 665                 670

Val Asn Asn Lys Arg Tyr Phe Lys Phe Gly Ala Asp Tyr Val Tyr Phe
        675                 680                 685

Glu Asp Tyr Ala Tyr Val Arg Lys Val Pro Leu Ser Glu Ile Glu Leu
    690                 695                 700
```

```
Ile Ser Ala Tyr Val Asp Leu Asn Leu Thr Leu Leu Glu Asp Arg Glu
705                 710                 715                 720

Phe Leu Pro Leu Glu Val Tyr Thr Arg Ala Glu Leu Glu Asp Thr Gly
                725                 730                 735

Leu Leu Asp Tyr Ser Glu Ile Gln Arg Arg Asn Gln Leu His Ala Leu
            740                 745                 750

Lys Phe Tyr Asp Ile Asp Ser Ile Val Arg Val Asp Asn Asn Leu Val
        755                 760                 765

Ile Met Arg Gly Met Ala Asn Phe Phe Gln Gly Leu Gly Asp Val Gly
    770                 775                 780

Ala Gly Phe Gly Lys Val Val Leu Gly Ala Ala Ser Ala Val Ile Ser
785                 790                 795                 800

Thr Val Ser Gly Val Ser Ser Phe Leu Asn Asn Pro Phe Gly Ala Leu
                805                 810                 815

Ala Val Gly Leu Leu Ile Leu Ala Gly Ile Val Ala Ala Phe Leu Ala
            820                 825                 830

Tyr Arg Tyr Ile Ser Arg Leu Arg Ala Asn Pro Met Lys Ala Leu Tyr
        835                 840                 845

Pro Val Thr Thr Arg Asn Leu Lys Gln Thr Ala Lys Ser Pro Ala Ser
    850                 855                 860

Thr Ala Gly Gly Asp Ser Asp Pro Gly Val Asp Asp Phe Asp Glu Glu
865                 870                 875                 880

Lys Leu Met Gln Ala Arg Glu Met Ile Lys Tyr Met Ser Leu Val Ser
                885                 890                 895

Ala Met Glu Gln Gln Glu His Lys Ala Met Lys Lys Asn Lys Gly Pro
            900                 905                 910

Ala Ile Leu Thr Ser His Leu Thr Asn Met Ala Leu Arg Arg Arg Gly
        915                 920                 925

Pro Lys Tyr Gln Arg Leu Asn Asn Leu Asp Ser Gly Asp Asp Thr Glu
    930                 935                 940

Thr Asn Leu Val
945
```

<210> SEQ ID NO 10
<211> LENGTH: 2847
<212> TYPE: DNA
<213> ORGANISM: artificial sequence
<220> FEATURE:
<223> OTHER INFORMATION: gB DNA S49775 encoding AAB24381

<400> SEQUENCE: 10

```
atgtccactc gtggcgatct tgggaagcgg cgacgaggga gtcgttggca gggacacagt      60

ggctattttc gacagagatg ttttttccct tctctactcg gtattgcagc gactggctcc     120

agacatggta acggatcgtc gggattaacc agactagcta gatatgtttc atttatctgg     180

atcgtactat tcttagtcgg tccccgtcca gtagagggtc aatctggaag cacatcggaa     240

caaccccggc ggactgtagc taccctgag gtagggggta caccaccaaa accaactaca     300

gatcccaccg atatgtcgga tatgagggaa gctctccgtg cgtcccaaat agaggctaac     360

ggaccatcga ctttttatat gtgtccacca ccttcaggat ctactgtcgt gcgtttagag     420

ccaccacggg cctgtccaga ttataaacta gggaaaaatt ttaccgaggg tatagctgta     480

atatttaaag aaaatatagc gccatataaa ttcaaggcaa atatatacta taaaaacatt     540

attatgacaa cggtatggtc tgggagttcc tatgccgtta caaccaaccg atatacagac     600
```

-continued

```
agggttcccg tgaaagttca agagattaca gatctcatag atagacgggg tatgtgcctc    660
tcgaaagctg attacgttcg taacaattat caatttacgg cctttgatcg agacgaggat    720
cccagagaac tgcctctgaa accctccaag ttcaacactc cagagtcccg tggatggcac    780
accaccaatg aaacatacac aaagatcggt gctgctggat ttcaccactc tgggacctct    840
gtaaattgca tcgtagagga agtggatgca agatctgtat atccatatga ctcatttgct    900
atctccactg gtgacgtgat tcacatgtct ccattctttg ggctgaggga tggagcccat    960
gtagaacata ctagttattc ttcagacaga tttcaacaaa tcgagggata ctatccaata   1020
gacttggata cgcgattaca actgggggca ccagtttctc gcaatttttt ggaaactccg   1080
catgtgacag tggcctggaa ctggacccca aagtgtggtc gggtatgtac cttagccaaa   1140
tggagggaaa tagatgaaat gctacgcgat gaatatcagg gctcctatag atttacagtc   1200
aagaccatat ccgctacttt catctccaat acttcacaat ttgaaatcaa tcgtatccgt   1260
ttgggggact gtgccaccaa ggaggcagcc gaagccatag accggattta taagagtaaa   1320
tatagtaaaa ctcatattca gactggaacc ctggagacct acctagcccg tggcggattt   1380
ctaatagctt tccgtcccat gatcagcaac gaactagcaa agttatatat caatgaatta   1440
gcacgttcca atcgcacggt agatctcagt gcactcctca atccatctgg ggaaacagta   1500
caacgaacta gaagatcggt cccatctaat caacatcata ggtcgcggcg cagcacaata   1560
gaggggggta tagaaaccgt gaacaatgca tcactcctca agaccacctc atctgtggaa   1620
ttcgcaatgc tacaatttgc ctatgactac atacaagccc atgtaaatga aatgttgagt   1680
cggatagcca ctgcctggtg tacacttcag aaccgcgaac atgtgctgtg gacagagacc   1740
ctaaaactca atcccggtgg ggtggtctcg atggccctag aacgtcgtgt atccgcgcgc   1800
ctacttggag atgccgtcgc cgtaacacaa tgtgttaaca tttctagcgg acatgtctat   1860
atccaaaatt ctatgcgggt gacgggttca tcaacgacat gttacagccg ccctcttgtt   1920
tccttccgtg ccctcaatga ctccgaatac atagaaggac aactagggga aaacaatgac   1980
cttctcgtgg aacgaaaact aattgagcct tgcactgtca ataataagcg gtattttaag   2040
tttggggcag attatgtata ttttgaggat tatgcgtatg tccgtaaagt cccgctatcg   2100
gagatagaac tgataagtgc gtatgtggat ttaaatctta ctctcctaga ggatcgtgaa   2160
tttctcccac tcgaagttta tacacgagct gagctggaag ataccggcct tttggactac   2220
agcgagattc aacggcgcaa ccaactccac gccttaaaat tttatgatat agacagcata   2280
gtcagagtgg ataataatct tgtcatcatg cgtggtatgg caaatttttt tcagggactc   2340
ggggatgtgg gggctggttt cggcaaggtg gtcttagggg ctgcgagtgc ggtaatctca   2400
acagtatcag gcgtatcatc atttctaaac aacccatttg gagcattggc cgtgggactg   2460
ttaatattag ctggcatcgt cgcagcattc ctggcatatc gctatatatc tagattacgt   2520
gcaaatccaa tgaaagcctt atatcctgtg acgactagga atttgaaaca gacggctaag   2580
agccccgcct caacggctgg tggggatagc gacccgggag tcgatgactt cgatgaggaa   2640
aagctaatgc aggcaaggga gatgataaaa tatatgtccc tcgtatcggc tatggagcaa   2700
caagaacata aggcgatgaa aaagaataag ggcccagcga tcctaacgag tcatctcact   2760
aacatggccc tccgtcgccg tggacctaaa taccaacgcc tcaataatct tgatagcggt   2820
gatgatactg aaacaaatct tgtctaa                                       2847
```

<210> SEQ ID NO 11
<211> LENGTH: 879

-continued

```
<212> TYPE: PRT
<213> ORGANISM: artificial sequence
<220> FEATURE:
<223> OTHER INFORMATION: gB protein AK51052

<400> SEQUENCE: 11

Met Phe Ser Leu Tyr Leu Tyr Ile Phe Phe Ile Ile Tyr Thr Leu Ile
1               5                   10                  15

Ile Cys Asp Pro Thr Thr Pro Glu Ser Thr Ile Asn Pro Leu Asn His
            20                  25                  30

His Asn Leu Ser Thr Pro Lys Pro Thr Ser Asp Asp Ile Arg Glu Ile
        35                  40                  45

Leu Arg Glu Ser Gln Ile Glu Ser Asp Asp Thr Ser Thr Phe Tyr Met
    50                  55                  60

Cys Pro Pro Pro Ser Gly Ser Thr Leu Val Arg Leu Glu Pro Pro Arg
65                  70                  75                  80

Ala Cys Pro Asn Tyr Lys Leu Gly Lys Asn Phe Thr Glu Gly Ile Ala
                85                  90                  95

Val Ile Phe Lys Glu Asn Ile Ser Pro Tyr Lys Phe Lys Ala Asn Ile
            100                 105                 110

Tyr Tyr Lys Asn Ile Ile Ile Thr Thr Val Trp Ser Gly Ser Thr Tyr
        115                 120                 125

Ala Val Ile Thr Asn Arg Tyr Thr Asp Arg Val Pro Ile Gly Val Pro
    130                 135                 140

Glu Ile Thr Glu Leu Ile Asp Arg Arg Gly Met Cys Leu Ser Lys Ala
145                 150                 155                 160

Asp Tyr Ile Arg Asn Asn Tyr Glu Phe Thr Ala Phe Asp Lys Asp Glu
                165                 170                 175

Asp Pro Arg Glu Val His Leu Lys Pro Ser Lys Phe Asn Thr Pro Gly
            180                 185                 190

Ser Arg Gly Trp His Thr Val Asn Asp Thr Tyr Thr Lys Ile Gly Gly
        195                 200                 205

Ser Gly Phe Tyr His Ser Gly Thr Ser Val Asn Cys Ile Val Glu Glu
    210                 215                 220

Val Asp Ala Arg Ser Val Tyr Pro Tyr Asp Ser Phe Ala Ile Ser Thr
225                 230                 235                 240

Gly Asp Ile Ile His Met Ser Pro Phe Phe Gly Leu Arg Asp Gly Ala
                245                 250                 255

His Thr Glu Tyr Ile Ser Tyr Ser Thr Asp Arg Phe Gln Gln Ile Glu
            260                 265                 270

Gly Tyr Tyr Pro Ile Asp Leu Asp Thr Arg Leu Gln Leu Gly Ala Pro
        275                 280                 285

Val Ser Arg Asn Phe Leu Thr Thr Gln His Val Thr Val Ala Trp Asn
    290                 295                 300

Trp Val Pro Lys Ile Arg Glu Val Cys Thr Leu Ala Lys Trp Arg Glu
305                 310                 315                 320

Ile Asp Glu Ile Ile Arg Asp Glu Tyr Lys Gly Ser Tyr Arg Phe Thr
                325                 330                 335

Ala Lys Ser Ile Ser Ala Thr Phe Ile Ser Asp Thr Thr Gln Phe Asp
            340                 345                 350

Ile Asp Arg Val Lys Leu Ser Asp Cys Ala Lys Arg Glu Ala Ile Glu
        355                 360                 365

Ala Ile Asp Lys Ile Tyr Lys Lys Lys Tyr Asn Lys Thr His Ile Gln
    370                 375                 380
```

-continued

```
Thr Gly Glu Leu Glu Thr Tyr Leu Ala Arg Gly Gly Phe Ile Ile Ala
385                 390                 395                 400

Phe Arg Pro Met Ile Ser Asn Glu Leu Ala Lys Leu Tyr Ile Asn Glu
                405                 410                 415

Leu Val Arg Ser Asn Arg Thr Val Asp Leu Lys Ser Leu Leu Asn Pro
            420                 425                 430

Ser Val Arg Gly Gly Ala Arg Lys Arg Arg Ser Val Glu Glu Asn Lys
        435                 440                 445

Arg Ser Lys Arg Asn Ile Glu Gly Gly Ile Glu Asn Val Asn Asn Ser
    450                 455                 460

Thr Ile Ile Lys Thr Thr Ser Ser Val His Phe Ala Met Leu Gln Phe
465                 470                 475                 480

Ala Tyr Asp His Ile Gln Ser His Val Asn Glu Met Leu Ser Arg Ile
                485                 490                 495

Ala Thr Ala Trp Cys Asn Leu Gln Asn Lys Glu Arg Thr Leu Trp Asn
            500                 505                 510

Glu Val Met Lys Leu Asn Pro Thr Ser Val Ala Ser Val Ala Met Asp
        515                 520                 525

Gln Arg Val Ser Ala Arg Met Leu Gly Asp Val Leu Ala Val Thr Gln
    530                 535                 540

Cys Val Asn Ile Ser Gly Ser Ser Val Phe Ile Gln Asn Ser Met Arg
545                 550                 555                 560

Val Leu Gly Ser Thr Thr Thr Cys Tyr Ser Arg Pro Leu Ile Ser Phe
                565                 570                 575

Lys Ala Leu Glu Asn Ser Thr Asn Tyr Ile Glu Gly Gln Leu Gly Glu
            580                 585                 590

Asn Asn Glu Leu Leu Val Glu Arg Lys Leu Ile Glu Pro Cys Thr Ala
        595                 600                 605

Asn His Lys Arg Tyr Phe Lys Phe Gly Val Asp Tyr Val Tyr Phe Glu
    610                 615                 620

Asn Tyr Ala Tyr Val Arg Lys Val Pro Leu Asn Glu Ile Glu Met Ile
625                 630                 635                 640

Ser Ala Tyr Val Asp Leu Asn Ile Thr Leu Leu Glu Asp Arg Glu Phe
                645                 650                 655

Leu Pro Leu Glu Val Tyr Thr Arg Ala Glu Leu Glu Asp Thr Gly Leu
            660                 665                 670

Leu Asp Tyr Ser Glu Ile Gln Arg Arg Asn Gln Leu His Ala Leu Lys
        675                 680                 685

Phe Tyr Asp Ile Asp Ser Val Val Lys Val Asp Asn Asn Val Val Ile
    690                 695                 700

Met Arg Gly Ile Ala Asn Phe Phe Gln Gly Leu Gly Asp Val Gly Ala
705                 710                 715                 720

Gly Phe Gly Lys Val Val Leu Gly Ala Ala Asn Ala Val Ile Ala Thr
                725                 730                 735

Val Ser Gly Val Ser Ser Phe Leu Asn Asn Pro Phe Gly Ala Leu Ala
            740                 745                 750

Val Gly Leu Leu Ile Leu Ala Gly Leu Phe Ala Ala Phe Leu Ala Tyr
        755                 760                 765

Arg Tyr Val Ser Lys Leu Lys Ser Asn Pro Met Lys Ala Leu Tyr Pro
    770                 775                 780

Val Thr Thr Arg Asn Leu Lys Glu Ser Val Lys Asn Gly Asn Ser Gly
785                 790                 795                 800

Asn Asn Ser Asp Gly Glu Glu Asn Asp Asp Asn Ile Asp Glu Glu Lys
```

-continued

```
                805                 810                 815

Leu Gln Gln Ala Lys Glu Met Ile Lys Tyr Met Ser Leu Val Ser Ala
            820                 825                 830

Met Glu Gln Gln Glu His Lys Ala Ile Lys Lys Asn Ser Gly Pro Ala
        835                 840                 845

Leu Leu Ala Ser His Ile Thr Asn Leu Ser Leu Lys His Arg Gly Pro
    850                 855                 860

Lys Tyr Lys Arg Leu Lys Asn Val Asn Glu Asn Glu Ser Lys Val
865                 870                 875


<210> SEQ ID NO 12
<211> LENGTH: 2640
<212> TYPE: DNA
<213> ORGANISM: artificial sequence
<220> FEATURE:
<223> OTHER INFORMATION: gB DNA AF361073 encoding AAK51052

<400> SEQUENCE: 12

atgttttcat tgtatctata tattttttt attatttata ctttaataat atgtgatcca     60

acaacaccgg aaagtactat taatccatta aatcatcaca atttatcaac acctaaacct    120

acttcggatg atattcgtga aattttacgt gaatcccaaa ttgaatctga tgatacatca    180

acattttaca tgtgcccacc accatcggga tcaacattgg tgcgtttgga gccacctaga    240

gcatgtccta actataaact tggtaaaaat tttacagaag gaattgctgt aatatttaag    300

gaaaatattt ctccttataa atttaaagct aatatatact acaaaaatat tattatcacc    360

actgtatggt ctggaagcac atatgcagta attactaata gatatacaga tcgtgtacct    420

ataggtgttc ctgaaattac agagttgatt gatagaagag gtatgtgttt atcaaaagct    480

gattatattc gtaataatta tgaatttacc gcatttgata aggatgaaga ccccagagaa    540

gttcatttaa agccttcaaa gtttaataca ccaggatccc gtggatggca tacagttaat    600

gatacttaca caaaaattgg gggttctgga ttttatcatt ctggaacatc tgtaaattgt    660

atagttgaag aagttgatgc cagatctgtt tatccatatg attcatttgc tatctccacc    720

ggggatataa ttcatatgtc cccttttttt ggattacgag atggtgctca tactgaatat    780

attagttatt caactgatag atttcaacaa atagaaggtt attatcctat cgacttagat    840

actagactac agcttggtgc accagtttct aggaattttt taacaacaca acacgttact    900

gttgcttgga attgggttcc aaaaattcgt gaagtgtgta ctttggctaa atggcgtgaa    960

attgatgaaa ttattcgtga tgagtataag ggatcttaca gatttacagc aaaatcaata   1020

tctgcaacat ttatttctga tactactcaa tttgatattg atcgtgtaaa gttaagtgat   1080

tgtgccaaac gtgaagctat agaagctatt gataagatct acaaaaaaaa atataataaa   1140

actcatattc aaacaggaga attggaaaca tacttggcta gagggggatt tattatagca   1200

tttagaccaa tgattagtaa tgagttagca aaattgtata taaatgagtt agtaagatct   1260

aatcgtacgg ttgatttgaa atctctttta aatccatctg taagaggggg ggctagaaag   1320

agaagatcag tagaggaaaa taaaagatca aaacgtaata ttgaaggtgg tattgaaaat   1380

gtaaataatt caacaataat taagacaact tcatctgttc attttgctat gcttcagttt   1440

gcctatgatc atattcaatc acatgttaat gaaatgctta gtagaattgc aactgcatgg   1500

tgtaatcttc aaaataaaga gagaaccctt tggaatgaag ttatgaaact taatccaact   1560

agtgtggctt cggttgctat ggatcaaaga gtttcagcac gaatgttagg ggatgttctt   1620

gcagttactc aatgtgttaa tatatcaggt tctagtgttt ttattcaaaa ttccatgcgt   1680
```

-continued

```
gttttagggt caacaactac atgttacagt cgtcctctta tatcatttaa agcactagaa   1740

aactcaacta actatattga aggacaactt ggggaaaata atgaactatt agtagaacga   1800

aagctaattg aaccatgtac agctaaccat aaaagatatt ttaaatttgg tgtagattat   1860

gtatattttg aaaactatgc atatgttcga aaggtacctc ttaatgaaat tgaaatgatc   1920

agtgcatatg tagatcttaa tattacatta cttgaggatc gtgaattttt accactagag   1980

gtatatactc gagcagagtt agaagataca ggactattgg actatagtga gattcaacgt   2040

agaaatcaac tacatgcact taagttttat gatattgaca gtgttgtaaa agttgataat   2100

aatgttgtaa ttatgagggg cattgcaaat ttcttccaag gacttggaga tgttggagcg   2160

ggatttggaa aagttgtttt gggtgctgca aatgctgtta ttgcaactgt ttctggagtg   2220

tcctcgtttc ttaataaccc atttggggcg ctagccgttg gattgctgat tttagctgga   2280

ctatttgcag cgtttttggc ttatagatat gtttctaaac ttaagtcaaa tccaatgaaa   2340

gcactatacc cagtaactac aagaaattta aaagaaagtg ttaagaatgg taattctgga   2400

aataatagtg atggagaaga aaatgatgat aatatcgatg aagaaaagct tcaacaagct   2460

aaagaaatga ttaaatatat gtctctagtt tctgctatgg aacagcagga acataaagct   2520

attaaaaaaa atagtggccc tgcccttcta gcaagtcaca ttacaaacct atctcttaaa   2580

catcgtggtc caaaatacaa acgtttgaaa aatgtaaatg aaaatgaaag taaagtttaa   2640
```

<210> SEQ ID NO 13
<211> LENGTH: 879
<212> TYPE: PRT
<213> ORGANISM: artificial sequence
<220> FEATURE:
<223> OTHER INFORMATION: gB protein AAT93732

<400> SEQUENCE: 13

```
Met Phe Ser Leu Tyr Leu Tyr Ile Phe Phe Ile Ile Tyr Thr Leu Ile
1               5                   10                  15

Ile Cys Asp Pro Thr Thr Pro Glu Ser Thr Ile Asn Pro Leu Asn His
            20                  25                  30

His Asn Leu Ser Thr Pro Lys Pro Thr Ser Asp Asp Ile Arg Glu Ile
        35                  40                  45

Leu Arg Glu Ser Gln Ile Glu Ser Asp Asp Thr Ser Thr Phe Tyr Met
    50                  55                  60

Cys Pro Pro Pro Ser Gly Ser Thr Leu Val Arg Leu Glu Pro Pro Arg
65                  70                  75                  80

Ala Cys Pro Asn Tyr Lys Leu Gly Lys Asn Phe Thr Glu Gly Ile Ala
                85                  90                  95

Val Ile Phe Lys Gly Asn Ile Ser Pro Tyr Lys Phe Lys Ala Asn Ile
            100                 105                 110

Tyr Tyr Lys Asn Ile Ile Ile Thr Thr Val Trp Ser Gly Ser Thr Tyr
        115                 120                 125

Ala Val Ile Thr Asn Arg Tyr Thr Asp Arg Val Pro Ile Gly Val Pro
    130                 135                 140

Glu Ile Thr Glu Leu Ile Asp Arg Arg Gly Met Cys Leu Ser Lys Ala
145                 150                 155                 160

Asp Tyr Ile Arg Asn Asn Tyr Glu Phe Thr Ala Phe Asp Lys Asp Glu
                165                 170                 175

Asp Pro Arg Glu Val His Leu Lys Pro Ser Lys Phe Asn Thr Pro Gly
            180                 185                 190
```

-continued

```
Ser Arg Gly Trp His Thr Val Asn Asp Thr Tyr Thr Lys Ile Gly Gly
        195                 200                 205

Ser Gly Phe Tyr His Ser Gly Thr Ser Val Asn Cys Ile Val Glu Glu
    210                 215                 220

Val Asp Ala Arg Ser Val Tyr Pro Tyr Asp Ser Phe Ala Ile Ser Thr
225                 230                 235                 240

Gly Asp Ile Ile His Met Ser Pro Phe Phe Gly Leu Arg Asp Gly Ala
                245                 250                 255

His Thr Glu Tyr Ile Ser Tyr Ser Thr Asp Arg Phe Gln Gln Ile Glu
            260                 265                 270

Gly Tyr Tyr Pro Ile Asp Leu Asp Thr Arg Leu Gln Leu Gly Ala Pro
        275                 280                 285

Val Ser Arg Asn Phe Leu Thr Thr Gln His Val Thr Val Ala Trp Asn
    290                 295                 300

Trp Val Pro Lys Ile Arg Glu Val Cys Thr Leu Ala Lys Trp Arg Glu
305                 310                 315                 320

Ile Asp Glu Ile Ile Arg Asp Glu Tyr Lys Gly Ser Tyr Arg Phe Thr
                325                 330                 335

Ala Lys Ser Ile Ser Ala Thr Phe Ile Ser Asp Thr Thr Gln Phe Asp
            340                 345                 350

Ile Asp Arg Val Lys Leu Ser Asp Cys Ala Lys Arg Glu Ala Ile Glu
        355                 360                 365

Ala Ile Asp Lys Ile Tyr Lys Lys Lys Tyr Asn Lys Thr His Ile Gln
    370                 375                 380

Thr Gly Glu Leu Glu Thr Tyr Leu Ala Arg Gly Gly Phe Ile Ile Ala
385                 390                 395                 400

Phe Arg Pro Met Ile Ser Asn Glu Leu Ala Lys Leu Tyr Ile Asn Glu
                405                 410                 415

Leu Val Arg Ser Asn Arg Thr Val Asp Leu Lys Ser Leu Leu Asn Pro
            420                 425                 430

Ser Val Arg Gly Gly Ala Arg Lys Arg Arg Ser Val Glu Glu Asn Lys
        435                 440                 445

Arg Ser Lys Arg Asn Ile Glu Gly Gly Ile Glu Asn Val Asn Asn Ser
    450                 455                 460

Thr Ile Ile Lys Thr Thr Ser Ser Val His Phe Ala Met Leu Gln Phe
465                 470                 475                 480

Ala Tyr Asp His Ile Gln Ser His Val Asn Glu Met Leu Ser Arg Ile
                485                 490                 495

Ala Thr Ala Trp Cys Asn Leu Gln Asn Lys Glu Arg Thr Leu Trp Asn
            500                 505                 510

Glu Val Met Lys Leu Asn Pro Thr Ser Val Ala Ser Val Ala Met Asp
        515                 520                 525

Gln Arg Val Ser Ala Arg Met Leu Gly Asp Val Leu Ala Val Thr Gln
    530                 535                 540

Cys Val Asn Ile Ser Gly Ser Ser Val Phe Ile Gln Asn Ser Met Arg
545                 550                 555                 560

Val Leu Gly Ser Thr Thr Thr Cys Tyr Ser Arg Pro Leu Ile Ser Phe
                565                 570                 575

Lys Ala Leu Glu Asn Ser Thr Asn Tyr Ile Glu Gly Gln Leu Gly Glu
            580                 585                 590

Asn Asn Glu Leu Leu Val Glu Arg Lys Leu Ile Glu Pro Cys Thr Ala
        595                 600                 605

Asn His Lys Arg Tyr Phe Lys Phe Gly Val Asp Tyr Val Tyr Phe Glu
```

```
    610                 615                 620

Asn Tyr Ala Tyr Val Arg Lys Val Pro Leu Asn Glu Ile Glu Met Ile
625                 630                 635                 640

Ser Ala Tyr Val Asp Leu Asn Ile Thr Leu Leu Glu Asp Arg Glu Phe
                645                 650                 655

Leu Pro Leu Glu Val Tyr Thr Arg Ala Glu Leu Glu Asp Thr Gly Leu
            660                 665                 670

Leu Asp Tyr Ser Glu Ile Gln Arg Arg Asn Gln Leu His Ala Leu Lys
        675                 680                 685

Phe Tyr Asp Ile Asp Ser Val Val Lys Val Asp Asn Asn Val Val Ile
    690                 695                 700

Met Arg Gly Ile Ala Asn Phe Phe Gln Gly Leu Gly Asp Val Gly Ala
705                 710                 715                 720

Gly Phe Gly Lys Val Val Leu Gly Ala Ala Asn Ala Val Ile Ala Thr
                725                 730                 735

Val Ser Gly Val Ser Ser Phe Leu Asn Asn Pro Phe Gly Ala Leu Ala
            740                 745                 750

Val Gly Leu Leu Ile Leu Ala Gly Leu Phe Ala Ala Phe Leu Ala Tyr
        755                 760                 765

Arg Tyr Val Ser Lys Leu Lys Ser Asn Pro Met Lys Ala Leu Tyr Pro
    770                 775                 780

Val Thr Thr Arg Asn Leu Lys Glu Ser Val Lys Asn Gly Asn Ser Gly
785                 790                 795                 800

Asn Asn Ser Asp Gly Glu Glu Asn Asp Asp Asn Ile Asp Glu Glu Lys
                805                 810                 815

Leu Gln Gln Ala Lys Glu Met Ile Lys Tyr Met Ser Leu Val Ser Ala
            820                 825                 830

Met Glu Gln Gln Glu His Lys Ala Ile Lys Lys Asn Ser Gly Pro Ala
        835                 840                 845

Leu Leu Ala Ser His Ile Thr Asn Leu Ser Leu Lys His Arg Gly Pro
    850                 855                 860

Lys Tyr Lys Arg Leu Lys Asn Val Asn Glu Asn Glu Ser Lys Val
865                 870                 875
```

<210> SEQ ID NO 14
<211> LENGTH: 2640
<212> TYPE: DNA
<213> ORGANISM: artificial sequence
<220> FEATURE:
<223> OTHER INFORMATION: gB DNA AY582737 encoding AAT93732

<400> SEQUENCE: 14

```
atgttttcat tgtatctata tatttttttt attatttata ctttaataat atgtgatcca      60

acaacaccgg aaagtactat taatccatta aatcatcaca atttatcaac acctaaacct     120

acttcggatg atattcgtga aattttacgt gaatcccaaa ttgaatctga tgatacatca     180

acattttaca tgtgcccacc accatcggga tcaacattgg tgcgtttgga gccacctaga     240

gcatgtccta actataaact tggtaaaaat tttacagaag gaattgctgt aatatttaag     300

ggaaatattt ctccttataa atttaaagct aatatatact acaaaaatat tattatcacc     360

actgtatggt ctggaagcac atatgcagta attactaata gatatacaga tcgtgtacct     420

ataggtgttc ctgaaattac agagttgatt gatagaagag gtatgtgttt atcaaaagct     480

gattatattc gtaataatta tgaatttacc gcatttgata aggatgaaga ccccagagaa     540

gttcatttaa agccttcaaa gtttaataca ccaggatccc gtggatggca tacagttaat     600
```

gatacttaca caaaaattgg gggttctgga ttttatcatt ctggaacatc tgtaaattgt 660
atagttgaag aagttgatgc cagatctgtt tatccatatg attcatttgc tatctccacc 720
ggggatataa ttcatatgtc cccttttttt ggattacgag atggtgctca tactgaatat 780
attagttatt caactgatag atttcaacaa atagaaggtt attatcctat cgacttagat 840
actagactac agcttggtgc accagtttct aggaattttt taacaacaca acacgttact 900
gttgcttgga attgggttcc aaaaattcgt gaagtgtgta ctttggctaa atggcgtgaa 960
attgatgaaa ttattcgtga tgagtataag ggatcttaca gatttacagc aaaatcaata 1020
tctgcaacat ttatttctga tactactcaa tttgatattg atcgtgtaaa gttaagtgat 1080
tgtgccaaac gtgaagctat agaagctatt gataagatct acaaaaaaaa atataataaa 1140
actcatattc aaacaggaga attggaaaca tacttggcta gagggggatt tattatagca 1200
tttagaccaa tgattagtaa tgagttagca aaattgtata taaatgagtt agtaagatct 1260
aatcgtacgg ttgatttgaa atctctttta aatccatctg taagaggggg ggctagaaag 1320
agaagatcag tagaggaaaa taaaagatca aaacgtaata ttgaaggtgg tattgaaaat 1380
gtaaataatt caacaataat taagacaact tcatctgttc attttgctat gcttcagttt 1440
gcctatgatc atattcaatc acatgttaat gaaatgctta gtagaattgc aactgcatgg 1500
tgtaatcttc aaaataaaga gagaaccctt tggaatgaag ttatgaaact taatccaact 1560
agtgtggctt cggttgctat ggatcaaaga gtttcagcac gaatgttagg ggatgttctt 1620
gcagttactc aatgtgttaa tatatcaggt tctagtgttt ttattcaaaa ttccatgcgt 1680
gttttagggt caacaactac atgttacagt cgtcctctta tatcatttaa agcactagaa 1740
aactcaacta actatattga aggacaactt ggggaaaata atgaactatt agtagaacga 1800
aagctaattg aaccatgtac agctaaccat aaaagatatt ttaaatttgg tgtagattat 1860
gtatattttg aaaactatgc atatgttcga aaggtacctc ttaatgaaat tgaaatgatc 1920
agtgcatatg tagatcttaa tattacatta cttgaggatc gtgaattttt accactagag 1980
gtatatactc gagcagagtt agaagataca ggactattgg actatagtga gattcaacgt 2040
agaaatcaac tacatgcact taagttttat gatattgaca gtgttgtaaa agttgataat 2100
aatgttgtaa ttatgagggg cattgcaaat tttttccaag gacttggaga tgttggagcg 2160
ggatttggaa aagttgtttt gggtgctgca aatgctgtta ttgcaactgt ttctggagtg 2220
tcctcgtttc ttaataaccc atttggggcg ctagccgttg gattgctgat tttagctgga 2280
ctatttgcag cgtttttggc ttatagatat gtttctaaac ttaagtcaaa tccaatgaaa 2340
gcactatacc cagtaactac aagaaattta aaagaaagtg ttaagaatgg taattctgga 2400
aataatagtg atggagaaga aaatgatgat aatatcgatg aagaaaagct tcaacaagct 2460
aaagaaatga ttaaatatat gtctctagtt tctgctatgg aacagcagga acataaagct 2520
attaaaaaaa atagtggccc tgcccttcta gcaagtcaca ttacaaacct atctcttaaa 2580
catcgtggtc caaaatacaa acgtttgaaa aatgtaaatg aaaatgaaag taaagtttaa 2640

<210> SEQ ID NO 15
<211> LENGTH: 881
<212> TYPE: PRT
<213> ORGANISM: artificial sequence
<220> FEATURE:
<223> OTHER INFORMATION: gB protein CAA92272

<400> SEQUENCE: 15

-continued

```
Met Tyr Leu Ile Thr Leu Val Phe Phe Ile Asn Ile Leu Val Ile Gln
1               5                   10                  15

Cys Val Pro Thr Thr Gln Pro Thr Glu Ser Thr Pro Pro Ile Thr Pro
            20                  25                  30

Ser Pro Pro Pro Lys Asn Ser Ser Ser Asn Thr Glu Leu Asn Asp Asp
        35                  40                  45

Met Arg Glu Ile Leu Gly Glu Ser Gln Ile Glu Ser Asp Asp Thr Ala
    50                  55                  60

Thr Phe Phe Met Cys Pro Pro Pro Ser Gly Ser Thr Leu Val Arg Leu
65                  70                  75                  80

Glu Pro Pro Arg Ala Cys Pro Asn Tyr Lys Leu Gly Lys Asn Phe Thr
                85                  90                  95

Glu Gly Ile Ala Val Ile Phe Lys Glu Asn Ile Ser Pro Tyr Lys Phe
            100                 105                 110

Lys Ala Asn Ile Tyr Tyr Lys Asn Ile Ile Ile Thr Thr Val Trp Ser
        115                 120                 125

Gly Ser Ser Tyr Ala Val Val Thr Asn Met His Thr Asp Arg Val Pro
    130                 135                 140

Ile Lys Val Gln Glu Ile Thr Glu Leu Ile Asp Arg Arg Gly Met Cys
145                 150                 155                 160

Leu Ser Lys Ala Asp Tyr Ile Arg Asn Asn Tyr Glu Phe Thr Ala Phe
                165                 170                 175

Asp Lys Asp Glu Asp Pro Arg Glu Met His Leu Lys Pro Ser Lys Phe
            180                 185                 190

Asn Thr Pro Gly Ser Arg Gly Trp His Thr Thr Asn Asp Thr Tyr Thr
        195                 200                 205

Lys Ile Gly Ser Pro Gly Phe Tyr Arg Thr Gly Thr Ser Val Asn Cys
    210                 215                 220

Ile Val Glu Glu Val Asp Ala Arg Ser Val Tyr Pro Tyr Asp Ser Phe
225                 230                 235                 240

Gly Ile Ser Thr Gly Asp Ile Ile His Met Ser Pro Phe Phe Gly Leu
                245                 250                 255

Arg Asp Gly Ala His Thr Glu His Thr Ser Tyr Ser Asn Asp Arg Phe
            260                 265                 270

Gln Gln Ile Glu Gly Tyr Tyr Pro Ile Asp Leu Asp Thr Arg Leu Gln
        275                 280                 285

Val Gly Gly Pro Val Ser Arg Asn Phe Leu Thr Thr Gln His Val Thr
    290                 295                 300

Val Ala Trp Asn Trp Val Pro Lys Ile Arg Glu Val Cys Thr Leu Ala
305                 310                 315                 320

Lys Trp Arg Glu Ile Asp Glu Ile Ile Arg Asp Glu Tyr Lys Gly Ser
                325                 330                 335

Tyr Arg Phe Thr Ala Lys Ser Ile Ser Ala Thr Phe Ile Ser Asp Ala
            340                 345                 350

Thr Gln Phe Asp Ile Asn Arg Val Lys Leu Ser Asp Cys Ala Lys Arg
        355                 360                 365

Glu Ala Thr Glu Ala Ile Asp Lys Ile Tyr Lys Asn Lys Tyr Asn Lys
    370                 375                 380

Thr His Ile Gln Thr Gly Glu Leu Glu Thr Tyr Leu Ala Arg Gly Gly
385                 390                 395                 400

Phe Ile Ile Ala Phe Arg Pro Met Ile Ser Asn Glu Leu Ala Lys Leu
                405                 410                 415

Tyr Ile Asn Glu Leu Ala Arg Ser Glu Arg Ile Val Asp Leu Asn Ala
```

-continued

```
            420                 425                 430

Leu Leu Asn Pro Ser His Ser Val Gly Gly Arg Lys Lys Arg Ser Ile
        435                 440                 445

Glu Thr Glu Thr Leu Gly Arg Ser Lys Arg Asp Val Asp Gly Gly Val
    450                 455                 460

Gln Asn Val Asn Asn Ala Thr Leu Ile Lys Thr Thr Ser Ser Ile His
465                 470                 475                 480

Phe Ala Met Leu Gln Phe Ala Tyr Asp His Ile Gln Ser His Val Asn
                485                 490                 495

Glu Met Leu Ser Arg Ile Ala Thr Ala Trp Cys Asn Leu Gln Asn Lys
            500                 505                 510

Glu Arg Thr Leu Trp Asn Glu Val Met Lys Leu Asn Pro Thr Ser Ile
        515                 520                 525

Thr Ser Thr Ile Met Asp Gln Lys Val Ser Ala Arg Leu Leu Gly Asp
    530                 535                 540

Val Ile Ala Val Thr Gln Cys Val Asn Ile Ser Gly Ser Asn Val Phe
545                 550                 555                 560

Ile Gln Asn Ser Met Arg Val Thr Gly Ser Thr Thr Thr Cys Tyr Ser
                565                 570                 575

Arg Pro Leu Ile Ser Phe Lys Ala Leu Glu Asn Ser Thr Asp Tyr Ile
            580                 585                 590

Glu Gly Gln Leu Gly Glu Asn Asn Glu Leu Leu Val Asp Arg Lys Leu
        595                 600                 605

Ile Glu Pro Cys Thr Ala Asn Asn Lys Arg Tyr Phe Lys Phe Gly Val
    610                 615                 620

Asp Tyr Val Tyr Phe Glu Asn Tyr Val Tyr Ile Arg Lys Val Pro Leu
625                 630                 635                 640

Asn Glu Ile Glu Met Ile Ser Thr Tyr Val Asp Leu Asn Ile Thr Leu
                645                 650                 655

Leu Glu Asp Arg Glu Phe Leu Pro Leu Glu Val Tyr Thr Arg Ala Glu
            660                 665                 670

Leu Glu Asp Thr Gly Leu Leu Asp Tyr Ser Glu Ile Gln Arg Arg Asn
        675                 680                 685

Gln Leu His Ala Leu Lys Phe Tyr Asp Ile Asp Ser Val Val Lys Val
    690                 695                 700

Asp Asn Asn Leu Ile Ile Met Arg Gly Met Leu Thr Phe Phe Gln Gly
705                 710                 715                 720

Leu Gly Asp Val Gly Ala Gly Phe Gly Lys Val Val Leu Gly Ala Ala
                725                 730                 735

Asn Ala Val Ile Ser Thr Val Ser Gly Ile Ser Ser Phe Leu Asn Asn
            740                 745                 750

Pro Phe Gly Ala Leu Ala Val Gly Leu Leu Ile Leu Ala Gly Leu Phe
        755                 760                 765

Ala Ala Phe Leu Ala Tyr Arg Tyr Val Ser Lys Leu Lys Ser Asn Pro
    770                 775                 780

Met Lys Ala Leu Tyr Pro Val Thr Thr Arg Asn Leu Lys Glu Ser Ser
785                 790                 795                 800

Lys Glu Lys Ile Gly Asp Gly Asp Glu Asp Gly Asp Glu Phe Asp Glu
                805                 810                 815

Asp Lys Leu Ser Gln Ala Lys Glu Met Ile Lys Tyr Met Thr Leu Ile
            820                 825                 830

Ser Ala Met Glu Lys Gln Glu His Lys Ala Met Lys Lys Asn Ser Gly
        835                 840                 845
```

```
Pro Ala Ile Leu Ala Asn Arg Val Ala Asn Leu Ala Leu Lys His Arg
    850                 855                 860

Gly Pro Lys Tyr Lys Arg Leu Lys Asn Met Asp Asp Glu Asn Asp Glu
865                 870                 875                 880

Val


<210> SEQ ID NO 16
<211> LENGTH: 2646
<212> TYPE: DNA
<213> ORGANISM: artificial sequence
<220> FEATURE:
<223> OTHER INFORMATION: gB DNA Z68147 encoding CAA92272

<400> SEQUENCE: 16

atgtatttaa ttactttagt atttttttatt aatattttgg ttatacaatg cgttccaaca     60

acacaaccta ctgaatctac accaccaatt actcctagtc caccaccgaa aaactcatct    120

tcgaacactg agttgaatga tgatatgaga gaaattttgg gcgaatcaca gattgaatct    180

gatgatacag caacattttt tatgtgtccg ccaccatctg gatcaacgtt ggtacgtttg    240

gaaccgcctc gggcttgtcc taattacaaa cttggtaaaa actttacaga aggtattgct    300

gtaatattta aagaaaatat atctccatat aaatttaagg ctaatattta ctataagaat    360

attattataa caactgtatg gtctggaagc tcgtatgccg tagtcactaa catgcatact    420

gatagagtac ctataaaggt tcaagaaatt acagaattga tcgatcgtag ggtatgtgc    480

ctctcaaagg ctgattatat tcgcaataat tacgagttta ctgcatttga taaagatgaa    540

gaccccagag aaatgcattt aaaaccctca aaatttaata cacccggttc tcgtggatgg    600

catacgacaa atgatacgta tacaaaaatt gggagtcctg gtttttatcg tacgggaaca    660

tctgtaaatt gtattgtcga agaagttgat gccagatctg tatatccata tgattccttt    720

ggcatttcaa ctggagatat aattcatatg tctccatttt ttggtttacg tgatggagct    780

catacagaac atactagcta ttcaaatgat cgatttcaac aaattgaggg ttattatcct    840

attgatttgg ataccagact acaagttggg ggaccagttt ccagaaactt tctcacaaca    900

caacatgtta ccgttgcatg gaactgggtt ccaaaaaattc gtgaggtgtg tacattggct    960

aaatggcggg aaattgatga gattattcgt gatgagtata aggggtctta tagatttaca   1020

gcaaaatcaa tttcagctac ctttatttcg gacgcaacac agtttgatat caaccgtgta   1080

aaactaagtg attgtgctaa acgtgaagca acagaggcta tcgataagat atataaaaat   1140

aaatataaca aaacccatat ccaaacagga gaacttgaaa cgtatctagc tagggggggg   1200

tttattattg catttagacc aatgattagc aatgagctag caaaattata tattaacgaa   1260

ttggcaagat ctgaacgtat tgttgatcta aatgcacttc ttaatccatc acattcagtt   1320

ggagggagga aaaaaaggtc aattgagaca gaaacccttg ggaggtcaaa acgtgatgtt   1380

gacggtggtg ttcaaaatgt caataatgca actctgatta aaacaacatc ttctattcat   1440

tttgctatgc ttcagtttgc gtacgatcat attcaatcgc atgtcaatga aatgcttagt   1500

agaattgcaa ccgcatggtg taatctccaa aataaagaga gaactctatg gaatgaggtt   1560

atgaaactta accctacaag catcacatca acaattatgg atcaaaaagt ttctgcaaga   1620

ctgctgggtg atgtaatcgc agttacacaa tgtgtcaata tttcaggttc taacgttttt   1680

attcaaaatt ctatgcgtgt taccggatct acaactacat gttacagtcg ccctttgata   1740

tcttttaaag cgcttgaaaa ctcaacagat tatatagagg gtcaactggg ggaaaataac   1800
```

```
gagttgttgg tagaccgtaa actaattgag ccgtgtacag ctaataataa gaggtatttt   1860

aaatttggtg tggattatgt atattttgaa aattatgttt atatccgtaa agtaccccta   1920

aatgaaattg aaatgattag tacatatgtt gatctcaaca tcacactgct tgaagatcga   1980

gaatttttac cattggaagt gtatacacga gcagaattgg aagatactgg cctgctagac   2040

tatagtgaaa ttcaacggag aaaccaactc cacgctctca aattttatga tatagacagt   2100

gttgttaaag ttgataacaa ccttataatt atgcgtggta tgctaacttt tttccaagga   2160

cttggagatg ttggagctgg ttttgggaaa gttgtattgg gtgctgcaaa cgcggttatt   2220

tcaactgttt ctgggatatc atctttcctt aacaacccat ttggagcact ggctgttggt   2280

ttgttgattt tagctggcct gtttgcagca tttttggcct accgatatgt ttctaaactt   2340

aaatcgaatc caatgaaagc tttgtaccct gtaacaacgc gaaacctgaa agaaagttca   2400

aaagaaaaaa ttggagatgg tgatgaagat ggtgatgaat ttgatgagga taaactctct   2460

caggcaaagg agatgattaa gtatatgacg ttaatctctg ctatggaaaa acaagagcat   2520

aaggcaatga aaaagaatag cggaccagcc attttggcta atcgtgttgc aaacctcgcc   2580

ctcaagcacc gcggaccaaa atataagcgt cttaaaaaca tggacgatga aaatgatgag   2640

gtttaa                                                              2646
```

<210> SEQ ID NO 17
<211> LENGTH: 374
<212> TYPE: PRT
<213> ORGANISM: artificial sequence
<220> FEATURE:
<223> OTHER INFORMATION: gD protein BAA44951

<400> SEQUENCE: 17

```
Met Met Thr Arg Leu His Phe Trp Trp Cys Gly Ile Phe Ala Val Leu
1               5                   10                  15

Lys Tyr Leu Val Cys Thr Ser Ser Leu Thr Thr Thr Pro Lys Thr Thr
            20                  25                  30

Thr Val Tyr Val Lys Gly Phe Asn Ile Pro Pro Leu Arg Tyr Asn Tyr
        35                  40                  45

Thr Gln Ala Arg Ile Val Pro Lys Ile Pro Gln Ala Met Asp Pro Lys
    50                  55                  60

Ile Thr Ala Glu Val Arg Tyr Val Thr Ser Met Asp Ser Cys Gly Met
65                  70                  75                  80

Val Ala Leu Ile Ser Glu Pro Asp Ile Asp Ala Thr Ile Arg Thr Ile
                85                  90                  95

Gln Leu Ser Gln Lys Lys Thr Tyr Asn Ala Thr Ile Ser Trp Phe Lys
            100                 105                 110

Val Thr Gln Gly Cys Glu Tyr Pro Met Phe Leu Met Asp Met Arg Leu
        115                 120                 125

Cys Asp Pro Lys Arg Glu Phe Gly Ile Cys Ala Leu Arg Ser Pro Ser
    130                 135                 140

Tyr Trp Leu Glu Pro Leu Thr Lys Tyr Met Phe Leu Thr Asp Asp Glu
145                 150                 155                 160

Leu Gly Leu Ile Met Met Ala Pro Ala Gln Phe Asn Gln Gly Gln Tyr
                165                 170                 175

Arg Arg Val Ile Thr Ile Asp Gly Ser Met Phe Tyr Thr Asp Phe Met
            180                 185                 190

Val Gln Leu Ser Pro Thr Pro Cys Trp Phe Ala Lys Pro Asp Arg Tyr
        195                 200                 205
```

```
Glu Glu Ile Leu His Glu Trp Cys Arg Asn Val Lys Thr Ile Gly Leu
    210                 215                 220

Asp Gly Ala Arg Asp Tyr His Tyr Tyr Trp Val Pro Tyr Asn Pro Gln
225                 230                 235                 240

Pro His His Lys Ala Val Leu Leu Tyr Trp Tyr Arg Thr His Gly Arg
                245                 250                 255

Glu Pro Pro Val Arg Phe Gln Glu Ala Ile Arg Tyr Asp Arg Pro Ala
            260                 265                 270

Ile Pro Ser Gly Ser Glu Asp Ser Lys Arg Ser Asn Asp Ser Arg Gly
        275                 280                 285

Glu Ser Ser Gly Pro Asn Trp Ile Asp Ile Glu Asn Tyr Thr Pro Lys
    290                 295                 300

Asn Asn Val Pro Ile Ile Ile Ser Asp Asp Asp Val Pro Thr Ala Pro
305                 310                 315                 320

Pro Lys Gly Met Asn Asn Gln Ser Val Val Ile Pro Ala Ile Val Leu
                325                 330                 335

Ser Cys Leu Ile Ile Ala Leu Ile Leu Gly Val Ile Tyr Tyr Ile Leu
            340                 345                 350

Arg Val Lys Arg Ser Arg Ser Thr Ala Tyr Gln Gln Leu Pro Ile Ile
        355                 360                 365

His Thr Thr His His Pro
    370
```

<210> SEQ ID NO 18
<211> LENGTH: 1125
<212> TYPE: DNA
<213> ORGANISM: artificial sequence
<220> FEATURE:
<223> OTHER INFORMATION: gD DNA D42113 encoding BAA44951

<400> SEQUENCE: 18

```
atgatgacac gtctacattt ttggtggtgt ggaatctttg cggtcctgaa atatctggta     60

tgtacttcaa gccttacgac cacgccaaaa acaactacgg tttatgtgaa gggatttaat    120

atacctccac tacgctacaa ttatactcaa gccagaatcg tgccaaaaat tccccaggcg    180

atggatccga agataacagc tgaagtacgt tatgtaacat caatggattc atgtgggatg    240

gtggcattga tatcagagcc ggatatagac gctactattc gaaccataca actatctcaa    300

aaaaaaacat ataacgcgac tataagttgg tttaaggtaa cccagggttg tgaataccct    360

atgtttctta tggatatgag actttgtgat cctaaacggg aatttggaat atgtgcttta    420

cggtcgcctt catattggtt ggaaccttta acaaagtata tgttcctaac agacgatgaa    480

ctgggtttga ttatgatggc cccggcccaa tttaatcaag gacaatatcg aagagttata    540

accatcgatg gttccatgtt ttatacagat tttatggtac aactatctcc aacgccatgt    600

tggttcgcaa aacccgatag atacgaagag attctacatg aatggtgtcg aaatgttaaa    660

actattggcc ttgatggagc tcgtgattac cactattatt gggtacccta taacccacaa    720

cctcaccata aagccgtact cttatattgg tatcggactc atggccgaga acccccagta    780

agattccaag aggccattcg atatgatcgt cccgccatac cgtctgggag tgaggattcg    840

aaacggtcca acgactctag aggagaatcg agtggaccca attggataga cattgaaaat    900

tacactccta aaaataatgt gcctattata atatctgacg atgacgttcc tacagcccct    960

cccaagggca tgaataatca gtcagtagtg atacccgcaa tcgtactaag ttgtcttata   1020

atagcactga ttctaggagt gatatattat attttgaggg taaagaggtc tcgatcaact   1080
```

-continued gcatatcaac aacttcctat aatacataca actcaccatc cttaa 1125

<210> SEQ ID NO 19
<211> LENGTH: 345
<212> TYPE: PRT
<213> ORGANISM: artificial sequence
<220> FEATURE:
<223> OTHER INFORMATION: gD protein AAB67058

<400> SEQUENCE: 19

```
Met Ile Lys Leu Leu Phe Ile Leu Phe Tyr Phe Asn Pro Ile Thr Gly
1               5                   10                  15

Tyr Lys Trp Val Asp Pro Pro Arg Arg Tyr Asn Tyr Thr Val Leu Arg
            20                  25                  30

Met Ile Pro Asp Ile Pro Asn Pro Met Asp Pro Ser Lys Asn Ala Glu
        35                  40                  45

Val Arg Tyr Val Thr Ser Thr Asp Pro Cys Asp Met Val Ala Leu Ile
    50                  55                  60

Ser Asn Pro Asn Ile Glu Ser Thr Ile Lys Thr Ile Gln Phe Val Gln
65                  70                  75                  80

Lys Lys Lys Phe Tyr Asn Ala Ser Leu Ser Trp Phe Lys Val Gly Asp
                85                  90                  95

Asp Cys Thr Tyr Pro Ile Tyr Leu Ile Gln Tyr Phe Asp Cys Asp Pro
            100                 105                 110

Gln Arg Glu Phe Gly Ile Cys Leu Lys Arg Ser Pro Asp Phe Trp Lys
        115                 120                 125

Pro Ser Leu Val Gly Tyr Thr Phe Leu Thr Asp Asp Glu Leu Gly Leu
    130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                165                 170                 175

Pro Arg Glu Thr Cys Tyr Phe Ser Lys Glu Asp Lys Phe Glu Pro Thr
            180                 185                 190

Phe Met Glu Trp Cys Lys Glu Ser Arg Ser Val Gly Ala Ser Lys Val
        195                 200                 205

Asp Asp Glu Leu Phe Tyr Leu Asn Arg Ala Gly Pro Gln Thr Leu Leu
    210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                245                 250                 255

Asn Asp Lys Phe Asp Asp Glu Leu Pro Ser Arg Pro His Ile Ser Asn
            260                 265                 270

Thr Ile Asn Lys Thr Ile Lys Glu Ile Val Asn Leu Glu Asp Tyr Phe
        275                 280                 285

Lys Asn Thr Asn Val Ile Asp Thr Thr Thr Pro Thr Pro Ile Asn Asn
    290                 295                 300

Thr Pro Lys Asn Ile Thr Val Gly Ile Val Ile Ile Ile Leu Ile Ile
305                 310                 315                 320

Leu Phe Ile Ile Gly Phe Phe Val Tyr Lys Arg Gln Lys Ile Tyr Asn
                325                 330                 335

Asn Tyr Lys Lys Leu Thr Thr Asn Val
            340                 345
```

<210> SEQ ID NO 20
<211> LENGTH: 1038
<212> TYPE: DNA
<213> ORGANISM: artificial sequence
<220> FEATURE:
<223> OTHER INFORMATION: gD DNA CHU8223 encoding AAB67058

<400> SEQUENCE: 20
atgattaaac ttctatttat cttattttat tttaacccaa taactggata taaatgggta 60
gaccctcctc gtaggtataa ttacaccgtt ttaagaatga ttccagatat tccaaatcca 120
atggatcctt ctaaaaacgc tgaagttcgg tatgtaactt ctactgaccc atgtgatatg 180
gttgctttga tttctaatcc aaatatagaa tctacaatta aaacgattca atttgtgcaa 240
aagaaaaaat tttacaatgc atctcttagt tggtttaaag ttggagatga ttgtacatat 300
ccaatatatt taattcaata ttttgattgt gatcctcaaa gagaatttgg catatgttta 360
aaaagatctc cagattttg gaaaccatcg ttagttggtt acacattttt aactgatgat 420
gaattgggat tagttttagc tgcccccgct ccatttaatc aaggtcaata tagacgggtt 480
attcaaattg aaaatgaagt tttttatact gattttatgg ttcaattacc acgagaaact 540
tgttattttt ctaaagaaga taaatttgaa ccaactttta tggaatggtg taaggaatct 600
agatctgtag gagcatcaaa agttgacgat gaacttttt atctaaatag agctggtccc 660
caaaccctgc ttaaatatta tgttattaaa gatttttata gacttaacgg tagagaacct 720
ccaataaaat ttaaagaagc tcttagatac gatataccat ataaagtgaa tgataaattt 780
gatgatgaat taccatcgag gccacatatt agtaatacta ttaataaaac tattaaagaa 840
attgtaaatc ttgaagatta ttttaaaaat acaaatgtta tagatactac taccccaaca 900
ccaataaata ataccccaaa aaatataacc gtgggaattg ttataattat attaataata 960
ctatttataa ttggattttt tgtttataaa agacaaaaaa tatataataa ttataaaaaa 1020
ttaacaacaa atgtttag 1038

<210> SEQ ID NO 21
<211> LENGTH: 345
<212> TYPE: PRT
<213> ORGANISM: artificial sequence
<220> FEATURE:
<223> OTHER INFORMATION: gD protein AAK51062

<400> SEQUENCE: 21

Met Ile Lys Leu Leu Phe Ile Leu Phe Tyr Phe Asn Pro Ile Thr Gly
1 5 10 15

Tyr Lys Trp Val Asp Pro Pro Arg Arg Tyr Asn Tyr Thr Val Leu Arg
20 25 30

Met Ile Pro Asp Ile Pro Asn Pro Met Asp Pro Ser Lys Asn Ala Glu
35 40 45

Val Arg Tyr Val Thr Ser Thr Asp Pro Cys Asp Met Val Ala Leu Ile
50 55 60

Ser Asn Pro Asn Ile Glu Ser Thr Ile Lys Thr Ile Gln Phe Val Gln
65 70 75 80

Lys Lys Lys Phe Tyr Asn Ala Ser Leu Ser Trp Phe Lys Val Gly Asp
85 90 95

Asp Cys Thr Tyr Pro Ile Tyr Leu Ile Gln Tyr Phe Asp Cys Asp Pro
100 105 110

Gln Arg Glu Phe Gly Ile Cys Leu Lys Arg Ser Pro Asp Phe Trp Lys
115 120 125

```
Pro Ser Leu Val Gly Tyr Thr Phe Leu Thr Asp Asp Glu Leu Gly Leu
    130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                165                 170                 175

Pro Arg Glu Thr Cys Tyr Phe Ser Lys Glu Asp Lys Phe Glu Pro Thr
            180                 185                 190

Phe Met Glu Trp Cys Lys Glu Ser Arg Ser Val Gly Ala Ser Lys Val
        195                 200                 205

Asp Asp Glu Leu Phe Tyr Leu Asn Arg Ala Gly Pro Gln Thr Leu Leu
    210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                245                 250                 255

Asn Asp Lys Phe Asp Asp Glu Leu Pro Ser Arg Pro His Ile Ser Asn
            260                 265                 270

Thr Ile Asn Lys Thr Ile Lys Glu Ile Val Asn Leu Glu Asp Tyr Phe
        275                 280                 285

Lys Asn Thr Asn Val Ile Asp Thr Thr Thr Pro Thr Pro Ile Asn Asn
    290                 295                 300

Thr Pro Lys Asn Ile Thr Val Gly Ile Val Ile Ile Ile Leu Ile Ile
305                 310                 315                 320

Leu Phe Ile Ile Gly Phe Phe Val Tyr Lys Arg Gln Lys Ile Tyr Asn
                325                 330                 335

Asn Tyr Lys Lys Leu Thr Thr Asn Val
            340                 345


<210> SEQ ID NO 22
<211> LENGTH: 1038
<212> TYPE: DNA
<213> ORGANISM: artificial sequence
<220> FEATURE:
<223> OTHER INFORMATION: gD DNA AF361076 encoding AAK51062

<400> SEQUENCE: 22

atgattaaac ttctatttat cttattttat tttaacccaa taactggata taaatgggta     60

gaccctcctc gtaggtataa ttacaccgtt ttaagaatga ttccagatat tccaaatcca    120

atggatcctt ctaaaaacgc tgaagttcgg tatgtaactt ctactgaccc atgtgatatg    180

gttgctttga tttctaatcc aaatatagaa tctacaatta aaacgattca atttgtgcaa    240

aagaaaaaat tttacaatgc atctcttagt tggtttaaag ttggagatga ttgtacatat    300

ccaatatatt taattcaata ttttgattgt gatcctcaaa gagaatttgg catatgttta    360

aaaagatctc cagatttttg gaaaccatcg ttagttggtt acacattttt aactgatgat    420

gaattgggat tagttttagc tgcccccgct ccatttaatc aaggtcaata tagacgggtt    480

attcaaattg aaaatgaagt tttttatact gattttatgg ttcaattacc acgagaaact    540

tgttattttt ctaaagaaga taaatttgaa ccaactttta tggaatggtg taaggaatct    600

agatctgtag gagcatcaaa agttgacgat gaactttttt atctaaatag agctggtccc    660

caaaccctgc ttaaatatta tgttattaaa gatttttata gacttaacgg tagagaacct    720

ccaataaaat ttaaagaagc tcttagatac gatataccat ataaagtgaa tgataaattt    780

gatgatgaat taccatcgag gccacatatt agtaatacta ttaataaaac tattaaagaa    840
```

-continued

```
attgtaaatc ttgaagatta ttttaaaaat acaaatgtta tagatactac taccccaaca    900

ccaataaata ataccccaaa aaatataacc gtgggaattg ttataattat attaataata    960

ctatttataa ttggattttt tgtttataaa agacaaaaaa tatataataa ttataaaaaa   1020

ttaacaacaa atgtttag                                                 1038


<210> SEQ ID NO 23
<211> LENGTH: 350
<212> TYPE: PRT
<213> ORGANISM: artificial sequence
<220> FEATURE:
<223> OTHER INFORMATION: gD protein CAC51465

<400> SEQUENCE: 23

Met Ile Gly Leu Ile Ile Phe Ile Phe Phe Tyr Asn Gly Asn Ile Ala
1               5                   10                  15

Ile Ala Tyr Asn Trp Ile Val Gln Pro Leu Arg Tyr Asn Tyr Thr Val
            20                  25                  30

Leu Asp Leu Arg Pro Asn Ile Pro Asn Pro Met Asp Ser Ser Lys Asn
        35                  40                  45

Ala Glu Val Arg Tyr Val Thr Ser Thr Asp Pro Cys Gly Met Val Ala
    50                  55                  60

Leu Ile Ser Glu Pro Asn Ile Glu Ser Thr Ile Lys Thr Ile Gln Phe
65                  70                  75                  80

Val Asn Lys Lys Lys Tyr Tyr Asn Ala Ser Leu Ser Trp Phe Lys Val
                85                  90                  95

Gly Asp Asp Cys Thr Tyr Pro Ile Tyr Leu Ile Lys Tyr Phe Asn Cys
            100                 105                 110

Asp Pro Gln Lys Glu Phe Gly Ile Cys Leu Lys Arg Thr Pro Asp Tyr
        115                 120                 125

Trp Lys Pro Ser Leu Ile Gly Tyr Ser Phe Leu Thr Asp Asn Glu Leu
    130                 135                 140

Gly Leu Val Phe Ala Ala Pro Ala Pro Phe Asn Gln Gly Gln Tyr Arg
145                 150                 155                 160

Arg Val Ile Ile Ile Glu Lys Glu Val Phe Tyr Thr Asp Phe Met Val
                165                 170                 175

Lys Leu Pro Lys Glu Thr Cys Pro Phe Pro Met Lys Asp Arg Val Glu
            180                 185                 190

Arg Asp Leu Pro Lys Trp Cys Lys Glu Ala Lys Glu Phe Gly Pro Leu
        195                 200                 205

Gly Thr Asp Glu Glu Ser Phe Tyr Leu Asn Arg Ala Val Pro Gln Pro
    210                 215                 220

Arg Leu Lys Tyr Tyr Val Ile Arg Glu Phe Tyr Arg Met Asn Gly Arg
225                 230                 235                 240

Glu Pro Pro Val Lys Phe Lys Glu Ala Leu Arg Tyr Asp Lys Pro Tyr
                245                 250                 255

Arg Phe Glu Lys Lys Thr Lys Glu Ser Gln Pro Lys Pro Thr Glu Ile
            260                 265                 270

Lys Ser Lys Val Ser Ser Glu Glu Glu Ser Lys Lys Leu Glu Glu Tyr
        275                 280                 285

Leu Lys Ile Ser Asp Val Asn Leu Ile Asp Gly Asn Ile Glu Thr Gln
    290                 295                 300

Leu Pro Ile Asn Asn Ser Lys Thr Asn Ile Thr Ile Ala Val Val Thr
305                 310                 315                 320
```

```
Ile Ile Ile Ile Ile Ile Leu Ser Ile Thr Gly Phe Phe Ile Tyr Arg
                325                 330                 335

Arg Arg Lys Tyr Asn Asn Tyr Lys Arg Leu Pro Val Asn Ile
            340                 345                 350


<210> SEQ ID NO 24
<211> LENGTH: 1053
<212> TYPE: DNA
<213> ORGANISM: artificial sequence
<220> FEATURE:
<223> OTHER INFORMATION: gD DNA AJ290955 encoding CAC51465

<400> SEQUENCE: 24

atgattggac ttataatttt tatttttttt tataatggaa atatagcgat tgcatataac      60

tggatcgttc aacctctcag atataattac accgtcctag atttgcgtcc aaatattcca     120

aatccaatgg attcatctaa aaatgcagaa gttaggtatg taacatctac agatccatgt     180

ggtatggttg ctttaatttc tgagccaaat atagaatcta caattaaaac tattcaattt     240

gtaaataaaa aaaaatatta taacgcttcg cttagttggt ttaaagttgg agatgattgt     300

acatatccaa tatacttaat taaatatttt aattgcgatc ctcaaaaaga gtttggtata     360

tgcttaaaaa gaacacccga ttattggaaa ccatcattga ttggttattc ttttttaaca     420

gataatgaat tgggactagt tttgctgct ccagctcctt tcaatcaagg acaatataga     480

cgtgttatta taatagaaaa ggaagttttt tatacagatt ttatggttaa attacccaaa     540

gaaacttgtc catttcccat gaaagatagg gttgaacgag atcttccaaa atggtgtaaa     600

gaagcaaaag agtttggacc gttgggaaca gatgaagagt cgttttatct gaatagagct     660

gttccacaac cacgacttaa atactatgtt attagggagt tctatagaat gaatggtaga     720

gaacctccag ttaaatttaa agaagctctt agatatgata aaccttatag atttgaaaaa     780

aaaacaaaag aatcacagcc aaaaccgact gaaataaaat caaaagtatc atcagaagag     840

gaaagtaaaa aacttgaaga atatttgaaa atttcagatg taaatttaat tgatggtaat     900

atagaaactc aattacctat aaataattcc aagacaaata taactatagc tgttgtaact     960

attataatta taataatttt atctataact ggattttta tttacagaag aaggaaatat    1020

aataattata aaagattacc agtaaatatt taa                               1053


<210> SEQ ID NO 25
<211> LENGTH: 20
<212> TYPE: DNA
<213> ORGANISM: artificial sequence
<220> FEATURE:
<223> OTHER INFORMATION: primer FR09

<400> SEQUENCE: 25

cgcagctgca atcaattcag                                                  20


<210> SEQ ID NO 26
<211> LENGTH: 20
<212> TYPE: DNA
<213> ORGANISM: artificial sequence
<220> FEATURE:
<223> OTHER INFORMATION: primer FR10

<400> SEQUENCE: 26

tgggtggaca gggatctgct                                                  20


<210> SEQ ID NO 27
<211> LENGTH: 15186
```

<212> TYPE: DNA
<213> ORGANISM: artificial sequence
<220> FEATURE:
<223> OTHER INFORMATION: AVINEW NDV genome sequence

<400> SEQUENCE: 27
accaaacaga gaatccgtga ggtacgatag aaggcgaagg agcaatcgaa gtcgtacggg 60
tagaaggtgt gaatctcgag tgcgagcccg aagctcaaac tcgagagagc cttctgccaa 120
aatgtcttct gtattcgatg agtacgagca gctcctcgcg gctcagactc gccccaatgg 180
agctcatggc ggaggagaga aggggagcac cttaaaggta gaagtcccgg tattcactct 240
caacagtgat gacccagaag atagatggaa ctttgcagtg ttttgtcttc ggattgctgt 300
tagcgaggat gccaacaaac cacttaggca aggtgctctc atatctctct tatgttccca 360
ctctcaagtg atgaggaacc atgttgccct tgcggggaaa cagaatgagg ccacactggc 420
tgttcttgag atcgatggtt ttaccaacgg cgtgccccag ttcaacaaca ggagtggagt 480
gtctgaagag agagcacaga gatttatgat gatagcaggg tctctccctc gggcatgcag 540
caacggtacc ccgttcgtca cagctggggt tgaagatgat gcaccagaag acattactga 600
taccctggag aggatcctct ctatccaggc tcaagtatgg gtcacggtgg caaaggccat 660
gactgcatat gagacagcag atgagtcaga aacaagaaga atcaataagt acatgcagca 720
aggcagggtc cagaagaagt acatcctcca ccccgtatgc aggagcgcaa tccaactcac 780
aatcagacag tctctggcgg tccgcatctt tttggttagc gagcttaaga gaggccgcaa 840
cacggcaggt gggacctcca cctattacaa cttggtgggg gatgtagact catacatcag 900
gaacactggg ctaactgcat tcttcctgac acttaaatat ggaattaaca ccaagacatc 960
agcccttgca cttagcagcc tctcaggcga tatccagaaa atgaagcagc tcatgcgctt 1020
gtatcggatg aaaggagata atgcgccgta catgacattg ctcggtgaca gtgaccagat 1080
gagctttgca cctgccgagt atgcacaact ttactccttt gccatgggta tggcatcagt 1140
cctagataaa ggaactagca aataccaatt tgccagggac tttatgagca catcattctg 1200
gagacttgga gtagagtacg ctcaggctca aggaagtagc atcaatgagg atatggccgc 1260
cgagctaaag ctaaccccag cagcaaggag aggcctggca gctgctgccc aaagagtgtc 1320
tgaggagacc agcagcatgg acatgcccac ccaacaagcc ggggtcctca ctggactcag 1380
cgacggaggc tcccaagccc cccaaggtgc actgaacaga tcacaagggc aaccggacac 1440
cggggatggg gagacccaat ttctggatct gatgagagcg gtggcaaata gcatgagaga 1500
agcgccaaac tctgcgcagg gcacccctca accggggcct cccccaaccc ctgggccctc 1560
tcaagacaat gacaccgact gggggtactg accgacagca cccagtttgc ttctatgagg 1620
tcatcccaat tcctctgccc acaccccacc cctcaatccg caatcccgca tggccaaacc 1680
cacaaacgaa ccccccctgtc tccctcctct cccccagccc cacaacccca cctgcccagg 1740
gcaacatagg tacaatgcga cccactaata atcaatacag ggccaaagaa attagaaaaa 1800
agtacgggta gaagggagac attcagagat cagggcgagt cacccgggtc tctgctctcc 1860
cttctaccta gtggattagg atggagatgg ccacctttac agatgcggag atcgacgagc 1920
tatttgagac cagtggaact gtcattgaca gcataattac ggcccaggga aaaccagtag 1980
agactgttgg aaggagtgca atcccacaag gcaaaactaa ggctttgagc gcagcatggg 2040
agaagcatgg gagcatccag tcaccagcca gccaagacac ccctgatcga caggacagat 2100
cagataaaca actgtccaca cccgagcaag cgagtccaaa cgacagcccc ccagccacat 2160

-continued

```
ccactgacca gcctcccact caggctgcag atgaggccgg cgatacacag ctcaagaccg   2220
gagcaagcaa ctctctgctg tcgatgcttg ataaactcag caataagtca tctaatgcta   2280
aaaagggccc agggtcgagc cctcaagaaa ggcatcatca acgtctgact caacaacagg   2340
ggagtcaaca aagccgcgga aacagccaag agagaccgca gaaccaggcc aaggccatcc   2400
ctggaaacca ggtcacagac gcgaacacag catatcatgg acaatgggag gagtcacaac   2460
tatcagctgg tgcaacccat catgctctcc gatcagagca gagccaagac aatactcctg   2520
cacctgtgga tcatgtccag ctacctgtcg actttgtgca ggcgatgatg tctatgatgg   2580
aggcgatatc acagagggta agtaaagttg actatcagct ggaccttgtc ttgaaacaga   2640
catcttctat ccccatgatg cggtctgaaa tccagcagct gaaaacgtct gttgcggtca   2700
tggaagccaa tttgggcatg atgaagatcc tggaccctgg ttgtgccaac gtttcatctc   2760
taagtgatct acgggcagtt gcccgatccc acccggtttt aatttctggc cccggagacc   2820
catctcctta tgtgacccaa gggggcgaaa tggcactcaa taaactttcg caaccggtgc   2880
aacacccctc tgaattgatt aaacccgcca cggcaagcgg gcctgatata ggagtggaga   2940
aagacactgt ccgtgcattg atcatgtcac gccctatgca tccgagctct tcagctaggc   3000
tcttgagcaa actggacgca gccggatcga ttgaggaaat cagaaaaatc aagcgccttg   3060
cactgaatgg ctaatcacca ccgcaacccg cagcagatcc ctgtccaccc agcaccacac   3120
ggtatctgca ccaagctcct ctctgcaaac ccaaggtcca acaccccgag cgacaaccct   3180
gtcctgcttc ctctgcccca ctaaatgatc gcgcagctgc aatcaattca gctatattaa   3240
ggattaagaa aaaatacggg tagaatcgga gtgccccgat tgtgccaaga tggactcatc   3300
taggacaatc gggctgtact ttgattctac ccttccttct agcaacctgc tagcattccc   3360
gatagtccta caagacacag gggacgggaa gaagcaaatc gccccgcaat acaggatcca   3420
gcgtcttgac tcgtggacag acagcaaaga agactcggta ttcatcacca cctatggatt   3480
catctttcag gttgggaatg aagaagccac tgtcggcatg atcaatgata atcccaagcg   3540
cgagttactt tccactgcca tgctatgcct agggagtgta ccaaatgtcg gagatcttgt   3600
tgagctggca agggcctgcc tcactatggt ggtaacatgc aagaagagtg caactaacac   3660
cgagagaatg gtcttctcag tagtgcaggc accccaggtg ctgcaaagct gtagggttgt   3720
ggcaaacaaa tactcgtcgg tgaatgcagt caagcacgtg aaagcaccag agaagattcc   3780
tgggagcgga accctagagt acaaagtgaa ctttgtctct ctgaccgtgg tgccaagaaa   3840
ggacgtctac aagataccaa ctgcagcact taaggtctct ggctcaagtc tgtacaatct   3900
tgcgctcaat gtcactattg atgtggaggt agacccgaag agcccgttgg tcaaatccct   3960
ttccaagtcc gacagtgggt actatgctaa tctcttctta catattgggc ttatgtccac   4020
tgtagataag aaggggaaga aagtgacatt tgacaagctg gaaaggaaga taaggagact   4080
tgatctatct gtagggctta gtgacgtgct cggaccttcc gtgcttgtaa aggcgagagg   4140
tgcacggact aagctgctgg cacctttctt ctctagcagt gggacagcct gctatcccat   4200
agcaaatgcc tctcctcagg tggccaagat actctggagc caaaccgcgt acctgcggag   4260
tgtaaaagtc attatccaag cgggcaccca gcgtgctgtc gcagtgaccg ccgaccacga   4320
ggttacctct actaagctgg agaaggggca taccattgcc aaatacaatc ccttcaagaa   4380
ataggctgca tctctgagat tgcactccgc ccatcttccc ggatcaccat gacactaaat   4440
aatgatctgt cttgattact tatagttagt tcgcctgtct atcaaattag aaaaaacacg   4500
ggtagaagat tctggatccc ggttggcgcc ttcaaggtgc aagatgggct ccagatcttc   4560
```

```
taccaggatc ccagtacctc ttatgctgac cgtccgagtc atgttggcac tgagttgcgt   4620
ctgtccgacc agcgcccttg atggcaggcc tcttgcagct gcagggattg tggtaacagg   4680
agacaaagca gtcaacatat acacctcatc tcagacaggg tcaatcataa tcaagttact   4740
cccaaatatg cccaaggata aagaggcgtg tgcaaaagcc ccgttggagg catacaacag   4800
gacattgact actttgctca cccccccttgg tgattctatc cgtaggatac aagagtctgt   4860
gaccacgtcc ggaggaggga aacagggacg tcttataggc gccattatcg gtggtgtagc   4920
tctcggggtt gcaaccgctg cacagataac agcagcctcg gctctgatac aagccaatca   4980
aaatgctgcc aacatactcc ggctaaaaga gagcattgct gcaaccaatg aggctgtgca   5040
cgaggtcact aatggattat cacaactagc agtggcagtt gggaagatgc agcaatttgt   5100
taatgaccag tttaataaaa cagctcagga attggactgt ataaaaatta cacagcaggt   5160
tggtgtagaa ctcaacctgt acctaactga attgactaca gtattcgggc cacaaatcac   5220
ttcccctgcc ttaactcagc tgactatcca ggcgctttac aatctagctg gtgggaatat   5280
ggattacttg ttgactaagt taggtgtggg gaacaaccaa ctcagctcat taattagtag   5340
tggcctgatc accggcaacc ctattctgta cgactcacag actcaactct tgggtataca   5400
ggtaacccta ccctcagtcg ggaacctaaa taatatgcgt gccacctacc tggaaacctt   5460
gtctgtaagt acaaccaaag gatttgcctc agcacttgtc ccaaaagtag tgacacaggt   5520
cggttccgtg atagaagagc ttgacacctc gtactgtata gagaccgatt tggatctata   5580
ttgtacaaga atagtgacat tccctatgtc tcctggtatt tattcctgtt tgagtggcaa   5640
tacatctgct tgcatgtact caaagactga aggcgcactc actacgccgt atatgaccct   5700
caaaggctca gttattgcta actgtaagat gacaacatgt agatgtgcag accccccggg   5760
tatcatatcg caaaattatg gagaagctgt gtctctaata gataggcaat catgcaatat   5820
cttatcctta gacgggataa ctttgaggct cagtggggaa tttgatgcaa cttatcaaaa   5880
gaatatctca atacaagatt ctcaagtaat agtgacaggc aatcttgata tctcgactga   5940
gcttgggaat gtcaacaact cgataagtaa tgctttggat aagttagagg aaagcaacag   6000
caaactagat aaggtcaatg tcaaactgac cagcacatcc gctcttatta cctatatcgt   6060
tttaactgtc atatctcttg tatgtggtat acttagcctg gttctagcat gctacctgat   6120
gtacaagcaa aaggcgcaac agaagacctt gttgtggctt gggaataata ccctagacca   6180
gatgagggcc actacaaaaa tgtgaatgcg gatgagaggc agaaacatcc ccaatagcag   6240
tttgtgtgta aagtctgaca gcctgttaat tagaagaatt aagaaaaaac taccggatgt   6300
agatgaccaa agggcgatat acgggtagaa cggtcgggga ggccgtccct caatcgggag   6360
ccgggcctca caacatccgt tctaccgcat caccaatagc agttttcagt catggaccgc   6420
gcagttagcc aagttgcgct agagaatgat gaaagagagg caaagaatac atggcgcttg   6480
gtattccgga tcgcaatcct actctcaacg gtggtgacct tagccatctc tgcagccgcc   6540
cttgcatata gcatggaggc cagcacacct agcgatcttg taggcatacc gactgcgatc   6600
tctagagcag aggaaaagat tacatctgca ctcggttcca atcaagatgt agtagatagg   6660
atatataagc aggtggccct cgaatctcca ctggcattgc taaacaccga atctacaatt   6720
atgaacgcaa taacgtctct ctcttatcga atcaatgggg ccgcaaatag cagcggatgt   6780
ggagcaccca ttcatgatcc agattatatt ggaggaatag gtaaagaact tattgtagat   6840
gatgctagcg acgtcacatc atactatccc tctgcgttcc aagaacacct gaactttatc   6900
```

```
ccggcgccta ctacaggatc aggttgcact cggataccct catttgacat gagcgctacc   6960
cactactgtt atactcacaa tgtgatatta tctggctgca gagatcactc gcactcacat   7020
caatatttag cacttggtgt gcttcggaca tctgcaacag ggagggtatt cttttccact   7080
ctgcgttcca tcaatctgga tgacacccaa aatcggaagt cttgcagtgt gagtgcaacc   7140
cccttgggtt gtgatatgct gtgctctaaa gtcacagaga ctgaagaaga ggattataac   7200
tcagctatcc ccacgtcgat ggtacatgga aggttagggt tcgacggcca ataccacgag   7260
aaggacctag atgtcacaac actattcgag gactgggtgg caaactaccc aggagtaggg   7320
ggcgggtctt ttattgacaa ccgcgtatgg ttcccagttt acggagggct aaaacccaat   7380
tcgcccagtg acaccgcaca agaagggaaa tatgtaatat acaagcgata caatgacaca   7440
tgtccagatg agcaagatta tcagattcaa atggctaagt cttcatataa gcctgggcgg   7500
tttggaggga aacgcgtaca gcaggccatc ttatctatca aagtgtcaac atccttgggc   7560
gaggacccgg tactgactgt accgcccaac acagtaacac tcatgggggc cgaaggcaga   7620
gttctcacag tagggacatc tcatttcctt tatcagcgag ggtcatcata cttctcccct   7680
gccctactat atcctatgat agtcagcaac aaaacagcca ctcttcatag tccttataca   7740
ttcaatgcct tcactcgacc aggtagtgtc ccttgccagg cttcagcaag atgccctaac   7800
tcatgtgtta ccggagtcta tactgatcca tatcccttgg tcttctatag gaaccacacc   7860
ttgcgagggg tattcgggac gatgcttgat gataaacaag caagactcaa ccctgtatct   7920
gcagtatttg acagcatatc ccgcagtcgc ataacccggg tgagttcaag cagcaccaag   7980
gcagcataca caacatcaac atgttttaaa gttgtaaaga ccaataaaac ctattgtctc   8040
agcattgccg aaatatccaa taccctcttc ggggaattca gaatcgtccc tttactagtt   8100
gagattctca aggatgatgg ggttagagaa gccaggtcta gccggttgag tcaactgcga   8160
gagggttgga aagatgacat tgtatcacct atcttttgcg acgccaagaa tcaaactgaa   8220
taccggcgcg agctcgagtc ctacgctgcc agttggccat aatcagctag tgctaatgtg   8280
attagattaa gtcttgtcgg tagtcacttg attaagaaaa aatgtgggtg gtagcgggat   8340
ataaggcaaa acaactcaag gaggatagca cgggtaggac atggcgagct ccggtcccga   8400
gagggcggag catcagatta tcctaccaga gtcacacctg tcttcaccat tagtcaagca   8460
caaactactc tattactgga aattaactgg gctaccactc cctgacgagt gtgacttcga   8520
ccacctcatt ctcagccgac aatggaagaa aatacttgaa tcggcctccc ctgacactga   8580
gagaatgata aaacttggaa gggcagtgca ccagactctc aaccacaatt ccaagataac   8640
cggagtactc catcccaggt gtttagaaga attggctagt attgaggttc ctgactcaac   8700
caacaagttt cggaagatcg agaagaaaat ccaaattcac aacacaaggt atggagaact   8760
gttcacaaga ctgtgcacgc atgtagagaa gaaattgttg ggatcatctt ggtctaataa   8820
tgtcccccgg tcagaagagt tcaacagcat ccgtacagat ccggcattct ggtttcactc   8880
aaaatggtcc acaactaagt ttgcatggct ccatataaaa cagattcaaa ggcatctgat   8940
tgtggcagca agaacaaggt ccgcagccaa caaattggtg acgctgaccc ataaggtagg   9000
ccaagtcttt gttactcctg agcttgtcat tgtgacacat acagatgaga acaagttcac   9060
gtgtcttacc caggaacttg tgttgatgta tgcagatatg atggagggca gagatatggt   9120
caacataata tcatccacgg cggcacatct caggagccta tcagagaaaa ttgatgacat   9180
tctgcggtta gtagatgccc tggcaaaaga tctgggtaat caagtctacg atgttgtagc   9240
actcatggag ggatttgcat acggcgccgt ccagctgctt gagccgtcag gtacattcgc   9300
```

aggggatttc ttcgcattca acctgcagga gctcaaagac actttgatcg gcctccttcc 9360
taaggatata gcagaatctg tgactcacgc aatagccact gtattctctg gcttagaaca 9420
aaatcaagcg gctgagatgc tgtgcctgtt gcgtctatgg ggccacccat tacttgagtc 9480
ccgtattgcg gcaaaagcag taaggagcca aatgtgcgca ccaaaaatgg tagactttga 9540
tatgatcctc caggtattgt ctttctttaa aggaacaatc atcaacggat acagaaagaa 9600
gaatgcaggt gtttggccac gtgtcaaagt agatacgata tacgggaagg tcattgggca 9660
gctacacgct gattcagcgg agatttcaca cgatatcatg ttgagagagt acaagagttt 9720
atctgcgctt gaattcgagc catgtataga atacgaccct atcaccaatc tgagcatgtt 9780
tctaaaagac aaggcgatcg cacacccgaa agacaactgg ctcgccgcgt ttaggcgaaa 9840
ccttctctct gaggaccaga agaaacatgt aaaggaggca acctctacta accgtctctt 9900
gatagagttc ttagagtcaa atgattttga tccatataag gagatggaat atctgacgac 9960
ccttgagtac ctaagagatg acaatgtggc agtatcatac tcgctcaagg agaaggaagt 10020
gaaggttaat gggcggattt ttgctaagct aacaaagaaa ttaaggaact gtcaagtgat 10080
ggcggaaggg atcttagctg accagattgc acctttcttt caagggaatg gggtcattca 10140
ggatagcata tctttaacca agagtatgct agcgatgagt caattgtctt tcaacagcaa 10200
taagaaacgt atcactgact gcaaagaaag agtagcctca aaccgcaatc acgatcaaaa 10260
gagcaagaat cgtcggagag ttgccacttt tataacgact gacctgcaaa agtactgtct 10320
taattggaga tatcagacaa tcaaactgtt cgctcatgcc atcaatcagc tgatgggctt 10380
acctcacttc ttcgaatgga ttcatctaag actaatggat actacgatgt ttgtaggaga 10440
ccctttcaat cccccaagtg acccaactga ctgtgatctc tcaagagtcc caaatgatga 10500
catatatatt gtcagtgcta gagggggtat tgagggatta tgtcagaagc tatggacaat 10560
gatctcaatt gctgcaatcc aacttgctgc agcaagatca cattgtcgcg tcgcctgtat 10620
ggtacagggt gacaatcaag taatagctgt aacgagagag gtaaggtcag atgactcccc 10680
ggaaatggtg ttaacacaat tgcatcaagc cagtgataat ttcttcaagg aattgattca 10740
tgttaatcat ttgattggcc ataatttgaa ggatcgtgaa acaatcagat cagacacatt 10800
cttcatatac agcaaacgaa tattcaaaga tggagcaata ctcagtcaag tcctcaaaaa 10860
ttcatctaaa ttagtgctaa tatcaggcga ccttagtgaa aacaccgtaa tgtcctgtgc 10920
caacattgca tctactatag cacggctgtg cgagaacggg cttccaaagg atttctgtta 10980
ttacttaaac tacctgatga gttgcgtgca gacatacttt gattctgagt tttccatcac 11040
taacagctcg caccccgatt ctaaccagtc gtggattgaa gacatctctt ttgtgcactc 11100
atatgtcctg acccctgccc agctaggggg actgagcaac ctccaatact caaggctcta 11160
cacgaggaac atcggtgacc cgggaactac tgcttttgca gagatcaagc gattagaagc 11220
agtggggtta ctaagtccta gtattatgac taacatctta actaggccgc ctggaaatgg 11280
agattgggcc agtctgtgta acgaccctta ctctttcaat tttgagactg tcgcgagtcc 11340
aaatattgtc cttaagaaac atacacaaag agtcctattt gaaacttgtt caaatccctt 11400
attatctggc gtgcatacag aggataatga ggcagaagag aaggcgttgg ctgaattttt 11460
actcaatcaa gaagtaattc atccacgtgt cgcacatgct atcatggaag caagctctat 11520
aggtaggagg aagcagattc aagggcttgt tgacacaaca aacaccgtaa tcaagattgc 11580
attgactagg aggccacttg gcatcaagag gctgatgcgg atagttaact actcgagcat 11640

-continued gcatgcaatg ctgtttagag acgatgtttt ctcatctaac aggtctaacc accccttagt 11700
ttcctctaat atgtgttctc tgacgctagc agactatgca cggaatagaa gctggtcacc 11760
attgacgggg ggtagaaaga tactgggtgt atctaatcct gatactatag aacttgtaga 11820
gggtgagatc cttagcgtca gcggaggatg cacaagatgt gacagcggag atgaacaatt 11880
cacttggttc catcttccga gcaatataga actgaccgat gacaccagca agaatcctcc 11940
gatgagagtg ccgtacctcg ggtcaaagac tcaagagagg agggccgcct cgcttgcgaa 12000
aatagctcat atgtcaccac atgtgaaagc tgctctaagg gcatcatccg tgttgatctg 12060
ggcttatgga gacaacgaag taaattggac tgctgctctt aaaattgcaa gatctcggtg 12120
caatataaac tcagagtatc ttcgactatt gtccccctta cccacagctg ggaatctcca 12180
acatagactg gatgacggca taactcagat gacattcacc cctgcatctc tctacagggt 12240
gtcaccttat attcacatat ccaatgattc tcaaaggtta ttcacggaag aaggagtcaa 12300
agagggaaat gtagtttatc agcaaatcat gctcttgggt ttatctctaa tcgaatcact 12360
cttcccgatg acgacaacca ggacatacga tgagatcaca ttgcacctcc acagtaaatt 12420
tagctgctgt atcagggaag caccggttgc agttcctttc gagttactcg ggatggcacc 12480
agaactaagg acagtgacct caaataagtt tatgtatgat cctagtcctg tatcggaggg 12540
tgactttgcg agacttgact tagctatctt taagagttat gagcttaatc tagaatcata 12600
tcccacaata gagctaatga acattctttc aatatccagc gggaagttaa tcggccagtc 12660
tgtggtttct tatgatgaag atacctccat aaagaatgac gccataatag tgtatgacaa 12720
cacccggaat tggatcagcg aagctcagaa ttcagatgtg gtccgcctat tcgagtatgc 12780
agcacttgaa gtgcttctcg actgttctta tcagctctac tatctgagag taagaggcct 12840
agacaatatc gtgttgtata tgagtgactt atataagaat atgccaggaa ttctactttc 12900
caacattgca gctacaatat ctcatcccat cattcattca agattgcatg cagtaggcct 12960
ggtcaatcac gacgggtcac accaacttgc agacacagat ttcatcgaaa tgtctgcaaa 13020
actattagtc tcttgcactc gacgcgtggt ctcaggttta tatgcaggga ataagtatga 13080
tctgctgttc ccgtctgtct tagatgataa cctgagtgag aagatgcttc agctgatatc 13140
tcggttatgc tgcctgtata cggtgctctt tgctacaaca agagagatcc cgaaaataag 13200
aggcttatct gcagaagaga agtgttcagt acttactgag tacctactgt cagatgctgt 13260
gaaaccatta cttagttctg agcaagtgag ctctatcatg tctcctaaca tagttacgtt 13320
cccagctaat ctatattaca tgtctcggaa gagccttaat ttgattaggg aaagagagga 13380
cagggacact atcttggcat tgttgttccc ccaagagcca ctacttgagt tccccttagt 13440
acaagatatt ggcgctcgag tgaaagatcc attcacccga caacctgcgg cgtttttaca 13500
agaattagat ttgagcgctc cagcaaggta tgacgcattt acacttagtc aggttcattc 13560
tgaacacaca tcaccaaatc cggaggacga ctacttagta cgatacctgt tcagaggaat 13620
agggaccgcg tcctcctctt ggtataaggc atctcacctt ctttctgtac ctgaggtcag 13680
atgtgcaagg cacgggaatt ccttatactt ggcagaagga agcggagcca ttatgagtct 13740
tctcgaactg catgtgccgc atgagactat ctattacaat acgctcttct caaacgagat 13800
gaaccccccca cagcggcatt tcggaccgac cccaacacag tttctgaatt cagttgttta 13860
taggaatcta caggcggagg taccatgtaa ggatggattt gtccaggagt tccgtccatt 13920
atggagagag aatacagaag aaagcgatct gacctcagat aaagcagtgg gttacatcac 13980
atctgcagtg ccctaccggt ctgtatcatt gctgcactgt gacattgaga ttcctccagg 14040

-continued

```
atccaatcaa agcttactgg atcaactggc taccaatctg tctctgattg ccatgcattc  14100

tgtaagggag ggcggggtcg tgatcatcaa agtgttgtat gcaatgggat attacttcca  14160

tctactcatg aacttgttca ctccgtgttc tacgaaagga tatattctct ctaatggcta  14220

tgcatgtaga ggggatatgg agtgttacct ggtatttgtc atgggctatc gaggtgggcc  14280

tacatttgta catgaggtag tgaggatggc aaaaactcta gtgcagcggc acggtacact  14340

tttgtccaaa tcagatgaga tcacactgac taggttattt acctcacagc ggcagcgtgt  14400

aacagacatc ctatccagtc ctttaccgag actaataaag ttcttgagaa agaatatcga  14460

tactgcgcta attgaagccg gggacaacc cgtccgtcca ttctgtgcag agagcttggt  14520

gaggacacta gcggacacaa ctcagatgac ccagatcatc gctagtcaca ttgacacagt  14580

cattcgatct gtgatctaca tggaggctga gggtgatctc gccgacacag tgttcttatt  14640

taccccctac aatctctcta cagacggtaa aaagagaaca tcacttaaac agtgcacaag  14700

gcagatctta gaggtcacaa tattgggtct tagagttgaa aatctcaata aagtaggtga  14760

tgtagtcagt ctagtactta aaggtatgat ttctctggag gacctgatcc ctctaagaac  14820

atacttgaag cgtagtacct gccctaagta tttgaagtct gttctaggta ttactaaact  14880

caaagaaatg tttacagaca cctctttatt atacttgact cgtgctcaac aaaaattcta  14940

catgaaaact ataggcaacg cagtcaaggg atactacagt aactgtgact cttaaagata  15000

atcacatatt aataggctcc ttttctagtt aactgagccc ttgttgattt aatgatacta  15060

tattagaaaa aagttgcact ccgatccttt aggactcgtg ttcgaattca aataattgtc  15120

ttagaaaaaa gttgcgcgta attgttcttg aatgtagtct tgtcattcac caaatctttg  15180

tttggt                                                          15186
```

NEWCASTLE DISEASE VIRUS VECTORED HERPESVIRUS VACCINES

CROSS-REFERENCE TO RELATED APPLICATIONS

This application is a continuation application of U.S. application Ser. No. 13/220,196 filed on Aug. 29, 2011, which claims benefit of U.S. provisional application Ser. No. 61/378,575 filed Aug. 31, 2010.

FIELD OF THE INVENTION

The present invention encompasses NDV-vectored herpesvirus vaccines or compositions.

BACKGROUND OF THE INVENTION

Several studies in recent years have highlighted the potential of Newcastle disease virus (NDV) to be used as a vaccine vector for avian diseases (Krishnamurthy et al., Virology 278, 168-182,2000; Huang et al., J. Gen. Virol. 82, 1729-1736, 2001; Nakaya et al., J. Virol. 75, 11868-11873, 2001; Park et al. PNAS 103, 8203-8208, 2006; Veits et al PNAS 103, 8197-8202, 2006; Ge et al. J. Virol. 81, 150-158, 2007; Romer-Oberdorfer et al. Vaccine 26, 2307-2313, 2008).

NDV belongs to the Paramyxovirinae family and the Avulavirus genus. NDV replicates in respiratory and gastrointestinal tracts, in the oviduct, and for some isolates, in the nerve system. The transmission is aerogenic and by oral and fecal routes. NDV causes a highly contagious and fatal disease affecting all species of birds, and can infect some mammalian species. The disease can vary from clinically unapparent to highly virulent forms, depending on the virus strain and the host species. The continuous spectrum of virulence displayed by NDV strains enabled the grouping of them into three different pathotypes: lentogenic, mesogenic, and velogenic (Alexander, D. J., Diseases of Poultry, Iowa State Uni. Press, Ames Iowa, 541-569, 1997). Lentogenic strains do not usually cause disease in adult chickens and are widely used as live vaccines in poultry industries in the United States and other countries. Viruses of intermediate virulence are termed mesogenic, while viruses that cause high mortality are termed velogenic. The disease has a worldwide distribution and remains a constant major threat to commercial poultry production.

The NDV genome is a non-segmented negative strand of RNA of approximately 15 kb. The genomic RNA contains six genes that encode the following proteins in the order of: the nucleocapsid protein (NP), phosphoprotein (P), matrix protein (M), fusion protein (F), haemagglutinin-neuramimidase (HN) and large polymerase protein (L). Two additional proteins, V and W, of unknown function are produced by RNA editing during P gene transcription (Steward et al., 1993, Journal of General Virology 74:2539-2547).

The development of methods to recover non-segmented negative RNA viruses entirely from cloned cDNA, established in recent years, opened up the possibility of genetically manipulating this virus group, including NDV (Conzelmann, K. K., Ann. Rev. Genet. 32, 123-162, 1998; Roberts and Rose, Virology 247, 1-6, 1998). This unique molecular genetic methodology, termed "reverse genetics", provides a means not only to investigate the functions of various virus-encoded genes (Palese et al., PNAS 93, 11354-11358, 1996; Nagai, Y., Rev. Med. Virol. 9, 83-99, 1999) but also to allow the use of these viruses to express heterologous genes (Bukreyev et al., J. Virol. 70, 6634-6641, 1996; Mebatsion et al., PNAS 93, 7310-7314, 1996; Schnell et al., PNAS 93, 11359-11365, 1996; Hasan et al., J. Gen. Virol. 78, 2813-2820, 1997; He et al., Virology 237, 249-260, 1997; Sakai et al., FEBS Lett. 45, 221-226, 1999). This provides a new method of generating improved vaccines and vaccine vectors. Recently, NDV was used as a vector for expression of avian influenza antigens (US2010/0255029, Merial Limited).

The Herpesvirus glycoprotein D (gD) is essential for FHV-1 (Feline Herpesvirus-1) entry and is involved in interaction with host cell (binding to receptors). The gD protein has haemagglutination activities on feline red blood cells (Maeda et al., Virology 202, 1034-8, 1994; Maeda et al., Virus Res. 46, 75-80, 1996). The Herpesvirus glycoprotein B (gB) is essential for FHV entry and is involved in fusion process (Spatz and Maes, Virology 197, 125-36, 1993; Maeda et al., Virus Res 39, 55-61, 1995). Both glycoproteins can induce neutralizing antibodies (Horimoto et al., Arch Virol 111, 127-32, 1990).

Considering the susceptibility of animals, including humans, to herpesvirus, a means of preventing herpesvirus infection and protecting animals is essential. Accordingly, there is a need for an effective vaccine against herpesvirus.

Citation or identification of any document in this application is not an admission that such document is available as prior art to the present invention.

SUMMARY OF THE INVENTION

The present invention relates to an NDV-vectored vaccine or composition that comprises one or more engineered, recombinant NDV vectors that harbor and express certain herpesvirus antigens, such as a feline herpesvirus antigen, and optionally a pharmaceutically or veterinarily acceptable carrier, adjuvant, excipient, or vehicle. The NDV may be the AVINEW® NDV strain, a modified live vaccine commercialized by Merial Limited.

The herpesvirus antigen may be a glycoprotein. The herpesvirus antigen may be a glycoprotein B (gB) or glycoprotein D (gD) antigen from a feline herpesvirus.

The invention also relates to a method of vaccinating an animal comprising administering to the animal an effective amount of one or more vaccines or compositions which may comprise an effective amount of a recombinant NDV vector and optionally a pharmaceutically or veterinarily acceptable carrier, adjuvant, excipient, or vehicle. The administering may be by in ovo, oro-nasal, eye drop, spray, drinking water or parenteral (subcutaneous, intramuscular, transdermal, intradermal) administration.

The invention further relates to administration of the vaccine or composition using prime-boost protocol. The invention further encompasses a kit for performing a method of eliciting or inducing an immune response that may comprise any one of the recombinant herpesvirus immunological compositions or vaccines, or inactivated immunological compositions or vaccines, and instructions for performing the method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which:

FIG. 1 is a table showing the SEQ ID NO assigned to the DNA and protein sequences.

FIG. 4 depicts the maps of pFR14 and pFR16 plasmids.

FIG. 12 shows the gB protein sequence alignment and sequence identity percentage.

FIG. 13 shows the gD protein sequence alignment and sequence identity percentage.

DETAILED DESCRIPTION

Figure 2A:
FIG. 2A depicts a genetic map of the full length NDV genome.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

In the present invention, AVINEW® strain is used as the NDV vector (US2010/0255029).

The present invention relates to a vaccine or composition that may comprise an effective amount of one or more engineered NDV vectors, and optionally a pharmaceutically or veterinarily acceptable carrier, adjuvant, excipient, or vehicle.

The present invention encompasses an engineered NDV vector expressing a herpesvirus protein, polypeptide, antigen, epitope or immunogen that elicits an immunogenic response in an animal. The herpesvirus protein, polypeptide, antigen, epitope or immunogen may be a feline herpesvirus protein, polypeptide, antigen, epitope or immunogen.

As used herein, the term "herpesvirus polypeptide, antigen, epitope or immunogen" refers to any polypeptide, antigen, epitope or immunogen of a herpesvirus. The herpesvirus may be a feline herpesvirus, canine herpesvirus, phocid herpesvirus. The herpesvirus polypeptide may be herpesvirus glycoprotein, including but not limited to herpesvirus gB or gD protein.

By "animal" is intended mammals, human, birds, and the like. The animal may be selected from the group consisting of equine (e.g., horse), canine (e.g., dogs, wolves, foxes, coyotes, jackals), feline (e.g., lions, tigers, domestic cats, wild cats, other big cats, and other feline including cheetahs and lynx), ovine (e.g., sheep), bovine (e.g., cattle, cow, buffalo), swine (pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

In one embodiment, the herpesvirus immunological composition or vaccine comprises one or more engineered NDV vectors, and optionally a pharmaceutical or veterinary acceptable excipient, adjuvant, carrier or vehicle. The engineered NDV vector may be an NDV expression vector comprising a polynucleotide encoding a herpesvirus protein, polypeptide, antigen, epitope or immunogen. The herpesvirus protein, polypeptide, antigen, epitope or immunogen may be a glycoprotein, or any fragment thereof. The herpesvirus protein, polypeptide, antigen, epitope or immunogen may be a gB or gD protein, or any fragment thereof.

As used herein, the term "antigen" or "immunogen" means a substance that induces a specific immune response in a host animal. The antigen may comprise a whole organism, killed, attenuated or live; a subunit or portion of an organism; a recombinant vector containing an insert expressing an epitope, polypeptide, peptide, protein, or fragment thereof with immunogenic properties; a piece or fragment of nucleic acid capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope, also known as antigenic determinant, is the part of a macromolecule recognized by the immune system and able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term epitope is the part of a macromolecule recognized by the immune system and able to induce an immune reaction of the humoral type (B cells) and/or cellular type (T cells). The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The term "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. Immunogenic fragments, for purposes of the present invention, will usually include at least about 3 amino acids, about 5 amino acids, about 10-15 amino acids, about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of herpesvirus protein or polypeptide. A polynucleotide encoding a fragment of the total protein or polypeptide comprises or consists essentially of or consists of a minimum of 15 nucleotides, advantageously about 30-45 nucleotides, and preferably about 45-75, at least 57, 87 or 150 consecutive or contiguous nucleotides of the sequence encoding the total protein or polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999), can be used in the practice of the invention, without undue experimentation.

A "polynucleotide" is a polymeric form of nucleotides of any length that contains deoxyribonucleotides, ribonucleotides, and analogs in any combination. Polynucleotides may have three-dimensional structure, and may perform any function, known or unknown. The term "polynucleotide" includes double-, single-, and triple-stranded helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The term "codon optimization" refers to the process of optimally configuring the nucleic acid sequence encoding a protein, polypeptide, antigen, epitope, domain or fragment for expression/translation in a selected host. In general, gene expression levels depend on many factors, such as promoter sequences and regulatory elements. One of the most important factors is the adaptation of the codon usage of the transcript gene to the typical codon usage of the host (Lithwich, G. and Margalit, H., Genome Res. 13, 2665-2673, 2003). Therefore, highly expressed genes in prokaryotic genomes under translational selection have a pronounced codon usage bias. This is because they use a small subset of codons that are recognized by the most abundant tRNA species (Ikemura, T., J. Mol. Biol. 151, 389-409, 1981). The force that modulates this codon adaptation is called translational selection and its strength is important in fast-growing bacteria (Rocha, E. P., Genome Res. 14, 2279-2286, 2004; Sharp, P. M. et al., Nucleic Acids Res. 33, 1141-1153). If a gene contains codons that are rarely used by the host, its expression level will not be maximal. This may be one of the limitations of heterologous protein expression (Gustafsson, C. et al., Trends Biotechnol. 22, 346-353, 2004) and the development of DNA vaccines (Ivory, C. and Chadee, K., Genet. Vaccines Ther. 2, 17, 2004). A high number of synthetic genes have been re-designed to increase their expression level. The Synthetic Gene Database (SGDB) (Wu, G. et al., Nucleic Acids Res. 35, D76-D79, 2007) contains information from more than 200 published experiments on synthetic genes. In the design process of a nucleic acid sequence that will be inserted into a new host to express a certain protein in optimal amounts, codon usage optimization is usually one of the first steps (Gustafsson, C., Trends Biotechnol. 22, 346-353, 2004). Codon usage optimization basically involves altering the rare codons in the target gene so that they more closely reflect the codon usage of the host without modifying the amino acid sequence of the encoded protein (Gustafsson, C., Trends Biotechnol. 22, 346-353, 2004). The information usually used for the optimization process is therefore the DNA or protein sequence to be optimized and a codon usage table (reference set) of the host.

There are several public web servers and stand-alone applications that allow some kind of codon optimization by anyone skilled in the art. '*GeneDesign*' (Richardson, S. M. et al., Genome Res. 16, 550-556, 2006), '*Synthetic Gene Designer*' (Wu, G. et al., Protein Expr. Purif. 47, 441-445, 2006) and '*Gene Designer*' (Villalobos, A. et al., BMC Bioinformatics 7, 285, 2006) are packages that provide a platform for synthetic gene design, including a codon optimization step. With regard to the methods for codon usage optimization available in each server or program, the first programs developed used only the 'one amino acid—one codon' approach. More recent programs and servers now include further methods to create some codon usage variability. This variability reflects the codon usage variability of natural highly expressed genes and enables additional criteria to be introduced (such as the avoidance of restriction sites) in the optimization process. Most applications and web servers described herein provide three methods of codon optimization: a complete optimization of all codons, an optimization based on the relative codon usage frequencies of the reference set that uses a Monte Carlo approach and a novel approaches designed to maximize the optimization with the minimum changes between the query and optimized sequences.

In one embodiment, the nucleic acid sequence encoding the recombinant protein, antigen, peptide, polypeptide, fragment, domain, or epitope is codon optimized for expression in animal. In another embodiment, the codon optimized sequences encode feline herpesvirus proteins, antigens, peptides, polypeptides, fragments, domains, or epitopes for animal expression. In yet another embodiment, the codon optimized sequences encode herpesvirus gB or gD proteins, antigens, peptides, polypeptides, fragments, domains, or epitopes for animal expression.

The following are non-limiting examples of polynucleotides: a gene or gene fragment, exons, introns, mRNA, tRNA, rRNA, siRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a herpesvirus protein, antigen, epitope or immunogen. The complementary strand can be polymeric and of any length, and can contain deoxyribonucleotides, ribonucleotides, and analogs in any combination thereof.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is substantially free of the materials with which it is associated in its native environment. By substantially free, is meant at least 50%, at least 70%, at least 80%, at least 90%, or at least 95% free of these materials.

Hybridization reactions can be performed under conditions of different stringency. Conditions that increase stringency of a hybridization reaction are well known. See for example, "Molecular Cloning: A Laboratory Manual", second edition (Sambrook et al., 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the herpesvirus polypeptides and functionally equivalent fragments thereof that may enhance, decrease or not significantly affect inherent properties of the polypeptides encoded thereby. These functionally equivalent variants, derivatives, and fragments display the ability to retain the activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the herpesvirus polynucleotide or polypeptide of interest.

In one aspect, the present invention provides herpesvirus polypeptides, particularly herpesvirus gB polypeptides. In another aspect, the present invention provides a polypeptide having a sequence as set forth in SEQ ID NO: 1, 7, 8, 9, 11, 13, or 15, and variant or fragment thereof.

In another aspect, the present invention provides a polypeptide having at least 70%, at least 75%, at least 80%, at least 85%, at least 90%, at least 95%, 96%, 97%, 98% or 99% sequence identity to herpesvirus gB polypeptide of the invention, particularly to the polypeptide having a sequence as set forth in SEQ ID NO: 1, 7, 8, 9, 11, 13, or 15.

In yet another aspect, the present invention provides fragments and variants of the herpesvirus gB polypeptides identified above (SEQ ID NO: 1, 7, 8, 9, 11, 13, or 15) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 1, 7, 8, 9, 11, 13, or 15.

An immunogenic fragment of a herpesvirus gB polypeptide includes at least 8, 10, 15, or 20 consecutive amino acids, at least 21 amino acids, at least 23 amino acids, at least 25 amino acids, or at least 30 amino acids of the herpesvirus gB polypeptide having a sequence as set forth in SEQ ID NO: 1, 7, 8, 9, 11, 13, or 15, or variants thereof. In another embodiment, a fragment of the herpesvirus gB polypeptide includes a specific antigenic epitope found on a full-length herpesvirus gB polypeptide.

In another aspect, the present invention provides a polynucleotide encoding a herpesvirus gB polypeptide, such as a polynucleotide encoding a polypeptide having a sequence as set forth in SEQ ID NO: 1, 7, 8, 9, 11, 13, or 15. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 7, 8, 9, 11, 13, or 15, or a conservative variant, an allelic variant, a homolog or an immunogenic fragment comprising at least eight or at east ten consecutive amino acids of one of these polypeptides, or a combination of these polypeptides. The polynucleotide encoding the herpesvirus gB polypeptide may be codon-optimized for expression in a specific animal species.

In another aspect, the present invention provides a polynucleotide having a nucleotide sequence as set forth in SEQ ID NO: 2, 3, 10, 12, 14, or 16, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to a polynucleotide having a sequence as set forth in SEQ ID NO: 2, 3, 10, 12, 14, or 16, or a variant thereof.

In one aspect, the present invention provides herpesvirus polypeptides, particularly herpesvirus gD polypeptides. In another aspect, the present invention provides a polypeptide having a sequence as set forth in SEQ ID NO: 4, 17, 19, 21, or 23, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a herpesvirus gD polypeptide of the invention, particularly to the polypeptides having a sequence as set forth in SEQ ID NO: 4, 17, 19, 21, or 23.

In yet another aspect, the present invention provides fragments and variants of the herpesvirus gD polypeptides identified above (SEQ ID NO: 4, 17, 19, 21, or 23) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 4, 17, 19, 21, or 23.

An immunogenic fragment of a herpesvirus gD polypeptide includes at least 8, 10, 15, or 20 consecutive amino acids, at least 21 amino acids, at least 23 amino acids, at least 25 amino acids, or at least 30 amino acids of the herpesvirus gD polypeptide having a sequence as set forth in SEQ ID NO: 4, 17, 19, 21, or 23, or variants thereof. In another embodiment, a fragment of a herpesvirus gD polypeptide includes a specific antigenic epitope found on a full-length herpesvirus gD polypeptide.

In another aspect, the present invention provides a polynucleotide encoding a herpesvirus gD polypeptide, such as a polynucleotide encoding a polypeptide having a sequence as set forth in SEQ ID NO: 4, 17, 19, 21, or 23. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 4, 17, 19, 21, or 23, or a conservative variant, an allelic variant, a homolog or an immunogenic fragment comprising at least eight or at east ten consecutive amino acids of one of these polypeptides, or a combination of these polypeptides. The polynucleotide encoding the herpesvirus gD polypeptide may be codon-optimized for expression in a specific animal species.

In another aspect, the present invention provides a polynucleotide having a nucleotide sequence as set forth in SEQ ID NO: 5, 6, 18, 20, 22, or 24, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 5, 6, 18, 20, 22, or 24, or a variant thereof.

In general, comparison of amino acid sequences is accomplished by aligning an amino acid sequence of a polypeptide of a known structure with the amino acid sequence of a polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

Alternatively or additionally, the term "homology" or "identity", for instance, with respect to a nucleotide or amino acid sequence, can indicate a quantitative measure of homology between two sequences. The percent sequence identity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur et al., 1983), for instance, using a window size of 20 nucleotides, a word length of 4 nucleotides, and a gap penalty of 4, and computer-assisted analysis and interpretation of the sequence data including alignment can be conveniently performed using commercially available programs (e.g., Vector NTI Software™, Invitrogen Inc. CA, USA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. And, without undue experimentation, the skilled artisan can consult with many other programs or references for determining percent homology.

The invention further encompasses the herpesvirus polynucleotides contained in a vector molecule or an expression vector and operably linked to a promoter element and optionally to an enhancer.

A "vector" refers to a recombinant DNA or RNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term "vector" includes vectors for cloning as well as viral vectors.

The term "engineered" or "recombinant" means a polynucleotide of semisynthetic, or synthetic origin that either does not occur in nature or is linked to another polynucleotide in an arrangement not found in nature.

"Heterologous" means derived from a genetically distinct entity from the rest of the entity to which it is being compared. For example, a polynucleotide may be incorporated by genetic engineering techniques into a plasmid or vector derived from a different source, and is thus a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a herpesvirus polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors. When the polynucleotide encodes a polypeptide fragment, e.g. a herpesvirus peptide, advantageously, in the vector, an ATG is placed at 5' of the reading frame and a stop codon is placed at 3'. Other elements for controlling expression may be present, such as enhancer sequences, stabilizing sequences, such as intron and or untranslated 5' or 3' sequences and signal sequences permitting the secretion of the protein.

Methods for making and/or administering a vector or recombinants or plasmid for expression of gene products of the invention either in vivo or in vitro can be any desired method, e.g., a method which is by or analogous to the methods disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450; 6,312,683, and 6,596,279; U.S. patent application Ser. No. 12/753,597; WO 90/01543; W091/11525; WO 94/16716; WO 96/39491; WO 98/33510; EP 265785; EP 0 370 573.

The present invention also relates to a composition or vaccine comprising vectors, such as expression vectors. The composition or vaccine can comprise, consist essentially of, or consist of one or more vectors, e.g., expression vectors, such as in vivo expression vectors, comprising, consisting essentially or consisting of (or expressing) one or more of herpesvirus polypeptides, antigens, epitopes or immunogens. The vector contains and expresses a polynucleotide that comprises, consists essentially of, or consists of a polynucleotide coding for (or expressing) a herpesvirus antigen, epitope or immunogen, in a pharmaceutically or veterinarily acceptable carrier, adjuvant, excipient or vehicle.

According to another embodiment, the vector or vectors in the composition or vaccine comprise, or consist essentially of, or consist of polynucleotide(s) encoding one or more proteins or fragment(s) thereof a herpesvirus polypeptide, antigen, epitope or immunogen. The inventive composition or vaccine comprises, consists essentially of, or consists of, one or more vectors comprising, consisting essentially of, or consisting of, and advantageously also expressing, in vivo under appropriate conditions or suitable conditions or in a suitable host cell, polynucleotides from different herpesvirus isolates encoding the same proteins and/or for different proteins. The invention is also directed at mixtures of vectors that contain, consist essentially of, or consist of coding for, and express, different herpesvirus proteins, polypeptides, antigens, epitopes or immunogens, e.g., a herpesvirus polypeptide, antigen, epitope or immunogen from different species such as, but not limited to, feline, humans, canine, equine, bovine (e.g., cattle), swine, or avian.

The term plasmid covers any DNA transcription unit comprising a polynucleotide according to the invention and the elements necessary for its in vivo expression in a cell or cells of the desired host or target; and, in this regard, it is noted that a supercoiled plasmid and all of its topoisomers, open-circular plasmid, as well as linear forms of the plasmid, are intended to be within the scope of the invention.

Each plasmid comprises or contains or consists essentially of, in addition to the heterologous polynucleotide encoding a recombinant protein, antigen, epitope or immunogen, optionally fused with a polynucleotide encoding a heterologous peptide sequence, variant, analog or fragment, operably linked to a promoter or under the control of a promoter or dependent upon a promoter. In general, it is advantageous to employ a strong promoter that is functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter segment, which may or may not be associated with the enhancer segment. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter is either of a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., 1979).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Host cells include, but are not limited to, baby hamster kidney (BHK) cells, colon carcinoma (Caco-2) cells, COS7 cells, MCF-7 cells, MCF-10A cells, Madin-Darby canine kidney (MDCK) lines, mink lung (MvlLu) cells, MRC-5 cells, U937 cells, Chinese hamster ovary (CHO) cells, monkey Vero cells (cell line with the origin of the kidney of an African green monkey), quail (Quail muscle cell line QM7), chicken cell line DF1, and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In one embodiment of the present invention, the vector is a Newcastle Disease Virus (NDV) vector as described in US 2010/0255029 (incorporated herein by reference in its entireties). Newcastle disease virus designated as avian paramyxovirus 1 (APMV1, family Paramyxoviridae, subfamily Paramyxovirinae, genus Avulavirus) is an avian pathogen whose naturally occurring strains exhibit a wide range of disease severity. NDV is particularly advantageous as a vaccine vector for veterinary use because the vector itself serves as a needed poultry vaccine. NDV strain pathotypes are asymptomatic enteric (e.g., Ulster 2C, Queensland V4), lentogenic (e.g., Hitchner Bl, F (e.g., Asplin), La Sota), mesogenic (e.g., strain H, Mukteswar, Roakin, Beaudette C) or velogenic (e.g., Texas GB, NY parrot 70181, Italien, Milano, Herts 33/56). Advantages of herpesvirus vaccines based on the NDV vector include, but are not limited to, (1)

induce a broad immunity, including humoral, cellular and mucosal responses (2) do not express NP and M proteins and therefore is compatible with the DIVA (differentiate infected from vaccinated animals) strategy, (3) induce rapid onset of immunity, (4) bivalent, and (5) production poses less risk for the environment than inactivated vaccines in case of accidental release.

Certain characteristics of NDV suggest that recombinant NDV (rNDV) or engineered NDV expressing a foreign protein would be very good vaccine candidates. NDV grows to very high titers in many cell lines and eggs, and it elicits strong humoral and cellular immune responses in vivo. NDV naturally infects via respiratory and alimentary tract mucosal surfaces, so it is especially useful to deliver protective antigens of respiratory disease pathogens such as FHV. In addition, commercially available live NDV vaccines are widely used in the United States and most other countries. Vaccines based on live NDV recombinants may also have advantages over other live recombinant vaccine vectors. First, the foreign protein is expressed with only a few NDV proteins. In contrast, pox and herpes virus vectors express a large number of additional proteins from their large-size genomes. For the generation of specific immune responses in vaccine applications, it may be advantageous to have only a limited number of proteins expressed. Second, NDV replicates in the cytoplasm of the infected cells without a DNA phase, which eliminates the problem of integration of viral genome into the host cell DNA. The virus does not undergo detectable genetic recombination.

In one embodiment, the NDV vector is NDV AVINEW® (Merial's vaccine product containing the VG/GA strain of the Newcastle Disease virus) as described in US 2010/0255029. The NDV vector may also be the vector of U.S. Pat. No. 5,118,502, in particular the strain deposited as ATCC No. VR 2239 (ATCC: American Type Culture Collection).

In one aspect, the present invention relates to a pharmaceutical composition or vaccine for inducing an immunological response in a host animal inoculated with the vaccine or composition, the vaccine or composition including one or more modified AVINEW recombinant viral vectors. In yet another aspect of the invention, the engineered or recombinant AVINEW viral vector includes, within a non-essential region of the virus genome, a herpesvirus DNA sequence which encodes a herpesvirus antigenic protein derived from a pathogen wherein the composition or vaccine when administered to a host, is capable of inducing an immunological response specific to the protein encoded by the pathogen. The composition optionally comprises a pharmaceutically or veterinarily acceptable carrier or vehicle or adjuvant or excipient.

The term "nonessential region" refers to a region of a virus genome which is not essential for replication and propagation of the virus in tissue culture and whose deletion or inactivation may reduce virulence in a variety of animal systems. Any nonessential region or portion thereof can be deleted from the AVINEW genome or a foreign sequence can be inserted in it, and the viability and stability of the engineered AVINEW resulting from the deletion or insertion can be used to ascertain whether a deleted region or portion thereof is indeed nonessential. In another embodiment, the nonessential region of the AVINEW genome is the region between P gene and M gene, or the region between M gene and F gene of AVINEW genome. In one embodiment, the nonessential region is located upstream of the NP gene on the AVINEW genome. In another embodiment, the nonessential region is located downstream of the L gene on the AVINEW genome. In yet another embodiment, the nonessential region is a non-coding or intergenic region. In this aspect, the non-coding or intergenic region may be a region between NP and P genes, between P and M genes, between M and F genes, or between F and FIN genes on the AVINEW genome. In another embodiment, the nonessential region may be in the region of 1nt-121nt, 1591nt-1886nt, 3074nt-3289nt, 4384nt-4543nt, 6205nt-6411nt, 8262nt-8380nt, or 14995nt-15186nt of SEQ ID NO:27.

One aspect of the invention relates to engineered or recombinant NDV vectors expressing herpesvirus antigens. The antigen may be herpesvirus glycoprotein, such as gB or gD protein aforementioned. The engineered NDV vector may comprise one or more polynucleotides encoding one or more herpesvirus antigens. In another aspect, the engineered NDV-Herpesvirus vector comprises one or more polynucleotides encoding a Herpesvirus gB antigen or variant thereof, a Herpesvirus gD antigen or variant thereof, or a combination thereof.

In one embodiment, the invention provides for the administration of a therapeutically effective amount of a formulation for the delivery and expression of a protein, antigen, epitope or immunogen in a target cell. Determination of the prophylactically or therapeutically effective amount is routine experimentation for one of ordinary skill in the art. In another embodiment, the formulation comprises an expression vector comprising a polynucleotide that expresses a herpesvirus antigen, epitope or immunogen and a pharmaceutically or veterinarily acceptable carrier, vehicle, adjuvant or excipient. In another embodiment, the pharmaceutically or veterinarily acceptable carrier, vehicle, adjuvant or excipient facilitates transfection and/or improves preservation of the vector or protein.

The pharmaceutically or veterinarily acceptable carriers or vehicles or adjuvant or excipients are well known to the one skilled in the art. For example, a pharmaceutically or veterinarily acceptable carrier or vehicle or adjuvant or excipient can be sterile water, a 0.9% NaCl (e.g., saline) solution or a phosphate buffer. Other pharmaceutically or veterinarily acceptable carrier or vehicle or adjuvant or excipients that can be used for methods of this invention include, but are not limited to, poly-(L-glutamate) or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro); advantageously, the carrier, vehicle or adjuvant or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are but not exclusively suitable for plasmids, are those having the following formula:

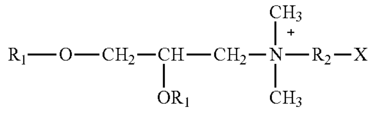

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

The plasmid mixture with the adjuvant is formed extemporaneously and/or contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio may be about 95:about 5 to about 5:about 95, or about 1:about 1, e.g., 1:1.

The DMRIE or DMRIE-DOPE adjuvant: plasmid weight ratio can be between about 50:about 1 and about 1:about 10, such as about 10:about 1 and about 1:about 5, and advantageously about 1:about 1 and about 1:about 2, e.g., 1:1 and 1:2.

In another embodiment, pharmaceutically or veterinarily acceptable carrier, adjuvant, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (see, e.g., U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of cross linked acrylic or methacrylic acid, especially cross linked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers cross linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are cross linked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or cross linked ethylene-maleic anhydride copolymers and they are, for example, cross linked by divinyl ether. Reference is also made to J. Fields et al., 1960.

With regard to structure, the acrylic or methacrylic acid polymers and EMA are preferably formed by basic units having the following formula:

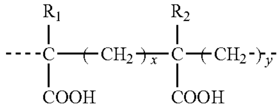

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between 0.01 and 1.5% w/v, 0.05 to 1% w/v or 0.1 to 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α(IL-1α), interleukin-1β(IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a feline cytokine for preparations to be administered to a feline).

In another embodiment, the composition of the present invention may be prepared using the chemical or physical procedure as described by Stauffer et al. (Recent Patents on Anti-Infective Drug Discovery, 1, 291-296, 2006). Some of the inactivation techniques are summarized in the table below.

| Chemical | Physical | Combined |
|---|---|---|
| Ascorbic Acid | | Ascorbic Acid + UV |
| b-Propiolactone | Heat | Beta Propiolactone + UV |
| b-aminophenylketone | Pressure | Formalin + Heat |
| diethylpyrocarbonate | UV | Formalin + UV |
| Ethylenimine | Non Ionic Detergents | Heat + Low Pressure |
| Formalin/Formaldehyde | | Pressure + Heat or Cold |
| Phenol | | Psoralen + UV |

The immunological composition and/or vaccine according to the invention comprise or consist essentially of or consist of an effective quantity to elicit a protective or therapeutic response of one or more expression vectors and/or polypeptides as discussed herein; and, an effective quantity can be determined from this disclosure, including the documents incorporated herein, and the knowledge in the art, without undue experimentation.

The compositions or vaccines of the present invention may be administered to an animal in ovo, via drinking water, oro-nasal, sprays, aerosols, intranasal instillation, eye drop, beak-dipping, by wing-web stabbing, transdermal, subcutaneous or intramuscular injection. Advantageously, the vaccines are administered by oro-nasal, subcutaneous, eye drop, spray or drinking water.

The present invention contemplates at least one administration to an animal of an efficient amount of the therapeutic composition made according to the invention. The therapeutic composition according to the invention can be administered by a needleless apparatus (as, for example with a Pigjet, Dermojet, Biojector, Vetjet or Vitajet apparatus (Bioject, Oregon, USA)).

In one embodiment of the invention, a prime-boost regimen can be employed, which is comprised of at least one primary administration and at least one booster administration using at least one common protein, polypeptide, antigen, epitope or immunogen. The immunological composition or vaccine used in primary administration is different in nature from those used as a booster. However, it is noted that the same composition can be used as the primary administration and the boost administration. This administration protocol is called “prime-boost”.

In another aspect of the prime-boost protocol of the invention, a composition comprising the engineered Avinew NDV Herpesvirus vaccine or composition is administered followed by the administration of vaccine or composition comprising a recombinant viral vector that contains and expresses a herpesvirus antigen in vivo, or an inactivated viral vaccine or composition comprising the herpesvirus antigen, or a vaccine or composition comprising a herpesvirus subunit (protein), or a DNA plasmid vaccine or composition that contains or expresses a herpesvirus antigen. Likewise, a prime-boost protocol may comprise the administration of vaccine or composition comprising a recombinant viral vector that contains and expresses a herpesvirus antigen in vivo, or an inactivated viral vaccine or composition comprising the herpesvirus antigen, or a vaccine or composition comprising a herpesvirus subunit (protein), or a DNA plasmid vaccine or composition that contains or expresses a herpesvirus antigen, followed by the administration of a composition comprising the engineered Avinew NDV Herpesvirus vaccine or composition. It is noted that both the primary and the secondary administrations may comprise the composition comprising the engineered Avinew NDV Herpesvirus vaccine or composition. It is further noted that both the primary and the secondary administrations may comprise one or more compositions comprising the engineered NDV-HV vectors of the present invention.

A prime-boost protocol comprises at least one prime-administration and at least one boost administration using at least one common antigen. The vaccine or composition used in prime-administration may be different in nature from those used as a later booster vaccine or composition. The prime-administration may comprise one or more administrations. Similarly, the boost administration may comprise one or more administrations.

The various administrations are preferably carried out about 1 to about 6 weeks apart, or about 2 to about 4 weeks apart. Repeated booster every 2 to 6 weeks or an annual booster is also contemplated. The animals are preferably at least one day old at the time of the first administration.

The immunological composition and/or vaccine contains per dose from about $10^4$ to about $10^{11}$, advantageously from about $10^5$ to about $10^{10}$ and more advantageously from about $10^6$ to about $10^9$ viral particles of recombinant adenovirus expressing a herpesvirus antigen, epitope or immunogen. In the case of immunological composition and/or vaccine based on a poxvirus, a dose can be between about $10^2$ pfu and about $10^9$ pfu. The immunological composition and/or vaccine contains per dose from about $10^2$ to about $10^7$, advantageously from about $10^3$ to about $10^5$ pfu of poxvirus or herpesvirus recombinant expressing the herpesvirus antigen, epitope or immunogen.

The viral vector may be an attenuated avipox expression vector. In one embodiment, the avipox expression vector may be a fowlpox vector, for example, TROVAC®. In another embodiment, the avipox expression vector may be a canarypox vector, for example, ALVAC®. The herpesvirus antigen, epitope or immunogen may be a herpesvirus glycoprotein, such as gB or gD. Other viruses that may be used in methods of the invention include, but are not limited to, vaccinia viruses, such as an attenuated vaccinia virus, for instance NYVAC, adenoviruses and herpesviruses.

The efficacy of the vaccines may be tested about 2 to 4 weeks after the last immunization by challenging animals with a virulent strain of herpesvirus. Both homologous and heterologous strains may be used for challenge to test the efficacy of the vaccine. The animal may be challenged by spray, intra-nasal, eye drop, oculo-nasal, IM, intra-tracheal, and/or oral. The challenge viral may be about $10^3$ to about $10^8$ in a volume depending upon the route of administration. For example, if the administration is by spray, a virus suspension is aerosolized to generate about 1 to 100 μm droplets, if the administration is intra-nasal, intra-tracheal or oral, the volume of the challenge virus is about 0.05 to about 5 ml. The dose volume of compositions for target species, e.g., the dose volume of feline compositions, may be about 50 μl for in ovo, about 20 to about 50 μl for eye drop, about 0.25 ml to about 1 ml for spray. Animals may be observed daily for 14 days following challenge for clinical signs and mortality. In addition, the groups of animals may be euthanized and evaluated for pathological findings. Oropharyngeal, tracheal or cloacal swabs may be collected from all animals post challenge for virus detection. The presence or absence of viral antigens in tissues may be evaluated by immunohistochemistry, viral isolation or titration, or nucleic acid detection such as reverse-transcriptase polymerase chain reaction (RT-PCR). Blood samples may be collected post-challenge and may be analyzed for the presence of anti-herpesvirus gB or gD virus-specific antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each immunization protocol, without any undue experimentation.

Another embodiment of the invention is a kit for performing a method of inducing an immunological or protective response against herpesvirus in an animal comprising a recombinant NDV immunological composition or vaccine or an inactivated herpesvirus immunological composition or vaccine and instructions for performing the method of delivery in an effective amount for eliciting an immune response in the animal.

The invention is further illustrated by the following non-limiting examples.

EXAMPLES

Construction of DNA inserts, plasmids and recombinant viral vectors was carried out using the standard molecular biology techniques known in the art, for example, described by J. Sambrook et al. (Molecular Cloning: A Laboratory Manual, 2nd Edition, Cold Spring Harbor Laboratory, Cold Spring Harbor, N.Y., 1989).

Example 1

Construction of the NDV Transcription Plasmids Containing Feline

Herpesvirus (FHV) gB Gene (pFR14 Plasmid) and gD Gene (pFR16 Plasmid)

Figure 3:
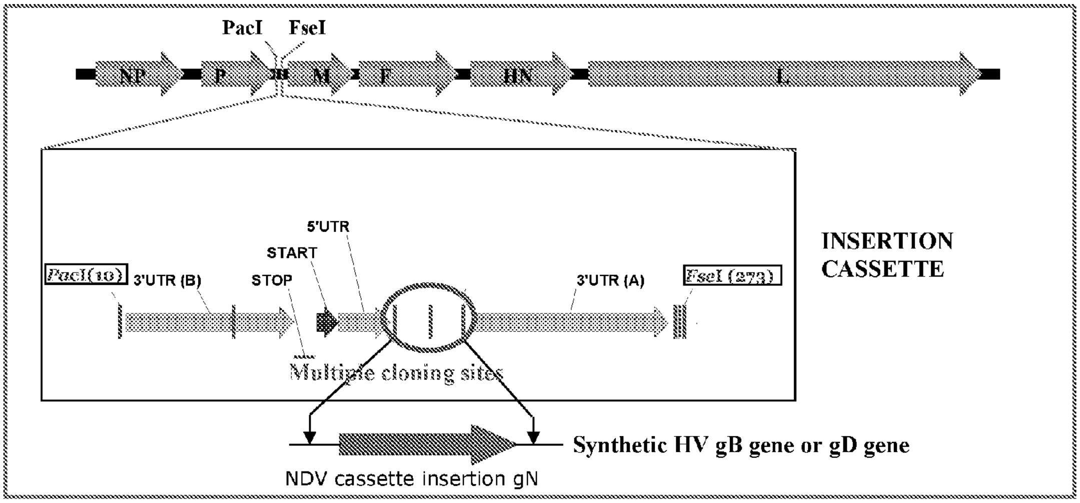
FIG. 3 depicts the generation of NDV transcription plasmid containing feline herpesvirus (FHV) gB gene (pFR14 plasmid) or gD gene (pFR16 plasmid).

The FHV gB gene inserted in the NDV genome was codon-optimized for expression in mammals. The synthetic FHV gB gene (SEQ ID NO:2) was cloned into a pBR322-based vector resulting in plasmid pFR13 which contains an insertion cassette as shown in FIG. 3. Plasmid pFR13 was digested with Pad and FseI generating a PacI-FseI fragment of 3105 bp in size. Plasmid pIV029 (US2010/0255029) was digested with Pad and FseI generating a FseI-PacI fragment of 19140 bp in size. The two fragments were ligated to generate plasmid pFR14 (FIG. 4).

The FHV gD gene inserted in the NDV genome was codon-optimized for expression in mammals. The synthetic FHV gD gene (SEQ ID NO:5) was cloned into a pBR322-based vector resulting in plasmid pFR15 which contains an insertion cassette as shown in FIG. 3. Plasmid pFR15 was digested with Pad and FseI generating a PacI-FseI fragment of 1373 bp in size. Plasmid pIV029 was digested with Pad and FseI generating a FseI-PacI fragment of 19140 bp in size. The two fragments were ligated to generate plasmid pFR16 (FIG. 4).

Example 2

Generation and Characterization of NDV Vector Expressing

FHV gB Gene (vAVW07)

Figure 2B:
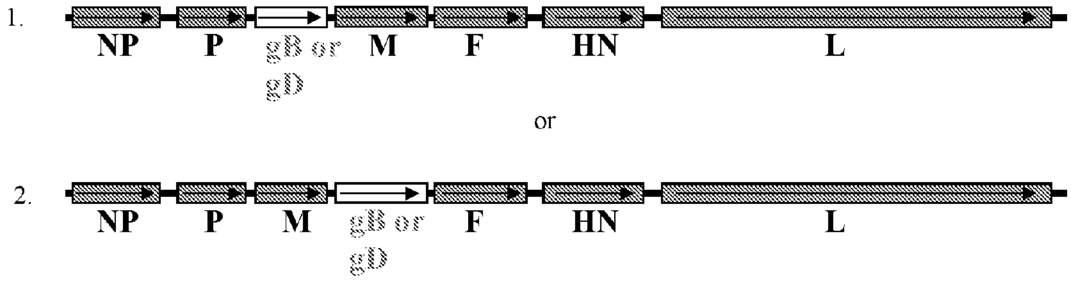
FIG. 2B depicts a map illustrating the genetic map of two engineered NDV vectors with herpesvirus gB or gD insertion into two representative intergenic insertion sites on the full length NDV genome.
Figure 2C:
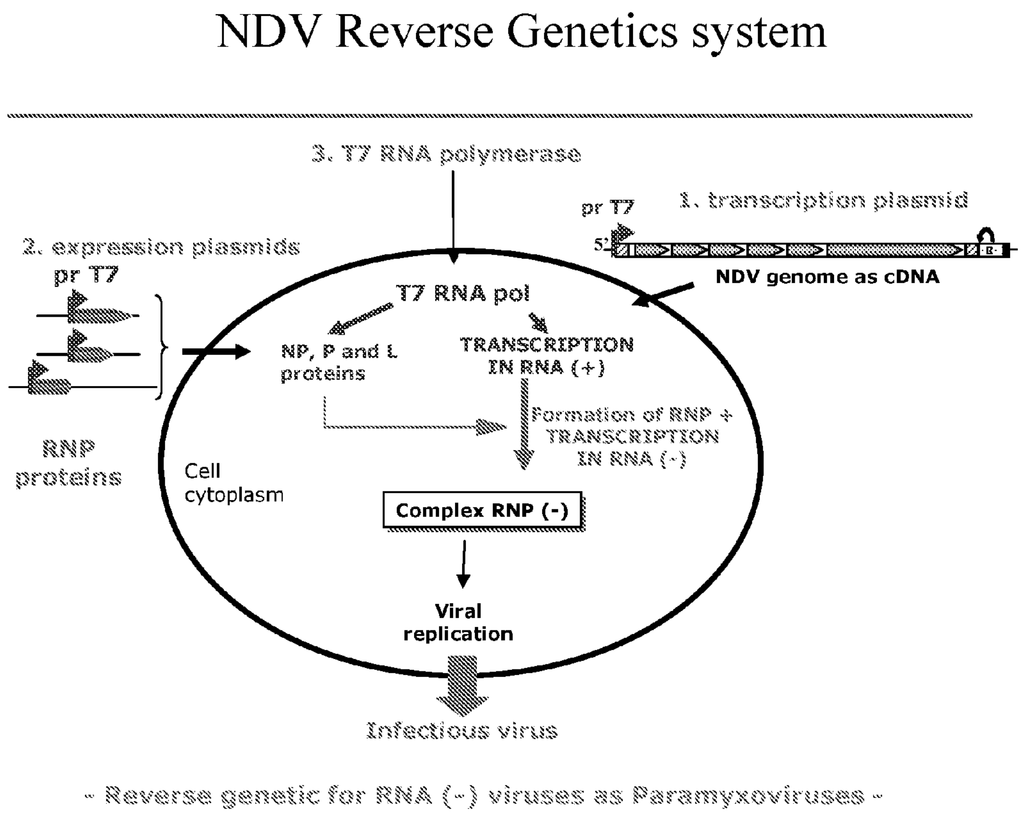
FIG. 2C is an example of flow diagram of the NDV reverse genetics system.

The NDV is a negative RNA virus and the generation of genetically modified NDV virus needs a reverse genetics system. The transcription of a full length genomic viral RNA and the simultaneous expression of NP, P and L proteins permit the assembly of RNP and the transcription of positive RNA into negative RNA genome. This initiates the normal replication cycle of NDV virus and permit the generation of infectious particles (see FIG. 2)

To generate engineered NDV vector expressing FHV gB gene, the following reagents and conditions were used. Plasmid pFR14 (see Example 1) was used as the transcription plasmid. Plasmids pIV32, pIV33 and pIV34 (US2010/0255029) were used as the expression plasmids for NP, P and L proteins, respectively. Plasmid pNS151 (US2010/0255029) was used as the T7 RNA polymerase plasmid. These five plasmids were co-transfected together into Chinese hamster ovary (CHO) cells, as shown schematically in FIG. 2C. After 72 hours, the CHO supernatants were inoculated in 10-day-old embryonated eggs to amplify the virus. After 3 days, the allantoic fluid was harvested and checked for hemagglutination activity (HA) using chicken red blood cells. The infectious particles of NDV-FHV gB were successfully obtained. RNA was extracted using QuiaAMP viral RNA extraction kit (Qiagen). RT-PCR was performed using One-Step RT-PCR kit (Qiagen). The sequencing result showed that the gB gene is 100% identical to the original sequence of the gB gene cloned in the transcription plasmid. The recombinant NDV-FHV gB viral vector is designated vAVW07.

Example 3

Generation and Characterization of NDV Vector Expressing

FHV gD Gene (vAVW08)

To generate engineered NDV vector expressing FHV gD gene, the following reagents and conditions were used. Plasmid pFR16 (see Example 1) was used as the transcription plasmid. Plasmids pIV32, pIV33 and pIV34 (US2010/0255029) were used as the expression plasmids for NP, P and L proteins, respectively. Plasmid pNS 151 (US2010/0255029) was used as the T7 RNA polymerase plasmid. These five plasmids were co-transfected together into Chinese hamster ovary (CHO) cells, as shown schematically in FIG. 2C. After 72 hours of transfection of CHO cells, the CHO supernatants were inoculated in 10-day-old embryonated eggs to amplify the virus. After 3 days, the allantoic fluid was harvested and checked for hemagglutination activity (HA) using chicken red blood cells. The infectious particles of NDV-FHV gD were successfully obtained.

RNA was extracted using QuiaAMP viral RNA extraction kit (Qiagen). RT-PCR was performed using One-Step RT-PCR kit (Qiagen). Two primers were used in the RT-PCR reaction:

```
FR09: CGCAGCTGCAATCAATTCAG     (SEQ ID NO: 25)

FR10: TGGGTGGACAGGGATCTGCT     (SEQ ID NO: 26)
```

The sequencing result showed that the gD gene is 100% identical to the original sequence of the gD gene cloned in the transcription plasmid. The recombinant NDV-HV gD viral vector is designated vAVW08.

Example 4

Clinical Evaluation of NDV-HV Vaccine in Cats

Thirty-two SPF (specific pathogen free) cats of 9-11 weeks were included in the study. Cats were randomly assigned to 4 groups of 8 cats (groups A to D) according to litter, sex and age by using a randomization table with 4 elements. Cats were cared and housed according to local husbandry and animal welfare procedures.

The experimental design is shown in Table 1.

TABLE 1 experimental design for vaccination in cats

| group | SPF cat 9-11 w | Treatment on D0 (V1) and D28 (V2) 1 mL | Challenge | Clinical follow-up | Viral shedding | Serology |
|---|---|---|---|---|---|---|
| A (NDV-HV by ON) | 8 | NDV-HV* 1 mL by ON** | FHV 1 mL by oculo-nasal route on D45 (~2 w post-V2) | typical clinical signs: daily from D45 to D59 bodyweight: D45, D49, D51, D53, D55, D57 and D59 | nasal swabs: D45 D47 D49 D51 D53 D55 D57 D59 | ELISA gB: D0 D28 D45 D59 |
| B (NDV-HV by SC) | 8 | NDV-HV* 1 mL by SC** | | | | |
| C (positive control)*** | 8 | positive control 1 dose by SC** | | | | |
| D (control) | 8 | none | | | | |

*NDV-HV = NDV-HV gB and NDV-HV gD, both at $10^{7.8}$ $EID_{50}$/mL

**ON = oro-nasal SC = subcutaneous

***positive control = vaccine containing attenuated feline Herpesvirus F2 strain, Merial Limited.

On D0 and D28, NDV-HV gB and NDV-HV gD vaccines were diluted 1/25 and 1/35, respectively, in order to reach a titer of $10^{7.8}$ $EID_{50}$/mL for both vaccines. Then, each cat from group A received under general anesthesia 1 mL of the NDV-HV vaccine (NDV-HV gB and NDV-HV gD) by oro-nasal route (0.25 mL per nostril and 0.5 ml in the mouth). Cats from group B received 1 mL of the NDV-HV vaccine by subcutaneous route between the shoulders. Cats from group C received one dose of the control vaccine by subcutaneous route between the shoulders. Cats from group D were not vaccinated.

On D45, each cat was administered under general anesthesia 1 mL of diluted 1/50 challenge strain $10^{5.56}$CCID50/mL (0.25 mL per nostril and 0.25 mL per eye).

Figure 5:
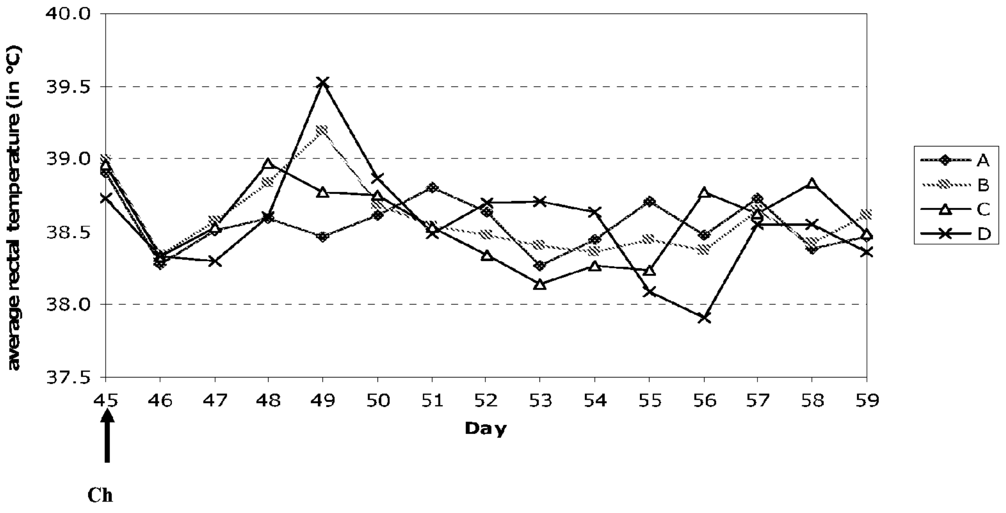
FIG. 5 shows the average rectal temperature of cats after the challenge. Group A is NDV-HV by ON, group B is NDV-HV by SC, group C is positive control (vaccine containing attenuated feline Herpesvirus F2 strain, Merial Limited), group D is negative control (no vaccination).

The rectal temperature test is shown in FIG. 5. Group A is NDV-HV by ON, group B is NDV-HV by SC, group C is positive control (vaccine containing attenuated feline Herpesvirus F2 strain, Merial Limited), group D is control (no vaccination). The result showed that in the control group, 7/8 cats had hyperthermia. In the vaccination groups, there was no hyperthermia with positive control and NDV-HV by ON, there was hyperthermia in 4/8 cats vaccinated with NDV-HV by SC.

Figure 6:
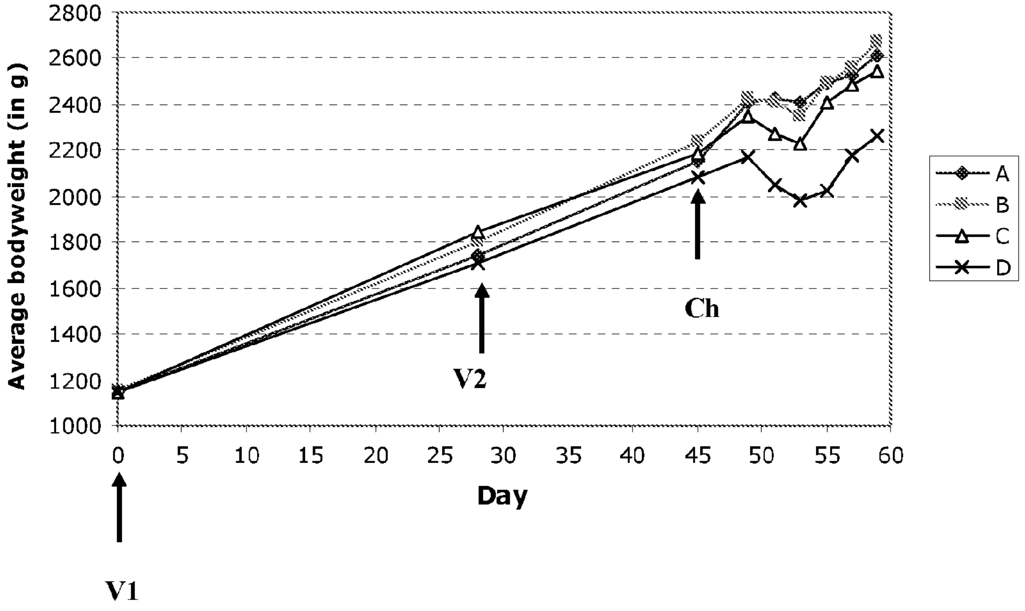
FIG. 6 shows the average bodyweight of cats after the challenge. Group A is NDV-HV by ON, group B is NDV-HV by SC, group C is positive control (vaccine containing attenuated feline Herpesvirus F2 strain, Merial Limited), group D is negative control (no vaccination).

The bodyweight result is shown in FIG. 6 and Table 2. All cats gained weight during immunization phase and growth was similar between groups.

Post challenge (pc), in group D, all cats lost weight from day 4 pc to day 8 pc. Some cats (3 out of 8) lost weight until day 10 pc. Then all cats gained weight. During the post challenge monitoring period, a weight loss >5% was recorded in 6 out of 8 cats on one or two occasions. In group C, a weight loss was observed in 6 out of 8 cats between day 4 pc and day 6 or day 8 pc. This weight loss was >5% in 4 cats. In group B, all cats lost weight between day 4 and day 6 or day 8 pc. A weight loss >5% was observed once in only 2 cats.

TABLE 2 weight loss observed during the post challenge monitoring period

| group | # cats with weight loss (# cats with weight loss > 5%) | Average weight loss observed Between D49 and D51 | Between D51 and D53 |
|---|---|---|---|
| A (NDV-HV by ON) | 5/8 (1/8) | +1% | +0% |
| B (NDV-HV by SC) | 6/8 (2/8) | −1% | −3% |
| C (positive control) | 6/8 (4/8) | −3% | −2% |
| D (controls) | 8/8 (6/8) | −2.5% | −7% |

Figure 7:
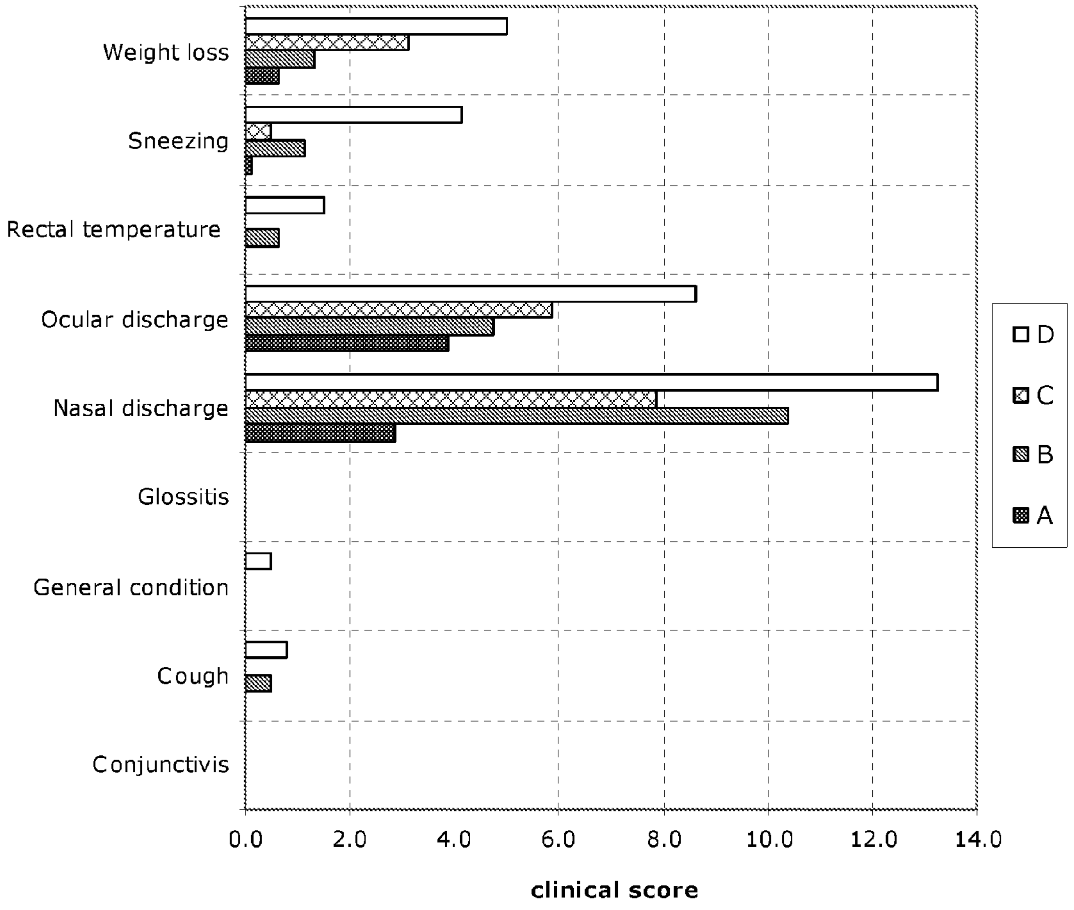
FIG. 7 shows the data collected on clinical signs of the cats after challenge. Group A is NDV-HV by ON, group B is NDV-HV by SC, group C is positive control (vaccine containing attenuated feline Herpesvirus F2 strain, Merial Limited), group D is negative control (no vaccination).

FIG. 7 shows the mean clinical scores per group following challenge and table 3 summarizes the clinical symptoms observed. Group A is NDV-HV by ON, group B is NDV-HV by SC, group C is positive control (vaccine containing attenuated feline Herpesvirus F2 strain, Merial Limited), group D is control (no vaccination). In group D, all cats developed clinical signs post challenge. In group A, one cat did not show any clinical sign post challenge and 3 cats presented only slight nasal discharge for one day or slight ocular discharge for 2 days. The other cats from group A, cats from group B and cats from group C presented less severe and more transient clinical signs than cats on group D.

TABLE 3 summary of the clinical signs observed per group post challenge

| | Nasal discharge (copious) | | Ocular discharge (copious) | | sneezing | | cough | | apathy | |
|---|---|---|---|---|---|---|---|---|---|---|
| Group | # cat | # occurrence | # cat | # occurrence | # cat | # occurrence | # cat | # occurrence | # cat | # occurrence |
| A | 6/8 (3/8) | 1-6 (1-2) | 5/8 (4/8) | 1-7 (1-4) | 1/8 | 1 | 0/8 | NA | 0/8 | NA |
| B | 8/8 (8/8) | 3-11 (1-5) | 8/8 (6/8) | 2-6 (1-3) | 6/8 | 1-2 | 2/8 | 1 | 0/8 | NA |
| C | 8/8 (7/8) | 1-11 (1-7) | 8/8 (4/8) | 1-7 (2-4) | 4/8 | 1 | 0/8 | NA | 0/8 | NA |
| D | 8/8 (8/8) | 8-10 (3-9) | 8/8 6/8) | 3-9 (2-5) | 8/8 | 2-6 | 3/8 | 1 | 1/8 | 2 |

Figure 8:
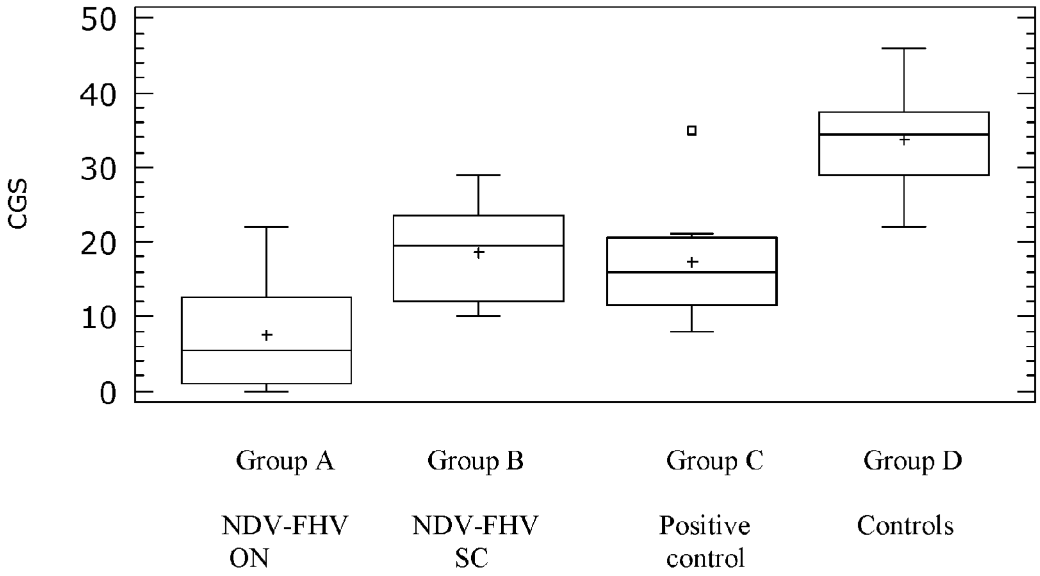
FIG. 8 shows the statistical analysis of the clinical global signs (CGS) of the cats after the challenge. Group A is NDV-HV by ON, group B is NDV-HV by SC, group C is positive control (vaccine containing attenuated feline Herpesvirus F2 strain, Merial Limited), group D is negative control (no vaccination).

FIG. 8 shows the distribution of global clinical score per group. The mean global clinical score was: 7.5 in group A, 18.6 in group B, 17.4 in group C, and 33.8 in group D. There was a significant difference between group D and the three vaccinated groups. There was a significant difference on the clinical global score between the three vaccinated groups (ANOVA, p=0.018). Cats from group A showed a significantly reduced clinical global score than cats from groups B and C. There was no significant difference for the global clinical score between groups B and C.

Figure 9:
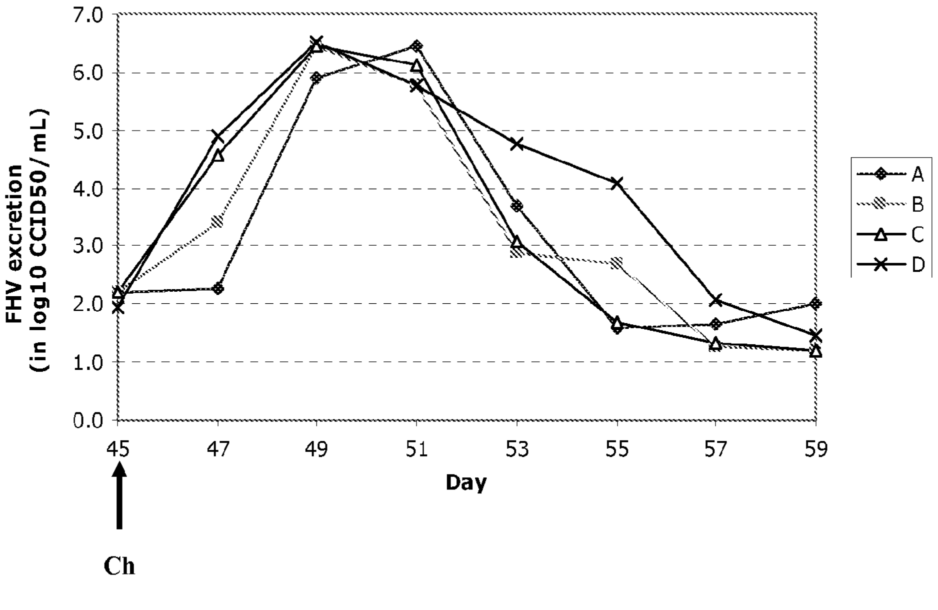
FIG. 9 depicts the viral shedding of the cats after the challenge. Group A is NDV-HV by ON, group B is NDV-HV by SC, group C is positive control (vaccine containing attenuated feline Herpesvirus F2 strain, Merial Limited), group D is negative control (no vaccination).

FIG. 9 shows the mean viral shedding per group post challenge and table 4 summarizes the mean AUC per group. Group A is NDV-HV by ON, group B is NDV-HV by SC, group C is positive control (vaccine containing attenuated feline Herpesvirus F2 strain, Merial Limited), group D is control (no vaccination).

TABLE 4 mean Area Under Curve (AUC) per group

| Group | Average AUC |
|---|---|
| A | 47.2 |
| B | 48.3 |
| C | 49.9 |
| D | 59.6 |

No cats shed feline Herpesvirus before challenge. Post challenge, FHV was isolated in all cats. In group D, excretion increased rapidly and peaked at day 4 pc, then regularly decreased until day 14 pc. On day 14 pc, 5 out of 8 cats still shed low quantity of virus. In the vaccinated groups, viral excretion peaked at day 4 pc in groups B and C or at day 6 pc in group A, then decreased more rapidly than in group D. On day 14 pc, no cat shed virus.

Figure 10:
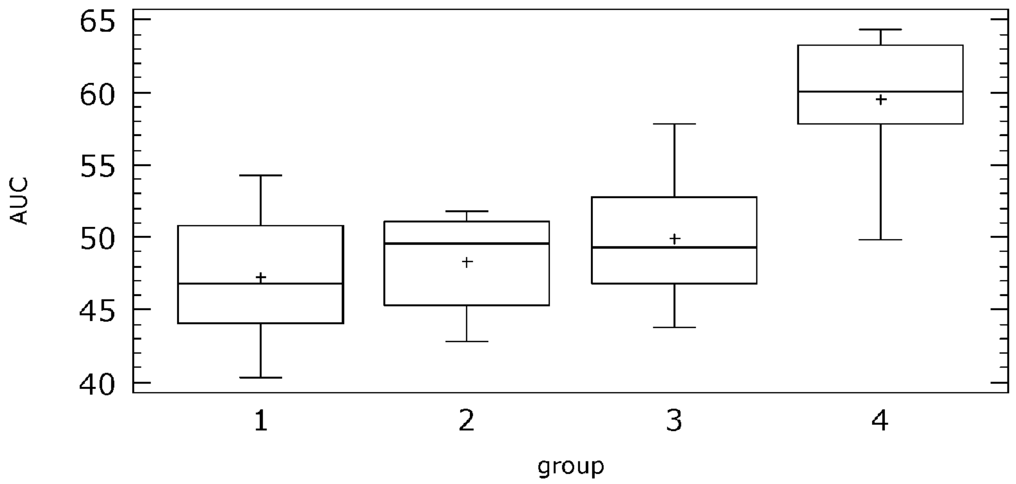
FIG. 10 is the statistical analysis of the viral shedding of the cats after the challenge. Group A is NDV-HV by ON, group B is NDV-HV by SC, group C is positive control (vaccine containing attenuated feline Herpesvirus F2 strain, Merial Limited), group D is negative control.

FIG. 10 shows the distribution of global viral shedding score per group. Viral shedding was significantly reduced in vaccinated groups compared to group D (no vaccination). Although cats from group A shed virus later than the other vaccinated groups, there was no statistically significant difference on the viral excretion between the three vaccinated groups (ANOVA, p=0.464).

Figure 11:
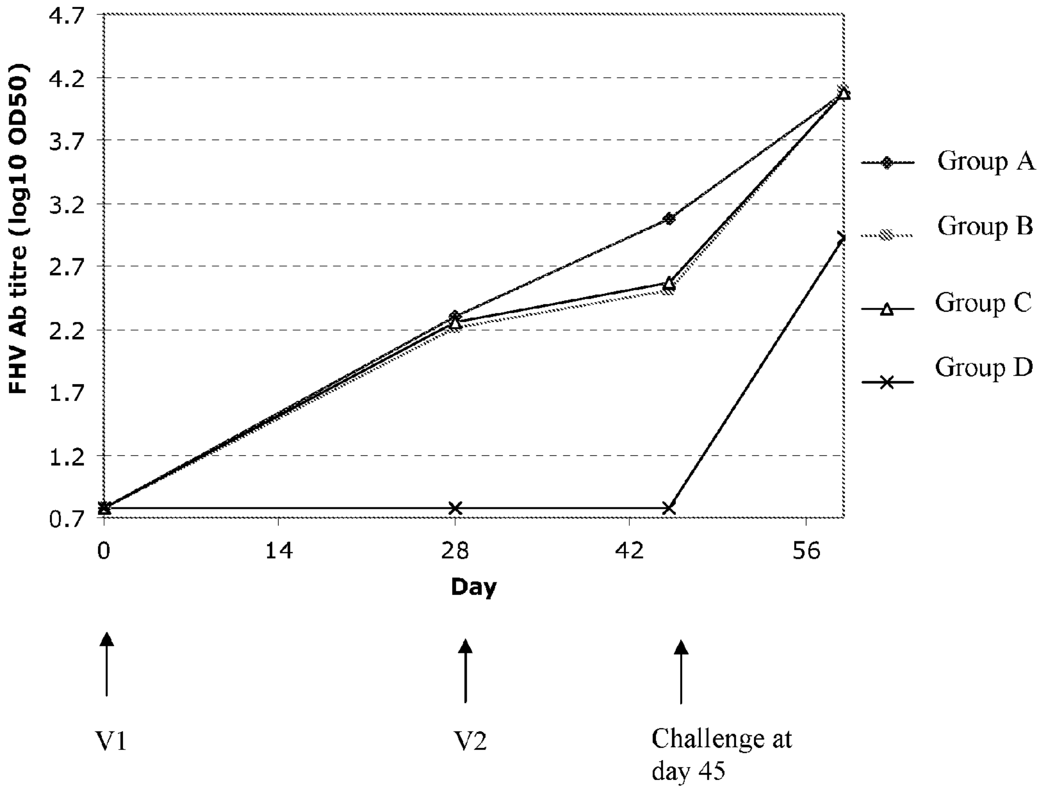
FIG. 11 shows the evolution of the mean FHV Ab (anti-gB) titer per group. Group A is NDV-HV by ON, group B is NDV-HV by SC, group C is positive control (vaccine containing attenuated feline Herpesvirus F2 strain, Merial Limited), group D is negative control (no vaccination).

The serology (anti-gB FHV Ab) data is shown in FIG. 11. Group A is NDV-HV by ON, group B is NDV-HV by SC, group C is positive control (vaccine containing attenuated feline Herpesvirus F2 strain, Merial Limited), group D is control (no vaccination). All cats were seronegative for gB-FHV on D0. All cats in group D remained seronegative until the challenge day. All cats in group D were positive for gB FHV Ab after D28. One injection of NDV-HV by SC or ON was sufficient to induce a seroconvesion in all cats. Challenge induced a booster effect in all vaccinates and the production of FHV Ab in all control cats. The serology data correlate well with the clinical results.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. A composition comprising:

(i) a recombinant Newcastle Disease Virus (NDV) vector, wherein the NDV vector comprises a genome having the sequence as set forth in SEQ ID NO:27, and (ii) a pharmaceutically or veterinarily acceptable carrier; wherein the recombinant NDV vector further comprises a first heterologous polynucleotide encoding a feline Herpesvirus glycoprotein B (gB) and a second heterologous polynucleotide encoding a feline Herpesvirus glycoprotein D (gD) inserted into said genome.

2. The composition of claim 1, wherein the gB protein has at least 90% sequence identity to SEQ ID NO:1 and the gD protein has at least 90% sequence identity to SEQ ID NO:4.

3. The composition of claim 1, wherein the recombinant NDV vector comprises a polynucleotide having at least 90% sequence identity to SEQ ID NO:2, 3, 5, or 6.

4. A recombinant NDV vector, wherein said NDV vector comprises a genome having the sequence as set forth in SEQ ID NO:27, wherein said vector further comprises two polynucleotides encoding a feline Herpesvirus glycoprotein B (gB) and a feline Herpesvirus glycoprotein D (gD).

5. The recombinant NDV vector of claim 4, wherein the gB and gD have at least 90% sequence identity to SEQ ID NO:1 or SEQ ID NO:4.

6. The recombinant NDV vector of claim 4, wherein the polynucleotides have at least 90% sequence identity to SEQ ID NO:2, 3, 5, or 6.

7. The recombinant NDV vector of claim 4, wherein the polynucleotides are inserted into one or more non-essential region(s) of the NDV genome.

8. A method of eliciting a protective immune response in an animal comprising administering to the animal an effective amount of the composition of claim 1.

9. The method of claim 8, wherein the gB protein has at least 90% sequence identity to SEQ ID NO:1 and the gD protein has at least 90% sequence identity to SEQ ID NO:4.

10. The method of any one of claim 8 or 9, wherein the administering is through oro-nasal, in ovo, ocular, intramuscular, subcutaneous, intradermal, or transdermal administration, or wherein the administering is through delivery via a spray or drinking water.

11. The method of claim 8, wherein the administering is prime-boost.

12. The method of claim 8, wherein the animal is a feline or canine.

13. The composition of claim 1, wherein the gB protein has at least 90% sequence identity to SEQ ID NO:1.

14. The composition of claim 1, wherein the gD protein has at least 90% sequence identity to SEQ ID NO:4.

15. The composition of claim 1, wherein the first polynucleotide has at least 90% sequence identity to SEQ ID NO:2 or 3.

16. The composition of claim 1, wherein the second polynucleotide has at least 90% sequence identity to SEQ ID NO:5 or 6.

* * * * *